United States Patent
Peoples et al.

(10) Patent No.: US 11,851,458 B2
(45) Date of Patent: *Dec. 26, 2023

(54) DEPSIPEPTIDE AND USES THEREOF

(71) Applicant: NovoBiotic Pharmaceuticals, LLC, Cambridge, MA (US)

(72) Inventors: Aaron J. Peoples, Somerville, MA (US); Dallas Hughes, Bolton, MA (US); Losee Lucy Ling, Arlington, MA (US); William Millett, Worcester, MA (US); Anthony Nitti, Lexington, MA (US); Amy Spoering, Waltham, MA (US); Victoria Alexandra Steadman, Ongar (GB); Jean-Yves Christophe Chiva, Ongar (GB); Linos Lazarides, Ongar (GB); Michael Kenyon Jones, Ongar (GB); Karine Gaelle Poullennec, Ongar (GB); Kim Lewis, Newton, MA (US); Slava Epstein, Dedham, MA (US)

(73) Assignee: NovoBiotic Pharmaceuticals, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/500,761

(22) Filed: Oct. 13, 2021

(65) Prior Publication Data

US 2022/0289793 A1    Sep. 15, 2022

Related U.S. Application Data

(63) Continuation of application No. 16/529,342, filed on Aug. 1, 2019, now Pat. No. 11,174,290, which is a continuation of application No. 15/183,031, filed on Jun. 15, 2016, now Pat. No. 10,414,800, which is a continuation of application No. 14/789,819, filed on Jul. 1, 2015, now Pat. No. 9,402,878, which is a continuation of application No. 14/095,415, filed on Dec. 3, 2013, now Pat. No. 9,163,065.

(60) Provisional application No. 61/732,894, filed on Dec. 3, 2012.

(51) Int. Cl.
| | |
|---|---|
| *A61K 38/15* | (2006.01) |
| *A61K 38/00* | (2006.01) |
| *C07K 7/56* | (2006.01) |
| *C07K 11/02* | (2006.01) |
| *C12P 21/02* | (2006.01) |
| *C12P 17/14* | (2006.01) |
| *C12N 1/20* | (2006.01) |
| *C12R 1/01* | (2006.01) |

(52) U.S. Cl.
CPC ............. *C07K 7/56* (2013.01); *A61K 38/15* (2013.01); *C07K 11/02* (2013.01); *C12N 1/205* (2021.05); *C12P 17/14* (2013.01); *C12P 21/02* (2013.01); *A61K 38/00* (2013.01); *C12R 2001/01* (2021.05); *Y02A 50/30* (2018.01)

(58) Field of Classification Search
None
See application file for complete search history.

(56) References Cited

U.S. PATENT DOCUMENTS

| | | |
|---|---|---|
| 9,163,065 B2 | 10/2015 | Peoples et al. |
| 9,402,878 B2 | 8/2016 | Peoples et al. |
| 10,414,800 B2 | 9/2019 | Peoples et al. |
| 11,174,290 B2 | 11/2021 | Peoples et al. |
| 2015/0313960 A1 | 11/2015 | Peoples et al. |

OTHER PUBLICATIONS

Baltz et al., Natural products to drugs: daptomycin and related lipopeptide antibiotics. Nat Prod Rep. Dec. 2005,22(6):717-41.
Kang et al., Characterization of genes involved in Biosynthesis of a novel antibiotic from Burkholderia cepacia BC11 and their role in biological control of Rhizoctonia solani. Microbiology. 1998;62(10):3939-47.
Klausmeyer et al., Histone deacetylase inhibitors from Burkholderia thailandensis. J Nat Prod. Oct. 28, 2011;74(10):2039-44.
Kuznedelov et al., The antibacterial threaded-lasso peptide capistruin inhibits bacterial RNA polymerase. J Mol Biol. 2011;412:842-848.
Ohno et al., Isolation of heptadepsin, a novel bacterial cyclic depsipeptide that inhibits lipopolysaccharide activity. Chem Biol. Aug. 2004;11(8):1059-70.
Sansinenea et al., Secondary metabolites of soil *Bacillus* spp. Biotechnol Lett. Aug. 2011;33(8):1523-38.
Sigma-Aldrich, Peptide Solubility. Retrieved online at: http://www.sigmaaldrich.com/life-science/custom-oligos/custom-peptides/learning center/peptide solubility.html. 2 pages. Retrieved Apr. 25, 2015.

*Primary Examiner* — Thomas S Heard
(74) *Attorney, Agent, or Firm* — McCarter & English, LLP; Maria Laccotripe Zacharakis; Yelena Margolin

(57) ABSTRACT

The present invention relates generally to novel depsipeptides, to methods for the preparation of these novel depsipeptides, to pharmaceutical compositions comprising the novel depsipeptides; and to methods of using the novel depsipeptides to treat or inhibit various disorders.

20 Claims, 7 Drawing Sheets

DEPSIPEPTIDE AND USES THEREOF

RELATED APPLICATIONS

This application is a continuation of U.S. patent application Ser. No. 16/529,342, filed on Aug. 1, 2019; which is a continuation of U.S. patent application Ser. No. 15/183,031, filed on Jun. 15, 2016; which is a continuation of U.S. patent application Ser. No. 14/789,819, filed on Jul. 1, 2015, now U.S. Pat. No. 9,402,878, issued on Aug. 2, 2016; which is a continuation of U.S. patent application Ser. No. 14/095,415, filed on Dec. 3, 2013, now U.S. Pat. No. 9,163,065, issued on Oct. 20, 2015; which claims the benefit of U.S. Provisional Patent Application No. 61/732,894, filed on Dec. 3, 2012. The entire contents of each of the foregoing applications are incorporated herein by reference.

GOVERNMENT SUPPORT

This invention was made with Government support under Grant No. R43AI085612 awarded by the National Institutes of Health. The Government has certain rights in the invention.

BACKGROUND OF THE INVENTION

Among modern medicine's great achievements is the development and successful use of antimicrobials against disease-causing microbes. Antimicrobials have saved numerous lives and reduced the complications of many diseases and infections. However, the currently available antimicrobials are not as effective as they once were.

Over time, many microbes have developed ways to circumvent the anti-microbial actions of the known antimicrobials, and in recent years there has been a worldwide increase in infections caused by microbes resistant to multiple antimicrobial agents. With the increased availability and ease of global travel, rapid spread of drug-resistant microbes around the world is becoming a serious problem. In the community, microbial resistance can result from nosocomial acquisition of drug-resistant pathogens (e.g., methicillin resistant *Staphylococcus aureus* (MRSA), vancomycin resistant *Enterococci* (VRE)), emergence of resistance due to use of antibiotics within the community (e.g., penicillin- and quinolone-resistant *Neisseria gonorrheae*), acquisition of resistant pathogens as a result of travel (e.g., antibiotic-resistant *Shigella*), or as a result of using antimicrobial agents in animals with subsequent transmission of resistant pathogens to humans (e.g., antibiotic resistant *Salmonella*). Antibiotic resistance in hospitals has usually resulted from overuse of antibiotics and has been a serious problem with MRSA, VRE, and multi-drug resistant Gram-negative bacilli (MDR-GNB) (e.g., *Enterobacter, Klebsiella, Serratia, Citrobacter, Pseudomonas,* and *E. coli*). In particular, catheter-related blood stream infections by bacteria and skin and soft tissue infections (SSTIs) are becoming an increasing problem.

Bacteria, viruses, fungi, and parasites have all developed resistance to known antimicrobials. Resistance usually results from three mechanisms: (i) alteration of the drug target such that the antimicrobial agent binds poorly and thereby has a diminished effect in controlling infection; (ii) reduced access of the drug to its target as a result of impaired drug penetration or active efflux of the drug; and (iii) enzymatic inactivation of the drug by enzymes produced by the microbe. Antimicrobial resistance provides a survival advantage to microbes and makes it harder to eliminate microbial infections from the body. This increased difficulty in fighting microbial infections has led to an increased risk of developing infections in hospitals and other settings. Diseases such as tuberculosis, malaria, gonorrhea, and childhood ear infections are now more difficult to treat than they were just a few decades ago. Drug resistance is a significant problem for hospitals harboring critically ill patients who are less able to fight off infections without the help of antibiotics. Unfortunately, heavy use of antibiotics in these patients selects for changes in microbes that bring about drug resistance. These drug resistant bacteria are resistant to our strongest antibiotics and continue to prey on vulnerable hospital patients. It has been reported that 5 to 10 percent of patients admitted to hospitals acquire an infection during their stay and that this risk has risen steadily in recent decades.

In view of these problems, there is an increasing need for novel antimicrobials to combat microbial infections and the problem of increasing drug resistance. A renewed focus on antimicrobial drug discovery is critical as pathogens are developing resistance to available drugs.

Synthetic compounds have thus far failed to replace natural antibiotics and to lead to novel classes of broad-spectrum compounds, despite the combined efforts of combinatorial synthesis, high-throughput screening, advanced medicinal chemistry, genomics and proteomics, and rational drug design. The problem with obtaining new synthetic antibiotics may be related in part to the fact that the synthetic antibiotics are invariably pumped out across the outer membrane barrier of bacteria by Multidrug Resistance pumps (MDRs). The outer membrane of bacteria is a barrier for amphipathic compounds (which essentially all drugs are), and MDRs extrude drugs across this barrier. Evolution has produced antibiotics that can largely bypass this dual barrier/extrusion mechanism, but synthetic compounds almost invariably fail.

SUMMARY OF THE INVENTION

This application is directed, at least in part, to a novel depsipeptide that is useful in the treatment of a number of disorders, including microbial infections.

In one embodiment, the present invention relates to an isolated compound of Formula (I):

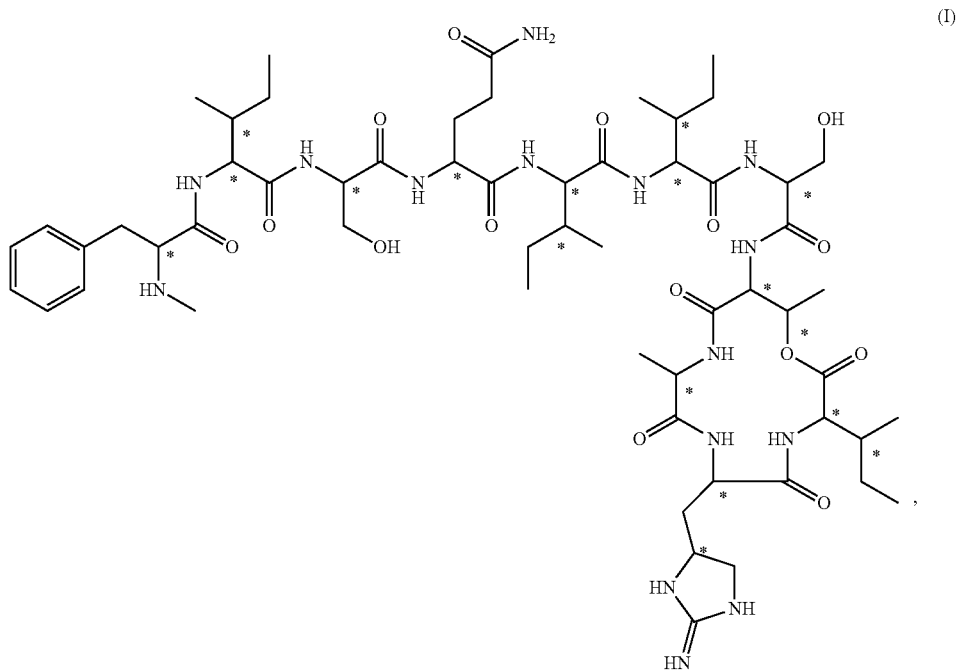 [SMILES: CCC(C)C(NC(=O)C(Cc1ccccc1)NC)C(=O)NC(CO)C(=O)NC(CCC(N)=O)C(=O)NC(C(=O)NC(C(=O)NC(CO)C(=O)NC1C(=O)NC(C)C(=O)NC(CC2CNC(=N)N2)C(=O)NC(C(C)CC)C(=O)OC1C)C(C)CC)C(C)CC]

(I)

or an enantiomer, diastereomer, tautomer, or pharmaceutically-acceptable salt thereof, wherein each stereocenter (indicated with an "*") can be either the R or S configuration.

In some embodiments, the compound of Formula (I) is an isolated natural product of a bacterial species. For example, in some embodiments, the compound of Formula (I) is an isolated natural product of bacterial isolate ISO18629. In some embodiments, the compound of Formula (I) is producible from a bacterial species. For example, in some embodiments, the compound of Formula (I) is producible from bacterial isolate ISO18629.

In another embodiment, the present invention relates to an isolated compound of Formula (II):

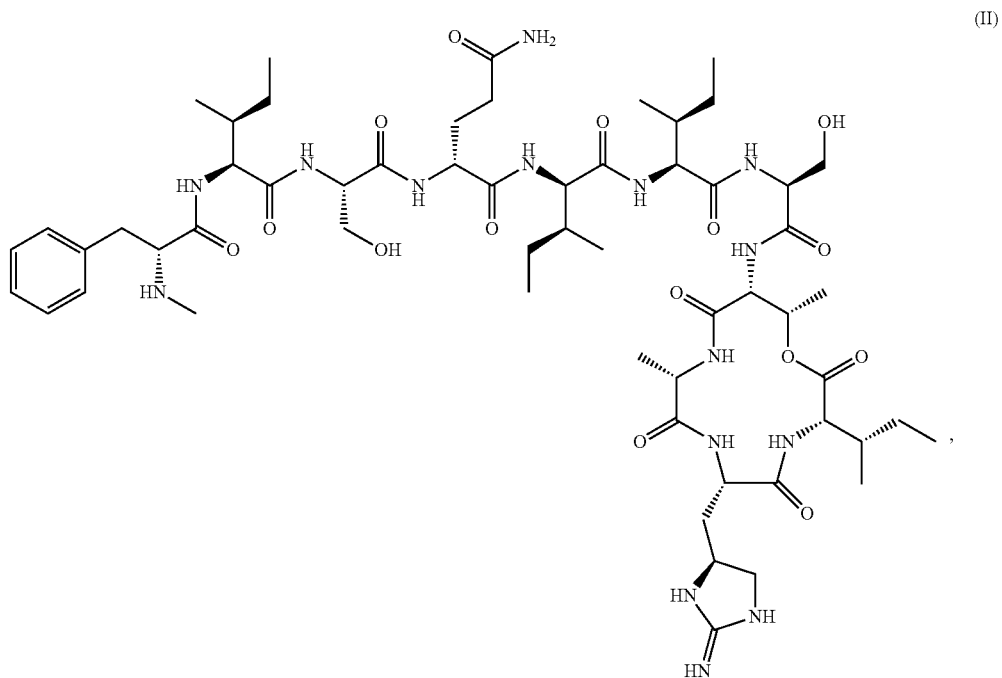 [SMILES: CC[C@H](C)[C@H](NC(=O)[C@@H](Cc1ccccc1)NC)C(=O)N[C@@H](CO)C(=O)N[C@H](CCC(N)=O)C(=O)N[C@@H](C(=O)N[C@H](C(=O)N[C@@H](CO)C(=O)N[C@H]1C(=O)N[C@@H](C)C(=O)N[C@@H](C[C@H]2CNC(=N)N2)C(=O)N[C@@H]([C@@H](C)CC)C(=O)O[C@H]1C)[C@@H](C)CC)[C@@H](C)CC]

(II)

or tautomer or pharmaceutically-acceptable salt thereof.

In some embodiments, the compound of Formula (II) is an isolated natural product of a bacterial species. For example, in some embodiments, the compound of Formula (II) is an isolated natural product of bacterial isolate ISO18629. In some embodiments, the compound of Formula (II) is producible from a bacterial species. For example, in some embodiments, the compound of Formula (II) is producible from bacterial isolate ISO18629.

In some embodiments, the compound of Formula (I) is characterized by at least ten $^{13}$C nuclear magnetic resonance peaks at chemical shifts (+/−0.2 ppm) in DMSO-$d_6$ selected from 36.3 ppm, 36.5 ppm, 36.9 ppm, 37.4 ppm, 52.1 ppm, 52.2 ppm, 52.7 ppm, 53.5 ppm, 55.7 ppm, 56.1 ppm, 56.4 ppm, 56.7 ppm, 57.3 ppm, 57.8 ppm, 57.9 ppm, 61.8 ppm, and 71.1 ppm. In some embodiments, the compound of Formula (I) is characterized by $^{13}$C nuclear magnetic resonance peaks at chemical shifts (+/−0.2 ppm) in DMSO-$d_6$ of 36.3 ppm, 36.5 ppm, 36.9 ppm, 37.4 ppm, 52.1 ppm, 52.2 ppm, 52.7 ppm, 53.5 ppm, 55.7 ppm, 56.1 ppm, 56.4 ppm, 56.7 ppm, 57.3 ppm, 57.8 ppm, 57.9 ppm, 61.8 ppm, and 71.1 ppm.

In yet another embodiment, the present invention relates to a compound of Formula (I) which is characterized by at least one of: a molecular weight of about 1242.47 g/mol; a proton nuclear magnetic resonance spectrum substantially the same as that shown in FIG. 1; a carbon 13 nuclear magnetic resonance spectrum substantially the same as that shown in FIG. 2; a COSY nuclear magnetic resonance spectrum substantially the same as that shown in FIG. 3; a DEPT-135 nuclear magnetic resonance spectrum substantially the same as that shown in FIG. 4; a HSQC nuclear magnetic resonance spectrum substantially the same as that shown in FIG. 5; or a HMBC nuclear magnetic resonance spectrum substantially the same as that shown in FIG. 6. In still another embodiment, the present teachings relate to a compound of Formula (I) which is characterized by: a molecular weight of about 1242.47 g/mol; a proton nuclear magnetic resonance spectrum substantially the same as that shown in FIG. 1; a carbon 13 nuclear magnetic resonance spectrum substantially the same as that shown in FIG. 2; a COSY nuclear magnetic resonance spectrum substantially the same as that shown in FIG. 3; a DEPT-135 nuclear magnetic resonance spectrum substantially the same as that shown in FIG. 4; a HSQC nuclear magnetic resonance spectrum substantially the same as that shown in FIG. 5; and a HMBC nuclear magnetic resonance spectrum substantially the same as that shown in FIG. 6.

In one embodiment, the present invention relates to an isolated compound of Formula (III):

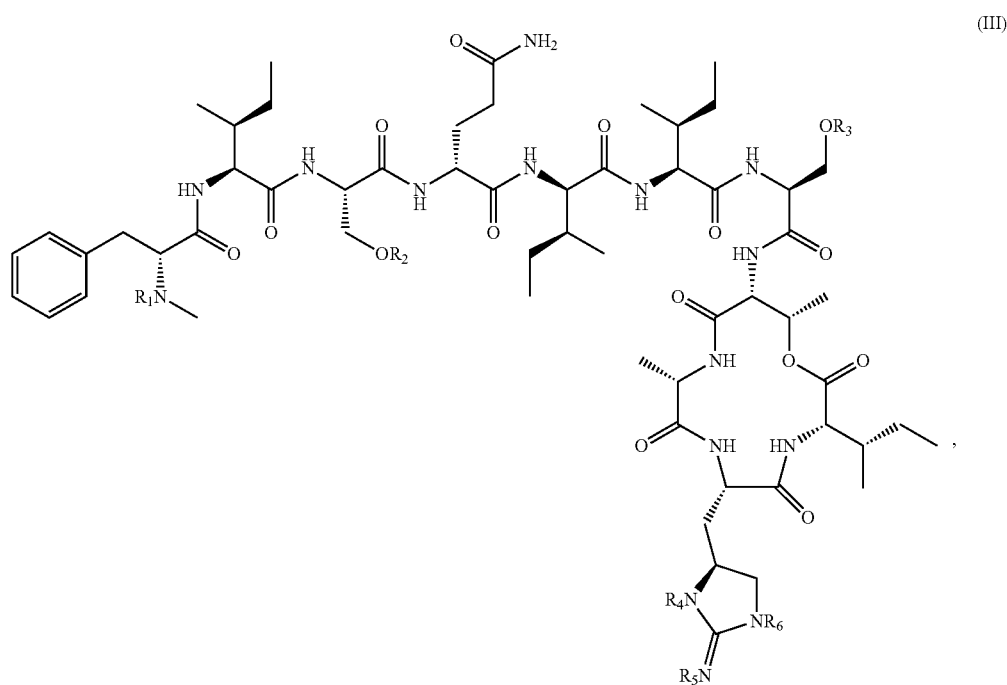

or tautomer or pharmaceutically-acceptable salt thereof.

Each $R_1$-$R_6$ is independently selected from hydrogen, alkyl, alkenyl, alkynyl, cycloalkyl, cycloalkenyl, aryl, C(=O)$R_a$ and S(=O)$_2$$R_b$; each $R_a$ is independently hydrogen, alkyl, alkenyl, alkynyl, cycloalkyl, cycloalkenyl, or aryl; and each $R_b$ is independently alkyl, alkenyl, alkynyl, cycloalkyl, cycloalkenyl, or aryl.

Any carbon or hydrogen may also be replaced with $^{13}$C or $^2$H, respectively.

In one embodiment, the present invention relates to an isolated compound of Formula (IV):

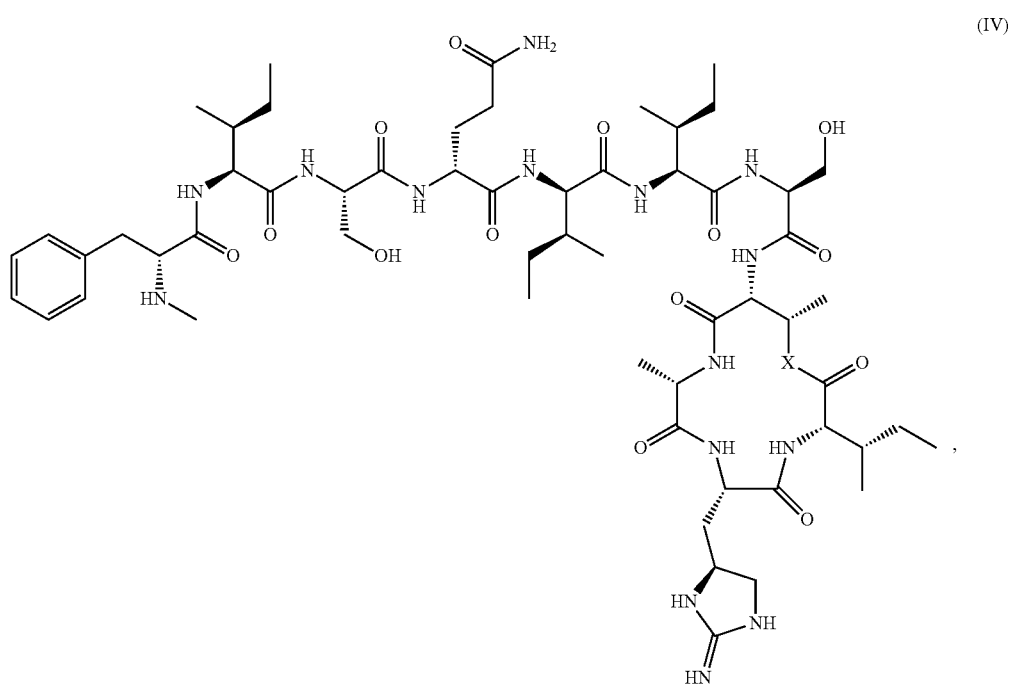

(IV)

wherein X is NH, O or S;
or tautomer or pharmaceutically-acceptable salt thereof.

In yet another embodiment, the present invention relates to a pharmaceutical composition comprising the compounds described herein, e.g., a compound of Formula (I), (II), (III) or (IV), and a pharmaceutically-acceptable excipient, carrier, or diluent. In some embodiments, the pharmaceutical composition comprising any of the compounds described herein may further include an agent selected from the group consisting of an antibiotic, an antifungal agent, an antiviral agent, an anti-protozoan agent, an anthelminthic agent, an anti-neoplastic agent, an immunoregulating agent, an anti-hypercholesterolemia agent and combinations thereof.

In still another embodiment, the present invention relates to a method for producing a compound of Formula (I):

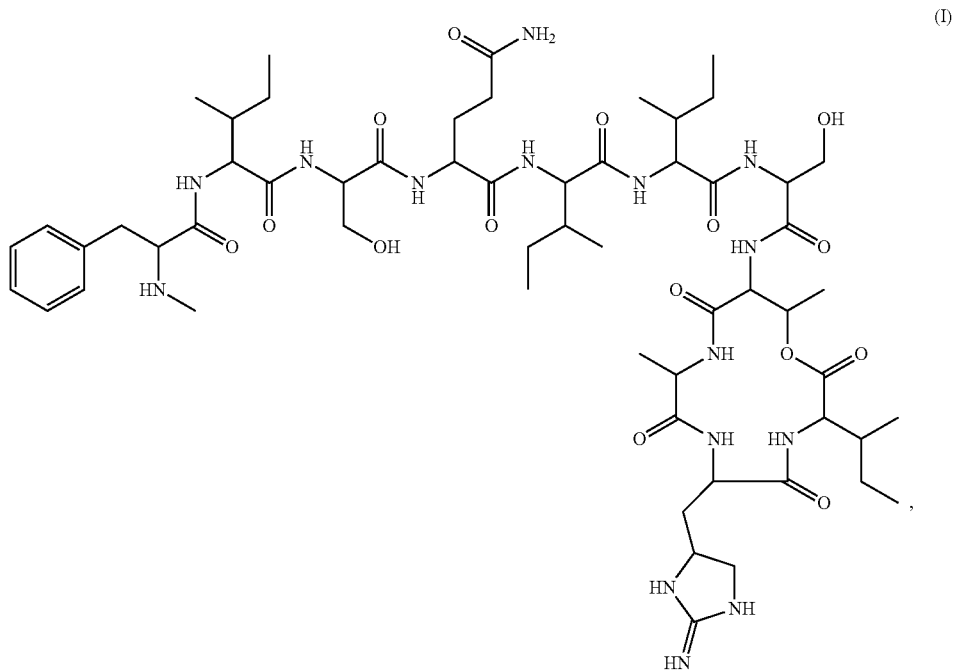 [SMILES: CCC(C)C(NC(=O)C(Cc1ccccc1)NC)C(=O)NC(CO)C(=O)NC(CCC(N)=O)C(=O)NC(C(=O)NC(C(=O)NC(CO)C(=O)NC1C(=O)NC(C)C(=O)NC(CC2CNC(=N)N2)C(=O)NC(C(C)CC)C(=O)OC1C)C(C)CC)C(C)CC]

(I)

or an enantiomer, diastereomer, tautomer, or pharmaceutically-acceptable salt thereof, the method comprising cultivating a bacterial isolate, ISO18629 in a culture comprising assimilable sources of carbon, nitrogen, and inorganic salts under aerobic conditions, thereby producing a compound of Formula (I). In some embodiments, the method further includes isolating the compound of Formula (I) from the culture.

In yet another embodiment, the present invention relates to a compound of Formula (I) prepared according to the method described herein.

In still another embodiment, the present invention relates to a method for producing a compound of Formula (II):

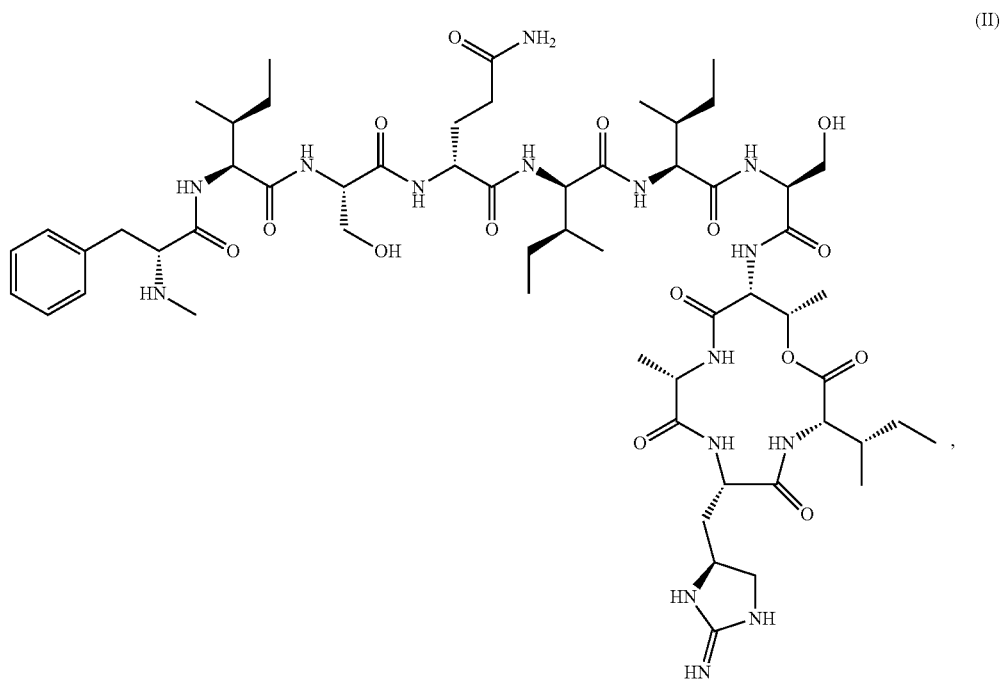 [SMILES: CC[C@H](C)[C@H](NC(=O)[C@@H](Cc1ccccc1)NC)C(=O)N[C@@H](CO)C(=O)N[C@H](CCC(N)=O)C(=O)N[C@@H](C(=O)N[C@H](C(=O)N[C@@H](CO)C(=O)N[C@H]1C(=O)N[C@@H](C)C(=O)N[C@@H](C[C@H]2CNC(=N)N2)C(=O)N[C@@H]([C@@H](C)CC)C(=O)O[C@H]1C)[C@@H](C)CC)[C@@H](C)CC]

(II)

or tautomer or pharmaceutically-acceptable salt thereof, the method comprising cultivating a bacterial isolate, ISO18629 in a culture comprising assimilable sources of carbon, nitrogen, and inorganic salts under aerobic conditions, thereby producing a compound of Formula (II). In some embodiments, the method further includes isolating the compound of Formula (II) from the culture.

In yet another embodiment, the present invention relates to a compound of Formula (II) prepared according to the method described herein.

In still another embodiment, the present invention relates to a method for producing a compound of Formula (III):

carbon, nitrogen, and inorganic salts under aerobic conditions, thereby producing a compound of Formula (III). In some embodiments, $^{13}C$ or $^{2}H$ may be incorporated into the compound of Formula (III) by cultivating a bacterial isolate, ISO18629 in a culture comprising assimilable sources of labeled carbon, nitrogen, and inorganic salts which are labeled with $^{13}C$ and/or $^{2}H$ under aerobic conditions, thereby producing a compound of Formula (III) that contains $^{13}C$ or $^{2}H$. For example, $^{13}C$ and/or $^{2}H$-labeled amino acids may be used. In some embodiments, the method further includes isolating the compound of Formula (III) from the culture.

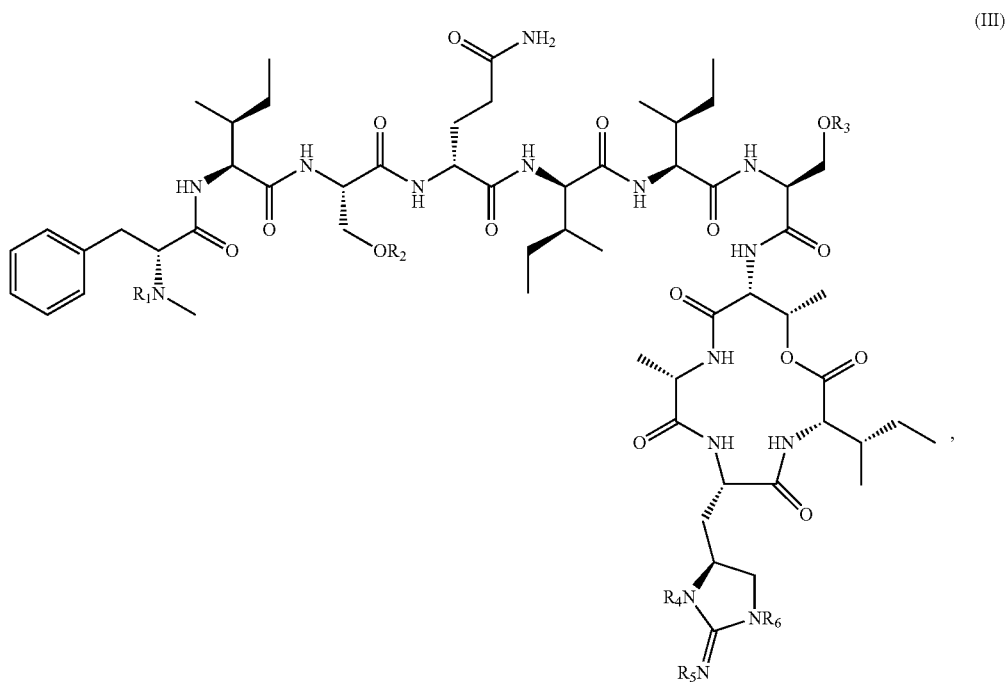

or tautomer or pharmaceutically-acceptable salt thereof, wherein the variables are described above, the method comprising cultivating a bacterial isolate, ISO18629 in a culture comprising assimilable sources of In yet another embodiment, the present invention relates to a compound of Formula (III) prepared according to the method described herein.

In still another embodiment, the present invention relates to a method for producing a compound of Formula (IV):

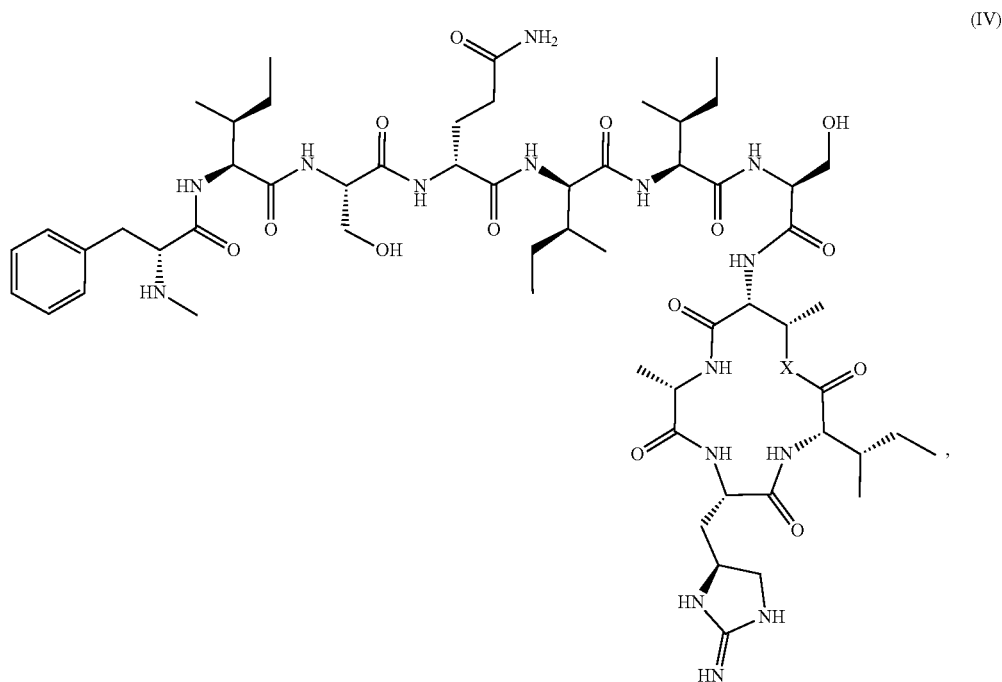

or tautomer or pharmaceutically-acceptable salt thereof, wherein X is NH, O or S;
the method comprising cultivating a bacterial isolate, ISO18629 in a culture comprising assimilable sources of carbon, nitrogen, and inorganic salts under aerobic conditions, thereby producing a compound of Formula (IV). In some embodiments, the method further includes isolating the compound of Formula (IV) from the culture.

In yet another embodiment, the present invention relates to a compound of Formula (IV) prepared according to the method described herein.

In yet another embodiment, the present invention relates to an isolated culture comprising a bacterial species, having the identifying characteristics of an ISO18629.

The present invention also relates to a method of treating a disorder in a subject, e.g., a human, in need thereof. The method includes administering to the subject a therapeutically effective amount of a compound described herein, e.g., a compound of Formula (I), (II), (III) or (IV) thereby treating the disorder in the subject. In some embodiments, the subject is a mammal, a human, an animal or a plant. In a specific embodiment, the subject is a human. In certain embodiments, the disorder is caused by an agent such as, but not limited to, a bacterium, a fungus, a virus, a protozoan, a helminth, a parasite, and combinations thereof.

In a particular embodiment, the agent is a bacterium. In one embodiment, the bacterium is a Gram-positive bacterium. Non-limiting examples of Gram-positive bacteria include *Streptococcus, Staphylococcus, Enterococcus, Corynebacteria, Listeria, Bacillus, Erysipelothrix,* and *Actinomycetes*. In some embodiments, the compounds of Formula (I), (II), (III) or (IV) are used to treat an infection by one or more of: *Helicobacter pylori, Legionella pneumophilia, Mycobacterium tuberculosis, Mycobacterium avium, Mycobacterium intracellulare, Mycobacterium kansaii, Mycobacterium gordonae, Mycobacteria sporozoites, Staphylococcus aureus, Staphylococcus epidermidis, Neisseria gonorrhoeae, Neisseria meningitidis, Listeria monocytogenes, Streptococcus pyogenes* (Group A *Streptococcus*), *Streptococcus agalactiae pyogenes* (Group B *Streptococcus*), *Streptococcus dysgalactia, Streptococcus faecalis, Streptococcus bovis, Streptococcus pneumoniae,* pathogenic *Campylobacter sporozoites, Enterococcus sporozoites, Haemophilus influenzae, Pseudomonas aeruginosa, Bacillus anthracis, Bacillus subtilis, Escherichia coli, Corynebacterium diphtherias, Corynebacterium jeikeium, Corynebacterium sporozoites, Erysipelothrix rhusiopathiae, Clostridium perfringens, Clostridium tetani, Clostridium difficile, Enterobacter aerogenes, Klebsiella pneumoniae, Pasturella multocida, Bacteroides thetaiotamicron, Bacteroides uniformis, Bacteroides vulgatus, Fusobacterium nucleatum, Streptobacillus moniliformis, Leptospira,* and *Actinomyces israelii*. In particular, the Gram positive bacterium is *Bacillus anthracis*.

In another embodiment, the bacterium is a Gram-negative bacterium. Non-limiting examples of Gram-negative bacteria include *Helicobacter pylori, Legionella pneumophilia, Neisseria gonorrhoeae, Neisseria meningitidis,* pathogenic *Campylobacter sporozoites, Haemophilus influenzae, Pseudomonas aeruginosa, Enterobacter aerogenes, Enterobacter cloacae, Klebsiella pneumoniae, Klebsiella oxytoca, Pasteurella multocida, Bacteroides sporozoites, Bacteriodes fragilis, Bacteriodes thetaiotaomicron, Bacteriodes uniformis, Bacteriodes vulgatus Fusobacterium nucleatum, Streptobacillus moniliformis, Leptospira, Escherichia coli, Salmonella enterica, Salmonella salamae, Salmonella arizonae, Salmonella diarizonae, Salmonella houtenae, Salmonella bongori, Salmonella indica, Salmonella Enteritidis, Salmonella typhi,* and *Citrobacter freundii.*

In other embodiments, the depsipeptide compounds described herein may be useful in treating viral disorders. Non-limiting examples of infectious viruses that may be treated by the compounds of Formula (I), (II), (III) or (IV) include: Retroviridae (e.g., human immunodeficiency viruses, such as HIV-1 (also referred to as HTLV-III, LAV or HTLV-III/LAV), or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses, severe acute respiratory syndrome (SARS) virus); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arenaviridae (hemorrhagic fever viruses); Reoviridae (e.g., reoviruses, orbiviurses and rotaviruses); Birnaviridae; Hepadnaviridae (e.g, Hepatitis B virus); Parvoviridae (parvoviruses); Papovaviridae (papilloma viruses, polyoma viruses); Adenoviridae (most adenoviruses); Herpesviridae (e.g., herpes simplex virus (HSV) 1 and 2, varicella zoster virus, cytomegalovirus (CMV), herpes viruses); Poxviridae (e.g., variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parentally transmitted, i.e., Hepatitis C); Norwalk and related viruses, and astroviruses). In specific embodiments, the compounds of Formula (I), (II), (III) or (IV) are used to treat an influenza virus, human immunodeficiency virus, or herpes simplex virus.

In yet other embodiments, the depsipeptide compounds described herein are useful in treating disorders caused by protozoans. Non-limiting examples of protozoa that can be inhibited by the compounds of Formula (I), (II), (III) or (IV) include, but are not limited to, *Trichomonas vaginalis, Giardia lamblia, Entamoeba histolytica, Balantidium coli, Cryptosporidium parvum* and *Isospora belli, Trypansoma cruzi, Trypanosoma gambiense, Leishmania donovani,* and *Naegleria fowleri.*

In certain embodiments, the depsipeptide compounds described herein are useful in treating disorders caused by helminths. Non-limiting examples of helminths that can be inhibited by the compounds of Formula (I), (II), (III) or (IV) include, but are not limited to: *Schistosoma mansoni, Schistosoma cercariae, Schistosoma japonicum, Schistosoma mekongi, Schistosoma hematobium, Ascaris lumbricoides, Strongyloides stercoralis, Echinococcus granulosus, Echinococcus multilocularis, Angiostrongylus cantonensis, Angiostrongylus constaricensis, Fasciolopis buski, Capillaria philippinensis, Paragonimus westermani, Ancylostoma dudodenale, Necator americanus, Trichinella spiralis, Wuchereria bancrofti, Brugia malayi,* and *Brugia timori, Toxocara canis, Toxocara cati, Toxocara vitulorum, Caenorhabiditis elegans,* and *Anisakis* species.

In some embodiments, the depsipeptide compounds described herein are useful in treating disorders caused by parasites. Non-limiting examples of parasites that can be inhibited by the compounds of Formula (I), (II), (III) or (IV) include, but are not limited to, *Plasmodium falciparum, Plasmodium yoelli, Hymenolepis nana, Clonorchis sinensis, Loa boa, Paragonimus westermani, Fasciola hepatica,* and *Toxoplasma gondii.* In specific embodiments, the parasite is a malarial parasite.

In further embodiments, the depsipeptide compounds of Formula (I), (II), (III) or (IV) may be useful to treat disorders caused by fungi. Non-limiting examples of fungi that may be inhibited by the compounds of Formula (I), (II), (III) or (IV) include, but are not limited to, *Cryptococcus neoformans, Histoplasma capsulatum, Coccidioides immitis, Blastomyces dermatitidis, Chlamydia trachomatis, Candida albicans, Candida tropicalis, Candida glabrata, Candida krusei, Candida parapsilosis, Candida dubliniensis, Candida lusitaniae, Epidermophyton floccosum, Microsporum audouinii, Microsporum canis, Microsporum canis* var. *distortum Microsporum cookei, Microsporum equinum, Microsporum ferrugineum, Microsporum fulvum, Microsporum gallinae, Microsporum gypseum, Microsporum nanum, Microsporum persicolor, Trichophyton ajelloi, Trichophyton concentricum, Trichophyton equinum, Trichophyton flavescens, Trichophyton gloriae, Trichophyton megnini, Trichophyton mentagrophytes* var. *erinacei, Trichophyton mentagrophytes* var. *interdigitale, Trichophyton phaseoliforme, Trichophyton rubrum, Trichophyton rubrum* downy strain, *Trichophyton rubrum* granular strain, *Trichophyton schoenleinii, Trichophyton simii, Trichophyton soudanense, Trichophyton terrestre, Trichophyton tonsurans, Trichophyton vanbreuseghemii, Trichophyton verrucosum, Trichophyton violaceum, Trichophyton yaoundei, Aspergillus fumigatus, Aspergillus flavus,* and *Aspergillus clavatus.* In yet another embodiment, the present invention relates to a method of inhibiting the growth of an infectious agent, the method comprising contacting the agent with a compound described herein, e.g., a compound of Formula (I), (II), (III) or (IV), thereby inhibiting the growth of the infectious agent.

In a particular embodiment, the infectious agent is cultured in vitro.

The present invention is further illustrated by the following detailed description and drawings.

DESCRIPTION OF THE FIGURES

The foregoing and other objects of the present invention, the various features thereof, as well as the invention itself may be more fully understood from the following description, when read together with the accompanying drawings in which.

DETAILED DESCRIPTION OF THE INVENTION

Figure 1:
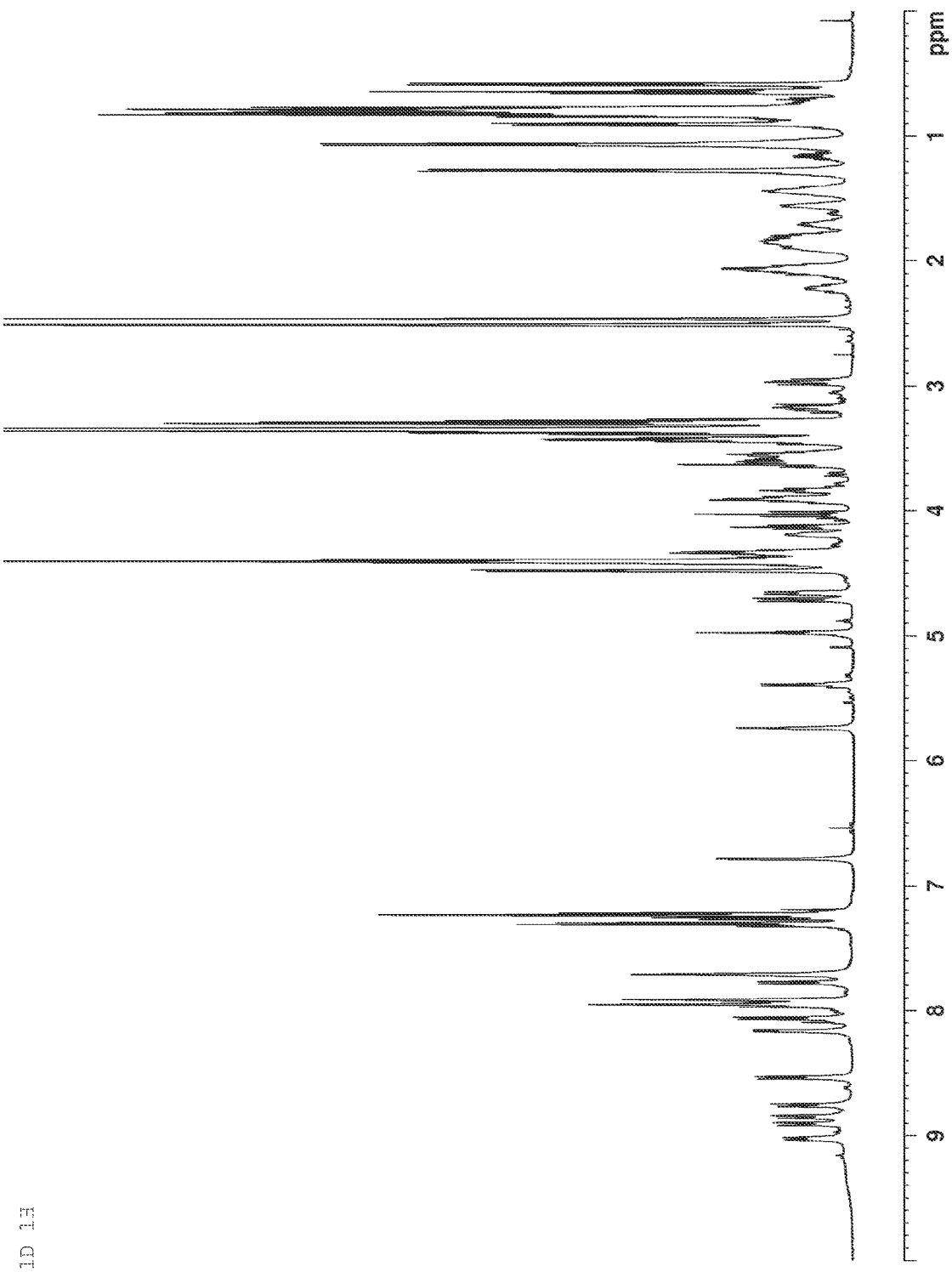
FIG. 1 is a schematic representation of the proton nuclear magnetic resonance spectrum (in DMSO-$d_6$) of a compound isolated from a growing strain of ISO18629.

The present invention relates generally to novel depsipeptides, to processes for the preparation of these novel depsipeptides, to pharmaceutical compositions comprising the novel depsipeptides, and to methods of using the novel depsipeptides to treat or inhibit various disorders, e.g., bacterial infections. The present invention relates to a novel antibiotic that has broad activity against many bacterial pathogens, including strains resistant to other antibiotics, and in particular, Gram-positive pathogens. The compounds disclosed herein have favorable bioavailability and low toxicity.

Definitions

For convenience, certain terms employed in the specification, examples, and appended claims are collected here. Unless defined otherwise, all technical and scientific terms used herein have the same meaning as commonly understood by one of ordinary skill in the art to which this invention belongs. The initial definition provided for a group or term herein applies to that group or term throughout the present specification individually or as part of another group, unless otherwise indicated.

The articles "a" and "an" are used herein to refer to one or to more than one (i.e., to at least one) of the grammatical object of the article. By way of example, "an element" means one element or more than one element.

The term "or" is used herein to mean, and is used interchangeably with, the term "and/or," unless context clearly indicates otherwise.

The term "substantially the same" is used herein to mean that two subjects being compared share at least 90% of a common feature. In certain embodiments, the two subjects share at least 95% of a common feature. In certain other embodiments, the two subjects share at least 99% of a common feature.

The term "isolated" is used herein to refer to compounds of Formula (I), (II), (III) or (IV) being substantially free from other materials associated with it in its natural environment. For example an isolated compound can be substantially free of contaminating materials, such as cellular material, contaminating materials from the cell from which the compound is derived, chemical precursors or other chemicals when chemically synthesized. Substantially free of other materials refers generally to, for example, less than about 30%, or 20%, or 15%, or 10%, or 5%, or 2% (by dry weight) impurities. In some embodiments, the isolated compounds are substantially pure. In some embodiments, the preparation of a compound having less than about 10% (by dry weight) of contaminating materials from the cell, or of chemical precursors is considered to be substantially pure. In other embodiments, the preparation of a compound having less than about 5%, about 4%, about 3%, about 2%, about 1% (by dry weight) of contaminating materials from the cell, or of chemical precursors is considered to be substantially pure.

Unless otherwise indicated, any heteroatom with unsatisfied valences is assumed to have hydrogen atoms sufficient to satisfy the valences.

The term "heating" includes, but not limited to, warming by conventional heating (e.g., electric heating, steam heating, gas heating, etc.) as well as microwave heating.

The term "pharmaceutically-acceptable excipient, carrier, or diluent" as used herein means a pharmaceutically-acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to a patient.

The term "treating" with regard to a subject, refers to improving at least one symptom of the subject's disorder. Treating can be curing the disorder or condition, or improving it.

The term "disorder" is used herein to mean, and is used interchangeably with, the terms disease, condition, or illness, unless the context clearly indicates otherwise.

The term "microbe" is used herein to mean an organism such as a bacterium, a virus, a protozoan, or a fungus, especially one that transmits disease.

The phrase "pharmaceutically acceptable" is employed herein to refer to those compounds, materials, compositions, and/or dosage forms which are, within the scope of sound medical judgment, suitable for use in contact with the tissues of human beings, animals and plants without excessive toxicity, irritation, allergic response, or other problem or complication, commensurate with a reasonable benefit/risk ratio.

Throughout the specification, groups and substituents thereof may be chosen to provide stable moieties and compounds.

Compounds of the Invention

In one embodiment, the present invention relates to isolated compounds of Formula (I):

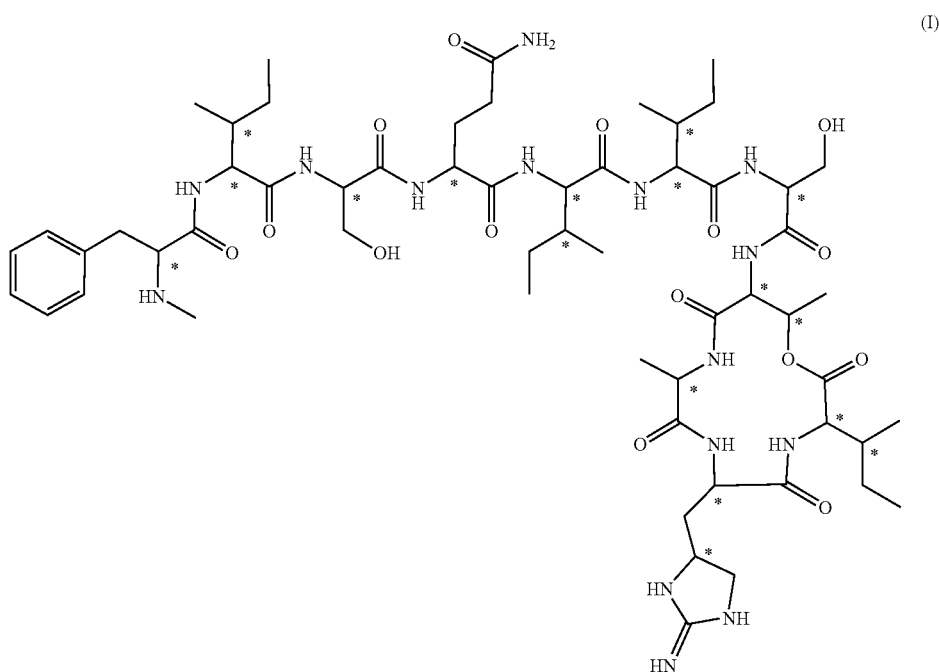 [SMILES: CCC(C)C(NC(=O)C(Cc1ccccc1)NC)C(=O)NC(CO)C(=O)NC(CCC(N)=O)C(=O)NC(C(=O)NC(C(=O)NC(CO)C(=O)NC1C(=O)NC(C)C(=O)NC(CC2CNC(=N)N2)C(=O)NC(C(C)CC)C(=O)OC1C)C(C)CC)C(C)CC]

and enantiomers, diastereomers, tautomers, or pharmaceutically-acceptable salts thereof, wherein each stereocenter (indicated with an "*") can be either the R or S configuration. Accordingly, when the phrase "a compound of Formula (I)" is used herein, it is meant to include enantiomers, diastereomers, tautomers, and pharmaceutically-acceptable salts thereof. Depsipeptide compounds of the present invention, and salts thereof, may exist in their tautomeric form (for example, as an amide or guanidine). All such tautomeric forms are contemplated herein as part of the present invention. A compound of Formula (I), e.g., a compound isolated from bacterial isolate ISO18629, may also be referred to as "NOVO26". In some embodiments, the present teachings relate to a mixture of stereoisomers. In other embodiments, the present teachings specifically relate to a single stereoisomer of a compound of Formula (I).

In a particular embodiment, the present invention specifically relates to a single stereoisomer of a compound of Formula (I) which is a compound of Formula (II):

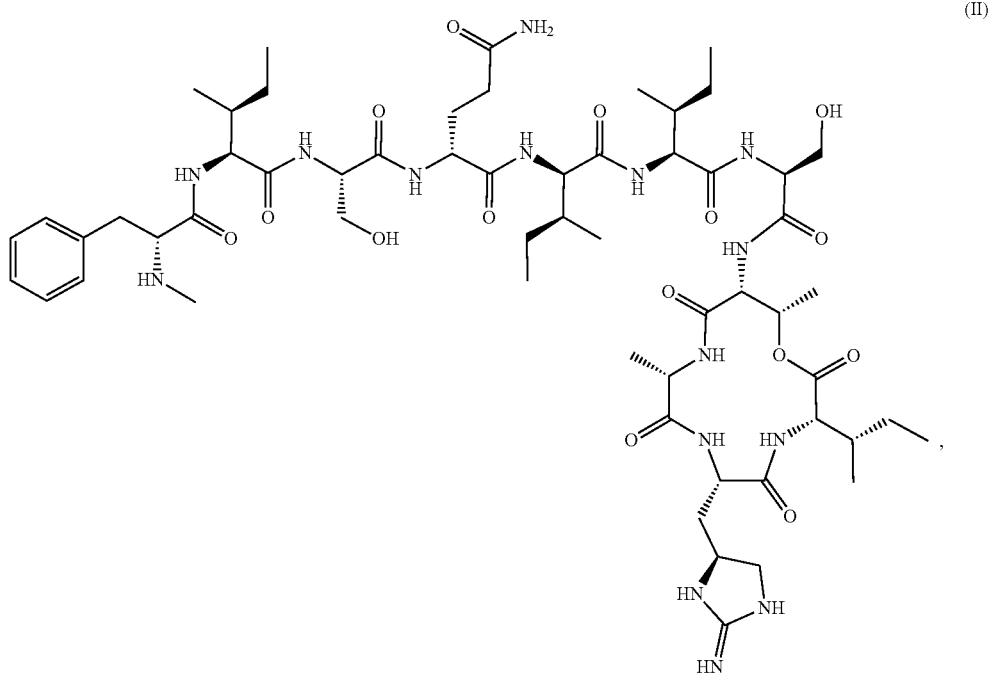 [SMILES: CC[C@H](C)[C@H](NC(=O)[C@@H](Cc1ccccc1)NC)C(=O)N[C@@H](CO)C(=O)N[C@H](CCC(N)=O)C(=O)N[C@@H](C(=O)N[C@H](C(=O)N[C@@H](CO)C(=O)N[C@H]1C(=O)N[C@@H](C)C(=O)N[C@@H](C[C@H]2CNC(=N)N2)C(=O)N[C@@H]([C@@H](C)CC)C(=O)O[C@H]1C)[C@@H](C)CC)[C@@H](C)CC]

(II)

or tautomer or pharmaceutically-acceptable salt thereof.

All stereoisomers of the depsipeptide compounds of the present invention (for example, those which may exist due to asymmetric carbons on various substituents), including enantiomeric forms and diastereomeric forms, are contemplated within the scope of this present invention. In one embodiment, compounds of Formula (I) are mixtures. Alternatively, however, compounds of Formula (I) are single stereoisomers substantially free of other stereoisomers (e.g., as a pure or substantially pure optical isomer having a specified activity). In a particular embodiment, the compound of Formula (I) is a single stereoisomer represented by Formula (II). In some embodiments, the present invention relates to a single stereoisomer in the presence of less than about 10% (by dry weight) other isomers. In some embodiments, the present invention relates to a single stereoisomer in the presence of less than about 5% (by dry weight) other isomers. In some embodiments, the present invention relates to a single stereoisomer in the presence of less than about 2% (by dry weight) other isomers. In some embodiments, the present invention relates to a single stereoisomer in the presence of less than about 1% (by dry weight) other isomers. In some embodiments, the present invention relates to a single stereoisomer in the presence of about 5% (by dry weight) to about 10% (by dry weight) other isomers. In some embodiments, the present invention relates to a single stereoisomer in the presence of about 1% (by dry weight) to about 5% (by dry weight) other isomers. In some embodiments, the present invention relates to a single stereoisomer in the presence of about 1% (by dry weight) to about 10% (by dry weight) other isomers. In some embodiments, the present invention relates to a single stereoisomer in the presence of about 5% (by dry weight) to about 10% (by dry weight) other isomers. Non-related compounds make up less than 2% (by dry weight). In other embodiments, the present teachings are directed to mixtures of stereoisomers. The chiral centers of the compounds of Formula (I) may have the S or R configuration as defined by the IUPAC 1974 Recommendations. The stereoisomeric forms can be resolved by physical methods, such as, for example, fractional crystallization, separation or crystallization of diastereomeric derivatives or separation by chiral column chromatography. The individual optical isomers can be obtained from a mixture of stereoisomers by any suitable method, including without limitation, conventional methods, such as, for example, salt formation with an optically active acid followed by crystallization.

Depsipeptide compounds of the present invention may be, subsequent to their preparation, e.g., isolated and purified to obtain a composition containing an amount by weight equal to or greater than 90% (by dry weight), which is then used or formulated as described herein. Depsipeptide compounds of the present invention may be, subsequent to their preparation, e.g., isolated and purified to obtain a composition containing an amount by weight equal to or greater than 95% (by dry weight), which is then used or formulated as described herein. Depsipeptide compounds of the present invention may be, subsequent to their preparation, e.g., isolated and purified to obtain a composition containing an amount by weight of about 90% (by dry weight) to about 95% (by dry weight), which is then used or formulated as described herein. Depsipeptide compounds of the present invention may be, subsequent to their preparation, e.g., isolated and purified to obtain a composition containing an amount by weight of about 85% (by dry weight) to about 95% (by dry weight), which is then used or formulated as described herein. Depsipeptide compounds of the present invention may be, subsequent to their preparation, e.g., isolated and purified to obtain a composition containing an amount by weight of about 95% (by dry weight) to about 99% (by dry weight), which is then used or formulated as described herein.

All configurational isomers of the compounds of the present invention are contemplated, either in admixture or in pure or substantially pure form.

In one embodiment, the present invention relates to an isolated compound of Formula (III):

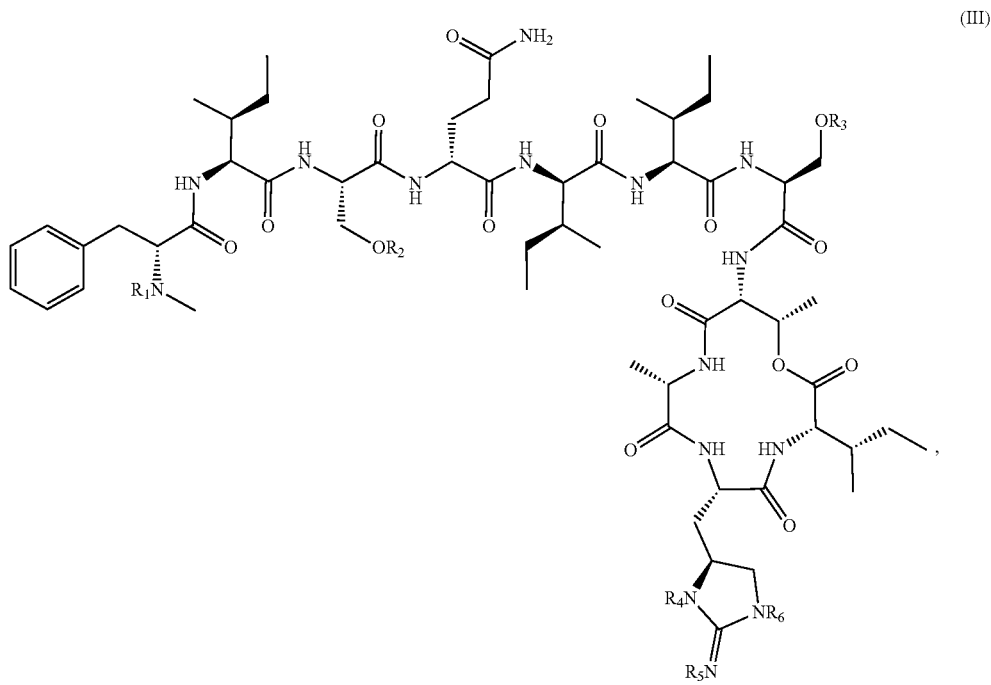

or tautomer or pharmaceutically-acceptable salt thereof.

Each $R_1$-$R_6$ is independently selected from hydrogen, alkyl, alkenyl, alkynyl, cycloalkyl, cycloalkenyl, aryl, C(=O)$R_a$ and S(=O)$_2 R_b$; each $R_a$ is independently hydrogen, alkyl, alkenyl, alkynyl, cycloalkyl, cycloalkenyl, or aryl; and each $R_b$ is independently alkyl, alkenyl, alkynyl, cycloalkyl, cycloalkenyl, or aryl. Any carbon or hydrogen may also be replaced with $^{13}$C or $^2$H, respectively. In one embodiment, the present invention relates to an isolated compound of Formula (III), or an enantiomer, diastereomer, tautomer, or pharmaceutically-acceptable salt thereof.

The terms "alkyl" refers to a straight or branched chain alkane (hydrocarbon) radical containing from 1 to 12 carbon atoms, e.g., 1 to 6 carbon atoms. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like.

The term "alkenyl" refers to a straight or branched chain hydrocarbon radical containing from 2 to 12 carbon atoms and at least one carbon-carbon double bond. Exemplary such groups include ethenyl or allyl.

The term "alkynyl" refers to a straight or branched chain hydrocarbon radical containing from 2 to 12 carbon atoms and at least one carbon to carbon triple bond. Exemplary such groups include ethynyl.

The term "cycloalkyl" refers to a fully saturated cyclic hydrocarbon group containing from 1 to 4 rings and 3 to 8 carbons per ring. Exemplary such groups include cyclopropyl, cyclobutyl, cyclopentyl, cyclohexyl, cycloheptyl, etc.

The term "cycloalkenyl" refers to a partially unsaturated cyclic hydrocarbon group containing 1 to 4 rings and 3 to 8 carbons per ring. Exemplary such groups include cyclobutenyl, cyclopentenyl, cyclohexenyl, etc.

The term "aryl" refers to cyclic, aromatic hydrocarbon groups that have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like).

In one embodiment, the present invention relates to an isolated compound of Formula (IV):

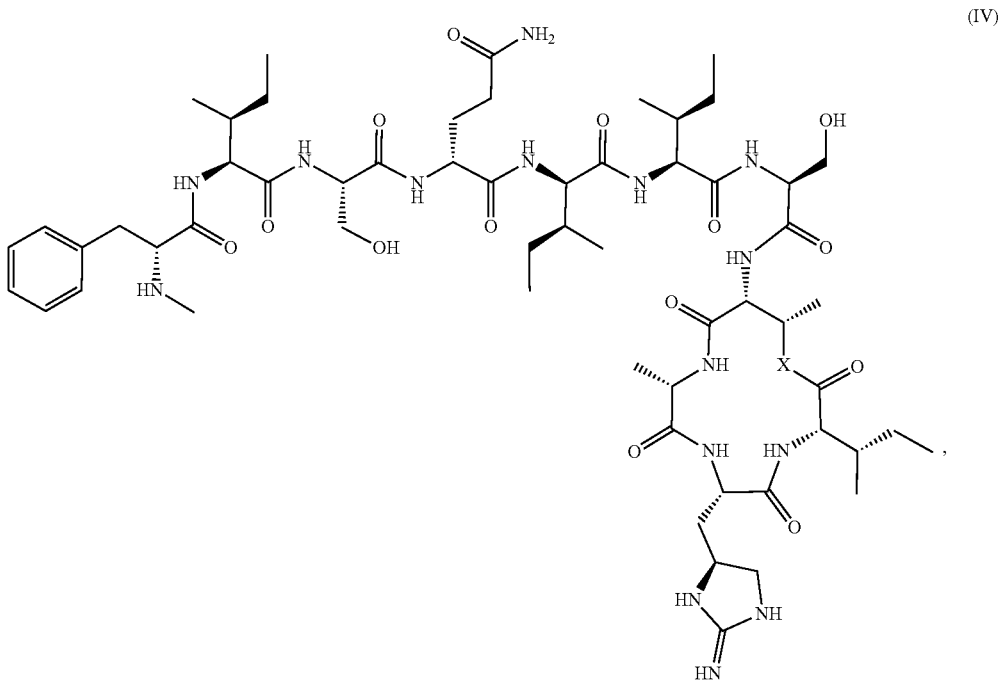

(IV)

wherein X is NH, O or S;
or tautomer or pharmaceutically-acceptable salt thereof. In a specific embodiment, X is NH. Alternatively, X is O. Alternatively, X is S. In one embodiment, the present invention relates to an isolated compound of Formula (IV), or an enantiomer, diastereomer, tautomer, or pharmaceutically-acceptable salt thereof.

In some embodiments, the compound of Formula (I), (II), (III) or (IV) is a natural product of a bacterial species. In some embodiments, the compound of Formula (I), (II), (III) or (IV) is a natural product isolated from a bacterial species. In some embodiments, the compound of Formula (I), (II), (III) or (IV) is a natural product of bacterial isolate ISO18629. For example, in some embodiments, the compound of Formula (I), (II), (III) or (IV) is derived from bacteria cultures of bacterial isolate ISO18629. In some embodiments, the compound of Formula (I), (II), (III) or (IV) is a natural product isolated from bacterial isolate ISO18629.

In some embodiments, the compound of Formula (I) is characterized by at least five $^{13}$C nuclear magnetic resonance peaks at chemical shifts (+/−0.2 ppm) in DMSO-$d_6$ selected from 36.3 ppm, 36.5 ppm, 36.9 ppm, 37.4 ppm, 52.1 ppm, 52.2 ppm, 52.7 ppm, 53.5 ppm, 55.7 ppm, 56.1 ppm, 56.4 ppm, 56.7 ppm, 57.3 ppm, 57.8 ppm, 57.9 ppm, 61.8 ppm, and 71.1 ppm. In some embodiments, the compound of Formula (I) is characterized by at least seven $^{13}$C nuclear magnetic resonance peaks at chemical shifts (+/−0.2 ppm) in DMSO-$d_6$ selected from 36.3 ppm, 36.5 ppm, 36.9 ppm, 37.4 ppm, 52.1 ppm, 52.2 ppm, 52.7 ppm, 53.5 ppm, 55.7 ppm, 56.1 ppm, 56.4 ppm, 56.7 ppm, 57.3 ppm, 57.8 ppm, 57.9 ppm, 61.8 ppm, and 71.1 ppm. In some embodiments, the compound of Formula (I) is characterized by at least ten $^{13}$C nuclear magnetic resonance peaks at chemical shifts (+/−0.2 ppm) in DMSO-$d_6$ selected from 36.3 ppm, 36.5 ppm, 36.9 ppm, 37.4 ppm, 52.1 ppm, 52.2 ppm, 52.7 ppm, 53.5 ppm, 55.7 ppm, 56.1 ppm, 56.4 ppm, 56.7 ppm, 57.3 ppm, 57.8 ppm, 57.9 ppm, 61.8 ppm, and 71.1 ppm. In some embodiments, the compound of Formula (I) is characterized by at least twelve $^{13}$C nuclear magnetic resonance peaks at chemical shifts (+/−0.2 ppm) in DMSO-$d_6$ selected from 36.3 ppm, 36.5 ppm, 36.9 ppm, 37.4 ppm, 52.1 ppm, 52.2 ppm, 52.7 ppm, 53.5 ppm, 55.7 ppm, 56.1 ppm, 56.4 ppm, 56.7 ppm, 57.3 ppm, 57.8 ppm, 57.9 ppm, 61.8 ppm, and 71.1 ppm. In some embodiments, the compound of Formula (I) is characterized by $^{13}$C nuclear magnetic resonance peaks at chemical shifts (+/−0.2 ppm) in DMSO-$d_6$ of 36.3 ppm, 36.5 ppm, 36.9 ppm, 37.4 ppm, 52.1 ppm, 52.2 ppm, 52.7 ppm, 53.5 ppm, 55.7 ppm, 56.1 ppm, 56.4 ppm, 56.7 ppm, 57.3 ppm, 57.8 ppm, 57.9 ppm, 61.8 ppm, and 71.1 ppm. In certain embodiments, the chemical shifts are reported from nuclear magnetic resonance spectra obtained using a 500 MHz magnet. Chemical shifts are reported herein to within an error of +/−0.2 ppm.

Figure 2:
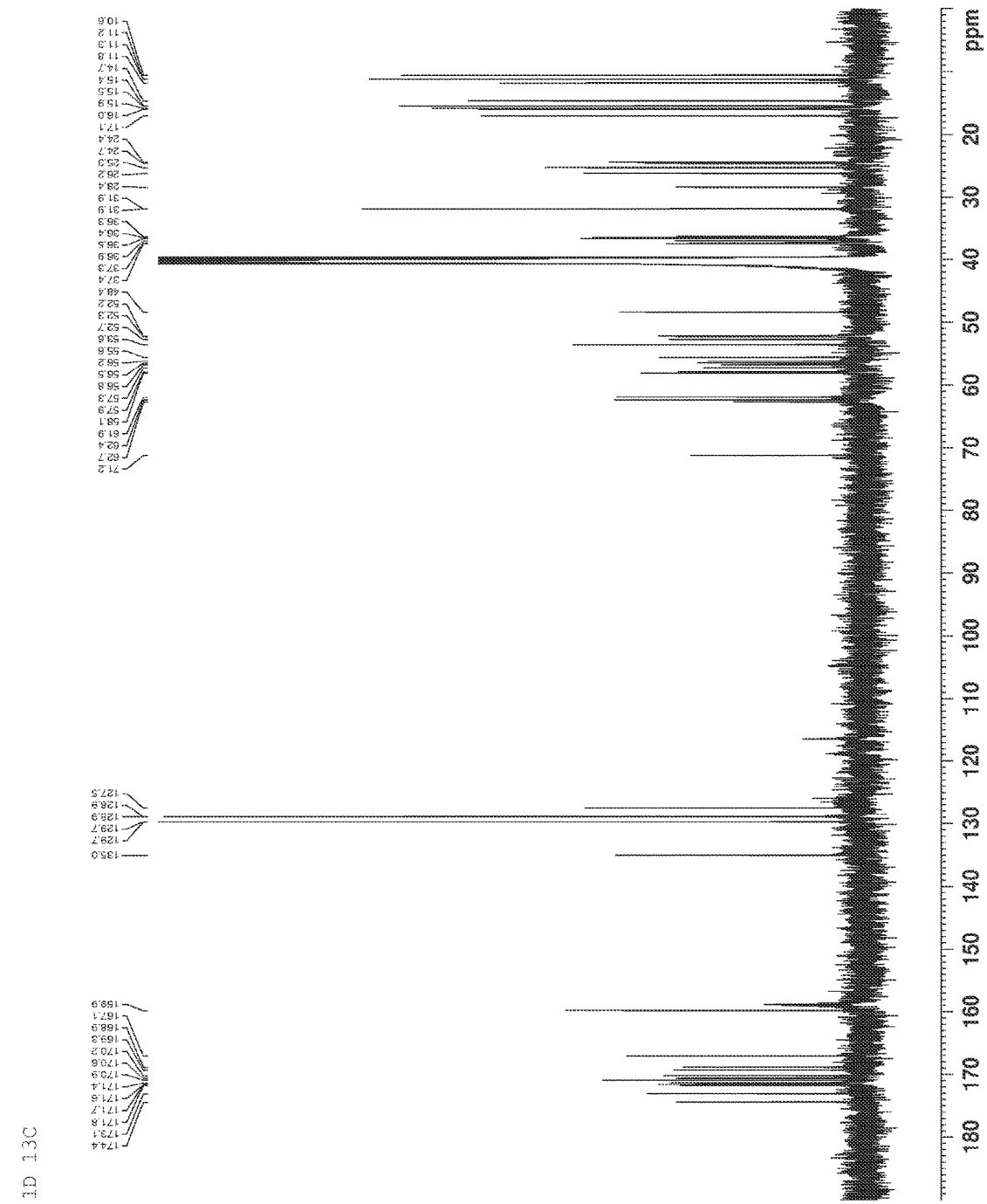
FIG. 2 is a schematic representation of the carbon 13 nuclear magnetic resonance spectrum (in DMSO-$d_6$) of a compound isolated from a growing strain of ISO18629.
Figure 3:
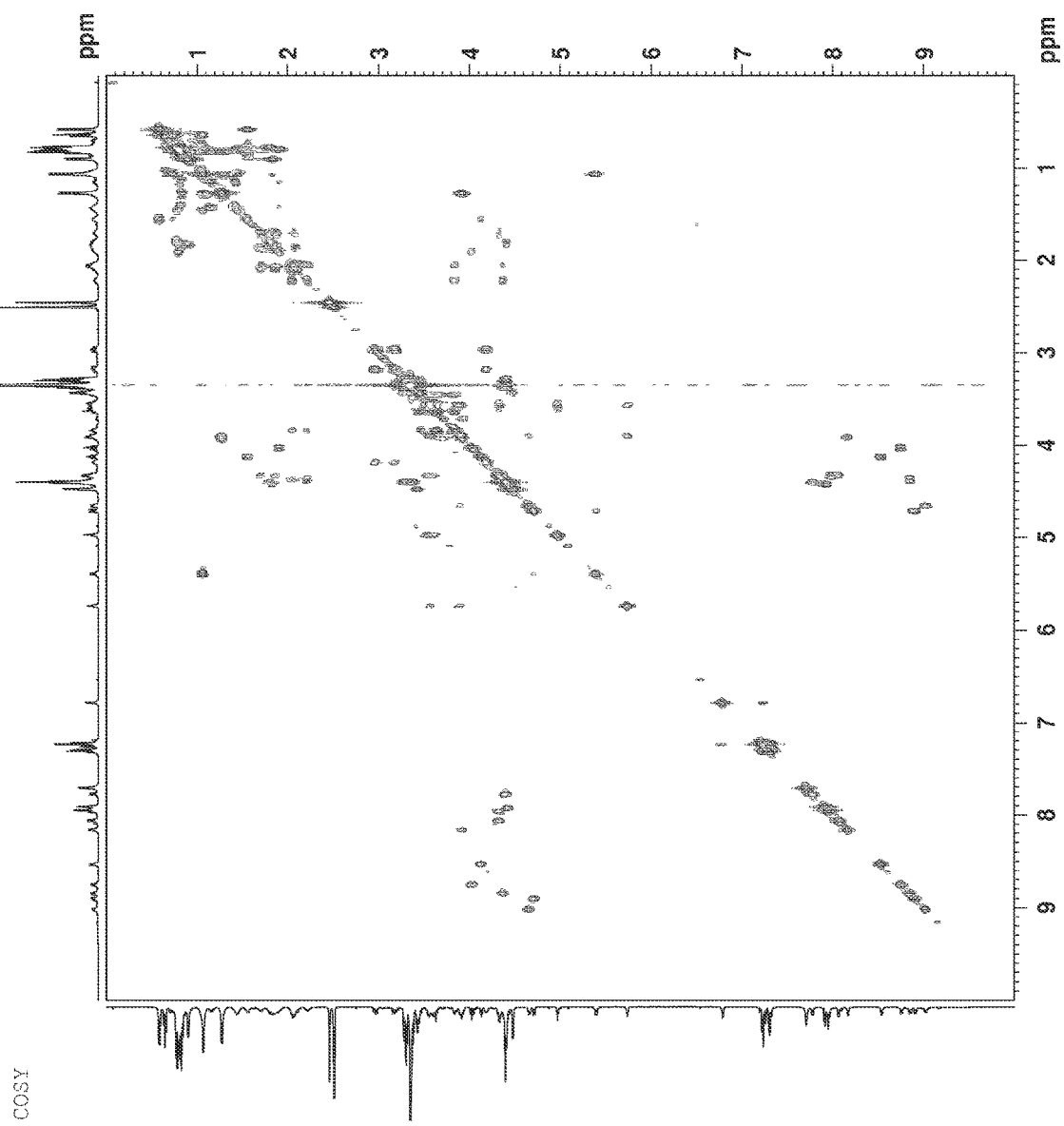
FIG. 3 is a schematic representation of the COSY nuclear magnetic resonance spectrum (in DMSO-$d_6$) of a compound isolated from a growing strain of ISO18629.
Figure 4:
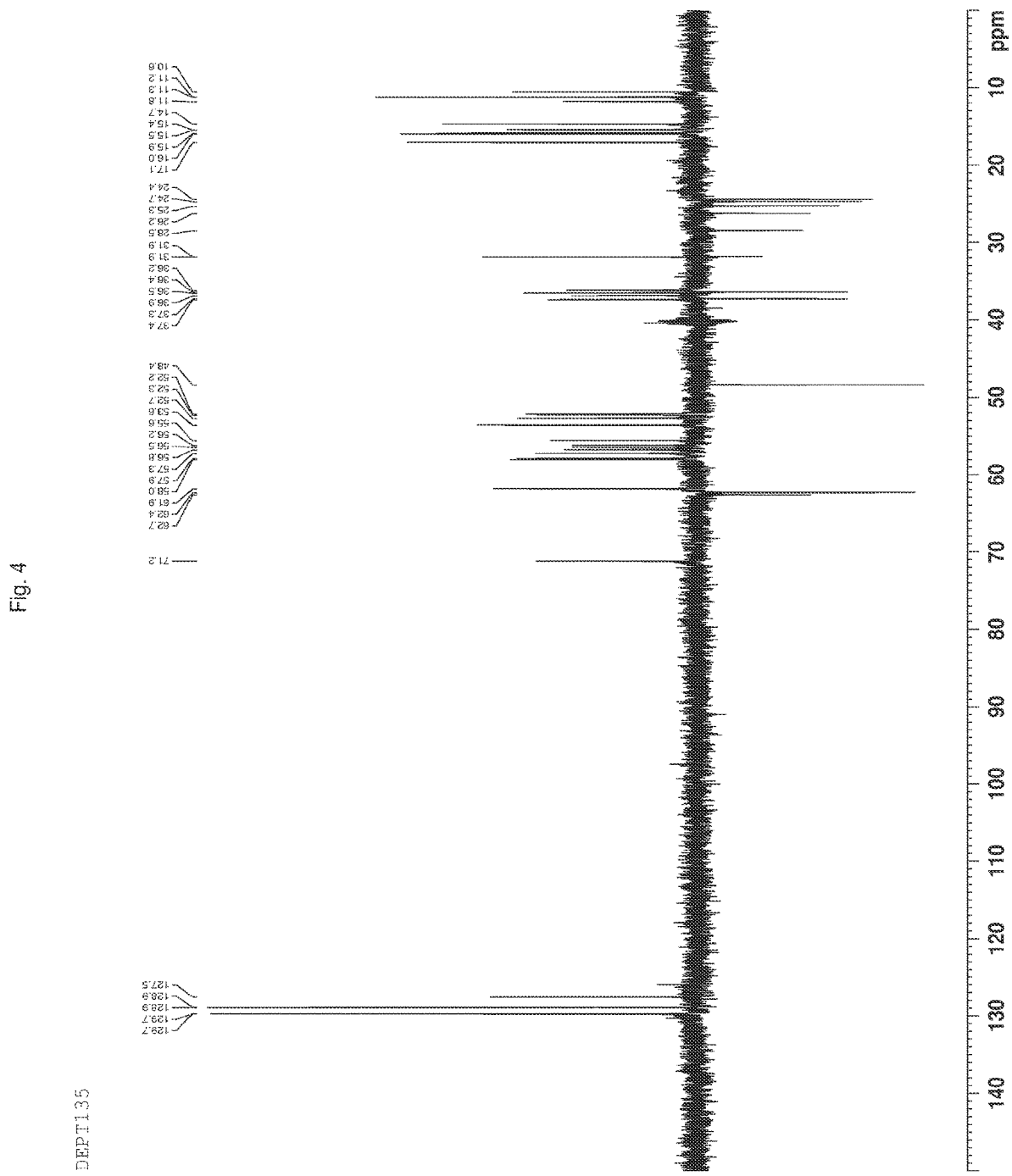
FIG. 4 is a schematic representation of the DEPT-135 nuclear magnetic resonance spectrum (in DMSO-$d_6$) of a compound isolated from a growing strain of ISO18629.
Figure 5:
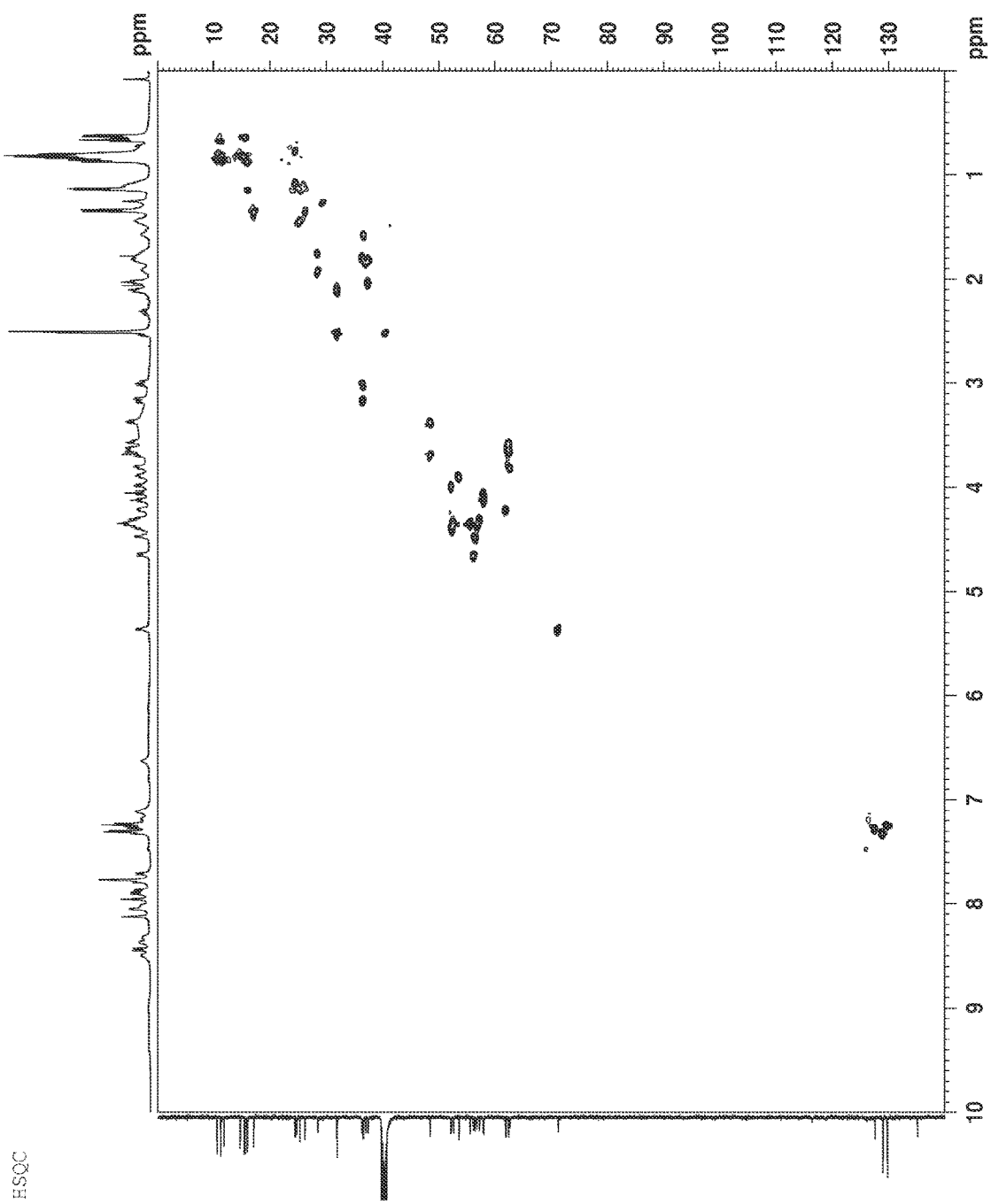
FIG. 5 is a schematic representation of the HSQC nuclear magnetic resonance spectrum (in DMSO-$d_6$) of a compound isolated from a growing strain of ISO18629.
Figure 6:
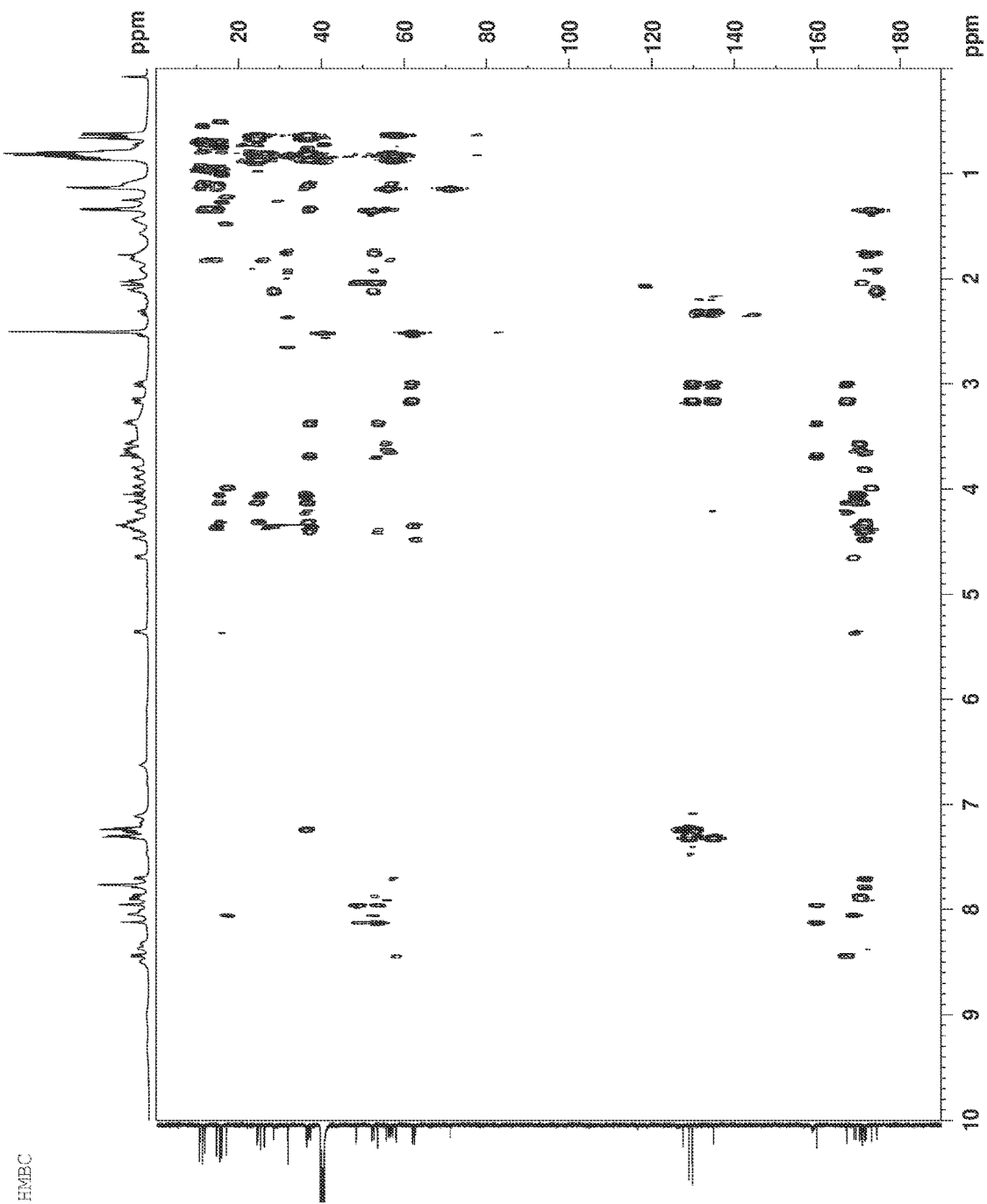
FIG. 6 is a schematic representation of the HMBC nuclear magnetic resonance spectrum (in DMSO-$d_6$) of a compound isolated from a growing strain of ISO18629.

In a further embodiment, the present invention relates to a compound of Formula (I), characterized by at least one of: a molecular weight of about 1242.47 g/mol, a proton nuclear magnetic resonance spectrum substantially the same as that shown in FIG. 1, a $^{13}$C nuclear magnetic resonance spectrum substantially the same as that shown in FIG. 2, a COSY nuclear magnetic resonance spectrum substantially the same as that shown in FIG. 3, a DEPT-135 nuclear magnetic resonance spectrum substantially the same as that shown in FIG. 4, a HSQC nuclear magnetic resonance spectrum substantially the same as that shown in FIG. 5, or a HMBC nuclear magnetic resonance spectrum substantially the same as that shown in FIG. 6. In another embodiment, the present invention relates to a compound of Formula (I), characterized by at least two, at least three, at least four, at least five or at least six of the above characteristics. In still a further embodiment, the present invention relates to a compound of Formula (I), characterized by: a molecular weight of about 1242.47 g/mol, a proton nuclear magnetic resonance spectrum substantially the same as that shown in FIG. 1, a $^{13}$C nuclear magnetic resonance spectrum substantially the same as that shown in FIG. 2, a COSY nuclear magnetic resonance spectrum substantially the same as that shown in FIG. 3, a DEPT-135 nuclear magnetic resonance spectrum substantially the same as that shown in FIG. 4, a HSQC nuclear magnetic resonance spectrum substantially the same as that shown in FIG. 5, and a HMBC nuclear magnetic resonance spectrum substantially the same as that shown in FIG. 6.

In some embodiments, the present invention relates to an isolated natural product of bacterial isolate ISO18629 characterized by $^{13}$C nuclear magnetic resonance peaks at chemical shifts (+/−0.2 ppm) in DMSO-d$_6$ of 36.3 ppm, 36.5 ppm, 36.9 ppm, 37.4 ppm, 52.1 ppm, 52.2 ppm, 52.7 ppm, 53.5 ppm, 55.7 ppm, 56.1 ppm, 56.4 ppm, 56.7 ppm, 57.3 ppm, 57.8 ppm, 57.9 ppm, 61.8 ppm, and 71.1 ppm. In certain embodiments, the present invention relates to an isolated natural product of bacterial isolate ISO18629 characterized by: a molecular weight of about 1242.47 g/mol, a proton nuclear magnetic resonance spectrum substantially the same as that shown in FIG. 1, a $^{13}$C nuclear magnetic resonance spectrum substantially the same as that shown in FIG. 2, a COSY nuclear magnetic resonance spectrum substantially the same as that shown in FIG. 3, a DEPT-135 nuclear magnetic resonance spectrum substantially the same as that shown in FIG. 4, a HSQC nuclear magnetic resonance spectrum substantially the same as that shown in FIG. 5, and/or a HMBC nuclear magnetic resonance spectrum substantially the same as that shown in FIG. 6.

In another embodiment, the present invention relates to a pharmaceutical composition comprising a compound of the invention described herein and a pharmaceutically-acceptable excipient, carrier, or diluent. In certain embodiments, the composition further includes an agent selected from an antibiotic, an antifungal agent, an antiviral agent, an antiprotozoan agent, an anthelminthic agent, an anti-neoplastic agent, an immunoregulating agent, an anti-hypercholesterolemia agent and combinations thereof.

The depsipeptide compounds of the present invention may form salts which are also within the scope of this present invention. Reference to a compound of the present invention herein is understood to include reference to salts thereof, unless otherwise indicated. The term "salt(s)", as employed herein, denotes acidic salts formed with inorganic and/or organic acids. Pharmaceutically acceptable (i.e., non-toxic, physiologically acceptable) salts are preferred, although other salts are also useful, e.g., in isolation or purification steps which may be employed during preparation. Salts of the compounds of the present invention may be formed, for example, by reacting a compound of Formula (I), (II), (III) or (IV) with an amount of acid, such as an equivalent amount, in a medium such as one in which the salt precipitates or in an aqueous or aqueous and organic medium followed by lyophilization.

The depsipeptide compounds of the present invention which contain a basic moiety, such as but not limited to an amine or a guanidine, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemi sulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

Methods of Preparation of the Compounds of the Invention

In yet another embodiment, the present invention relates to a method for producing a compound of Formula (I):

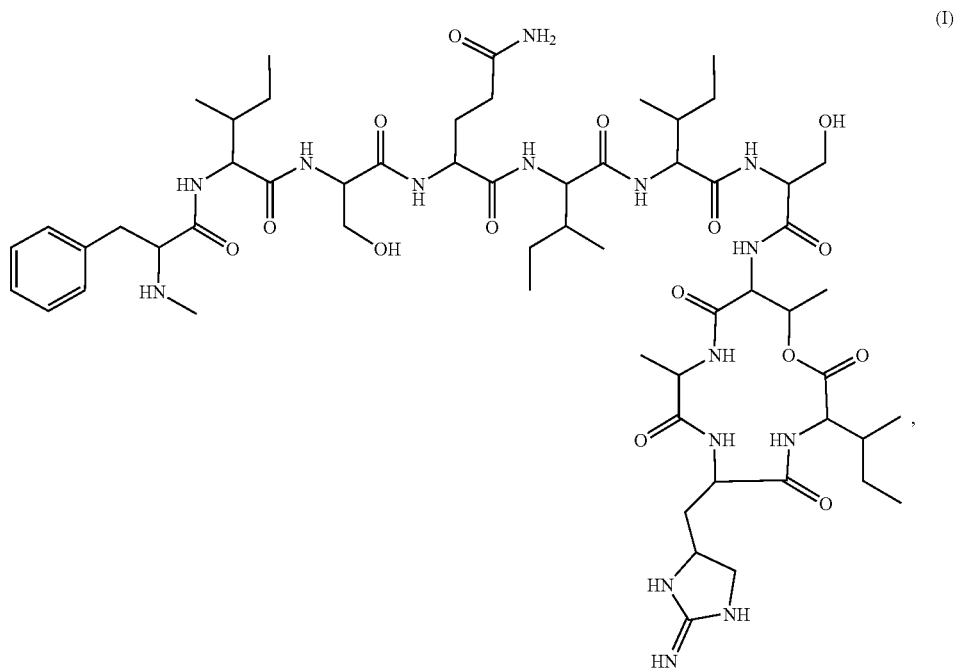 [SMILES: CCC(C)C(NC(=O)C(Cc1ccccc1)NC)C(=O)NC(CO)C(=O)NC(CCC(N)=O)C(=O)NC(C(=O)NC(C(=O)NC(CO)C(=O)NC1C(=O)NC(C)C(=O)NC(CC2CNC(=N)N2)C(=O)NC(C(C)CC)C(=O)OC1C)C(C)CC)C(C)CC]

(I)

or an enantiomer, diastereomer, tautomer, or pharmaceutically-acceptable salt thereof.

In still another embodiment, the present invention relates to a method for producing a compound of Formula (II):

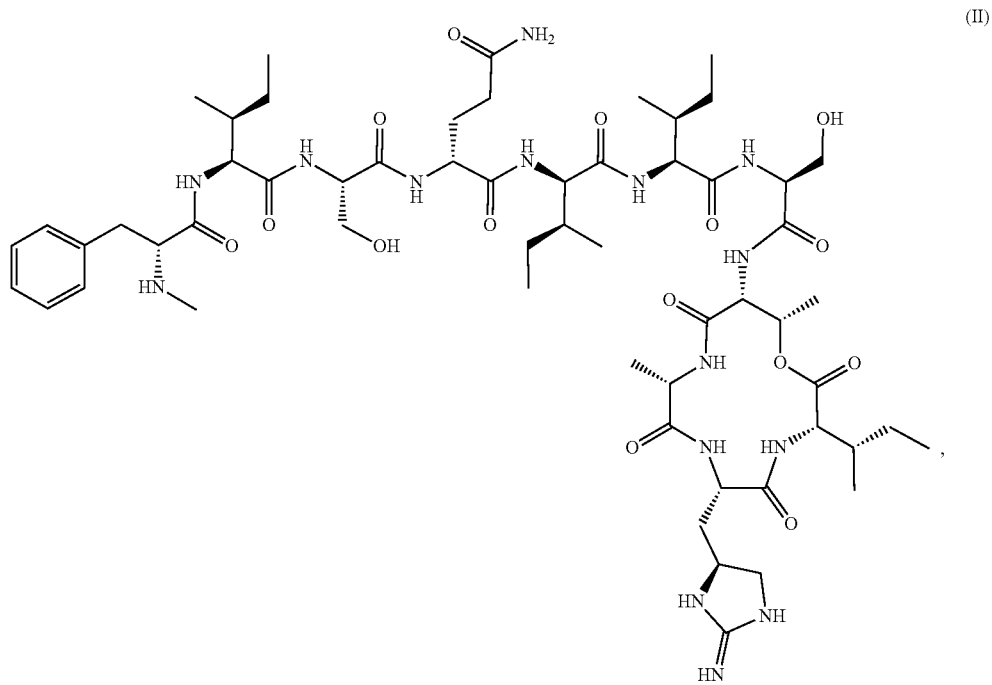 [SMILES: CC[C@H](C)[C@H](NC(=O)[C@@H](Cc1ccccc1)NC)C(=O)N[C@@H](CO)C(=O)N[C@H](CCC(N)=O)C(=O)N[C@@H](C(=O)N[C@H](C(=O)N[C@@H](CO)C(=O)N[C@H]1C(=O)N[C@@H](C)C(=O)N[C@@H](C[C@H]2CNC(=N)N2)C(=O)N[C@@H]([C@@H](C)CC)C(=O)O[C@H]1C)[C@@H](C)CC)[C@@H](C)CC]

(II)

or tautomer or pharmaceutically-acceptable salt thereof.

In one embodiment, the present invention relates to a method for producing a compound of Formula (III)

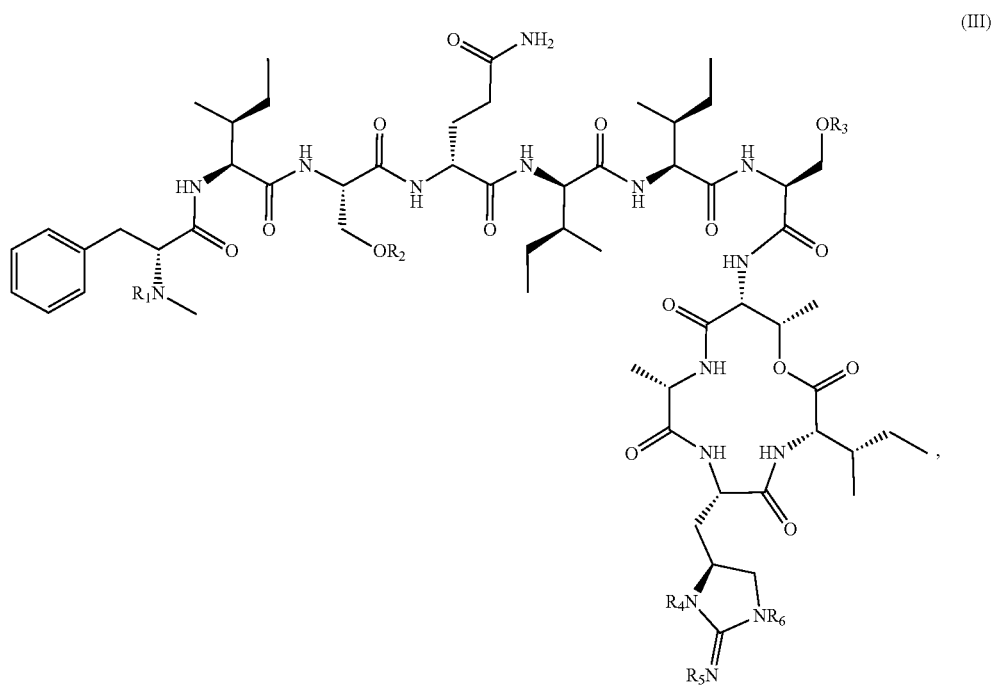

(III)

or a tautomer or pharmaceutically-acceptable salt thereof.

Each $R_1$-$R_6$ is independently selected from hydrogen, alkyl, alkenyl, alkynyl, cycloalkyl, cycloalkenyl, aryl, C(=O)$R_a$ and S(=O)$_2R_b$; each $R_a$ is independently hydrogen, alkyl, alkenyl, alkynyl, cycloalkyl, cycloalkenyl, or aryl; and each $R_b$ is independently alkyl, alkenyl, alkynyl, cycloalkyl, cycloalkenyl, or aryl. Any carbon or hydrogen may also be replaced with $^{13}$C or $^2$H, respectively.

In still another embodiment, the present invention relates to a method for producing a compound of Formula (IV):

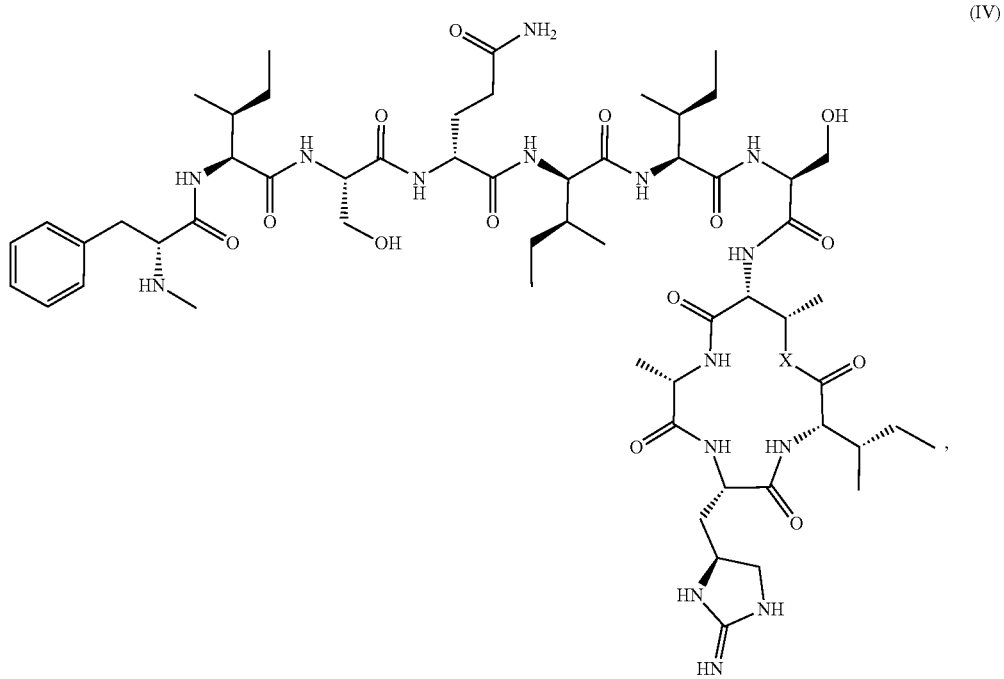

(IV)

wherein X is NH, O or S,
or a tautomer or pharmaceutically-acceptable salt thereof.

The method includes cultivating or culturing a bacterial isolate ISO18629 in a culture medium comprising assimilable sources of carbon, nitrogen, and inorganic salts under aerobic conditions, and enabling the production of an assayable amount of the compound of Formula (I), (II), (III) or (IV). Specific conditions for culturing the bacterial isolate ISO18629 are described in the examples section below.

In certain embodiments, the method further comprises isolating the compound of Formula (I), (II), (III) or (IV). The compound of Formula (I), (II), (III) or (IV) may be isolated by centrifuging the fermentation broth (e.g., centrifuging at 10,000 rpm for 20 minutes). The supernatant from the centrifugation is then adsorbed onto a reversed-phase polymeric resin (e.g., HP-20, Mitsubishi). After washing the column with water and 80% aqueous acetone, the compound is eluted with acetone. This acetone extract is then dried (e.g., under reduced pressure) leaving a thick, orange oil. Hexanes are then added to this oil and the mixture is then sonicated and centrifuged. The supernatant is then decanted and the remaining residue dried under reduced pressure. This reside is dissolved in DMSO and purified. The purification may be achieved by RP-HPLC on a preparatory C-18 column ($H_2O$/AcN with 0.1% TFA, 10-100% over 35 minutes). The fractions containing the compound may then be lyophilized. Specific conditions for isolating the compound of Formula (I), (II), (III) or (IV) are described in the examples section below.

In some embodiments, the method further comprises isolating the compound of Formula (I), (II), (III) or (IV) to at least about 75% purity (by dry weight). In other embodiments, the process further comprises isolating the compound of Formula (I), (II), (III) or (IV) to at least about 80% purity (by dry weight). In other embodiments, the process further comprises isolating the compound of Formula (I), (II), (III) or (IV) to at least about 85% purity (by dry weight). In other embodiments, the process further comprises isolating the compound of Formula (I), (II), (III) or (IV) to at least about 90% purity (by dry weight). In other embodiments, the process further comprises isolating the compound of Formula (I), (II), (III) or (IV) to at least about 95% purity (by dry weight). In other embodiments, the process further comprises isolating the compound of Formula (I), (II), (III) or (IV) to at least about 97% purity (by dry weight). In other embodiments, the process further comprises isolating the compound of Formula (I), (II), (III) or (IV) to at least about 99% purity (by dry weight).

In yet another embodiment, the present invention relates to a compound of Formula (I), (II), (III) or (IV) prepared according to the method described herein.

A compound of Formula (II), e.g., NOVO26 is produced by the ISO18629 isolate. The bacterial isolate ISO18629 was deposited with Agricultural Research Service Culture Collection (NRRL), National Center for Agricultural Utilization Research, Agricultural Research Service, U.S. Department of Agriculture, 1815 North University Street, Peoria, Illinois 61604, on Sep. 6, 2013, and assigned NRRL Accession Number B-50868. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. § 112.

ISO18629 was isolated from a terrestrial soil from Maine, using the technology for isolating "unculturable" microorganisms described in U.S. Pat. No. 7,011,957. This technology makes use of a growth chamber that is sealed with a semi-permeable membrane, and thus is permeable to diffusion of components from the environment but not to cells of microorganisms. The nucleotide sequence of the 16S rDNA gene of ISO18629 when compared by BLAST alignment to the GenBank nucleotide collection showed that it was most closely related (97.4% similarity) to a *Burkholderiales* bacterium YT0099 (Accession No. AB362826-1).

The growth chamber is designed to allow for the growth, isolation into pure culture, and characterization of microorganisms that are "uncultivable" at the present time. This desired result can be achieved because the conditions inside the chamber closely resemble, if they are not identical to, the natural environment of the microorganisms. One version of such a chamber is formed from a solid substrate, e.g., a glass or silicon slide or a nylon or a stainless steel washer, having an orifice which is sandwiched by two robust membranes, e.g., polycarbonate or other inert material, glued onto the substrate. The membranes have pore sizes, e.g., 0.025 µm-0.03 µm, that are sufficiently small to retain all microorganisms inside the chamber but which are sufficiently large to permit components from the environment to diffuse into the chamber and waste products to diffuse out of the chamber. After one membrane is sealed onto the bottom of the substrate, the chamber is partially filled with a suspension of cells in an appropriate growth medium.

Compounds of the present invention can be isolated from bacterial isolate ISO18629, for example, using the following method. The bacterial isolate can be grown on an appropriate support. A colony can then be homogenized and used to inoculate a seed broth. After fermentation, the seed culture can then be used to inoculate a production broth. After optional additional fermentation, the compound of Formula (I), (II), (III) or (IV) can be harvested from the broth, e.g., using centrifugation and preparatory HPLC. A specific exemplary method for producing the compound of Formula (II) is discussed in further detail below, in the Example section.

Alternatively, the compounds of the disclosure can be synthesized. For example, Scheme 1 represents one nonlimiting method of synthesizing guanidine substituted compounds of formula (III):

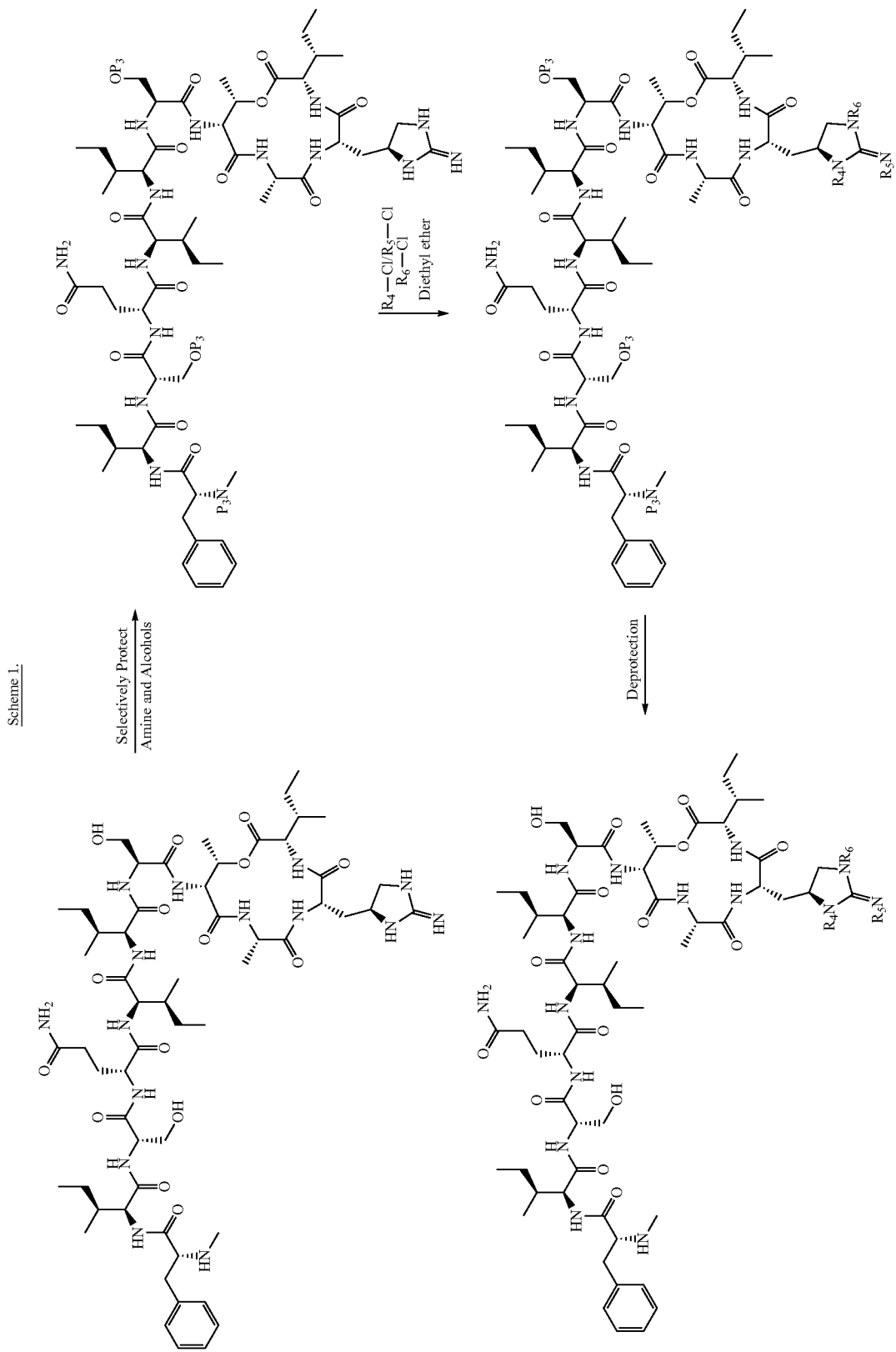
Scheme 1.

Scheme 2 is a nonlimiting representative example of a method of synthesizing amine substituted compounds of formula (III):

Scheme 2.
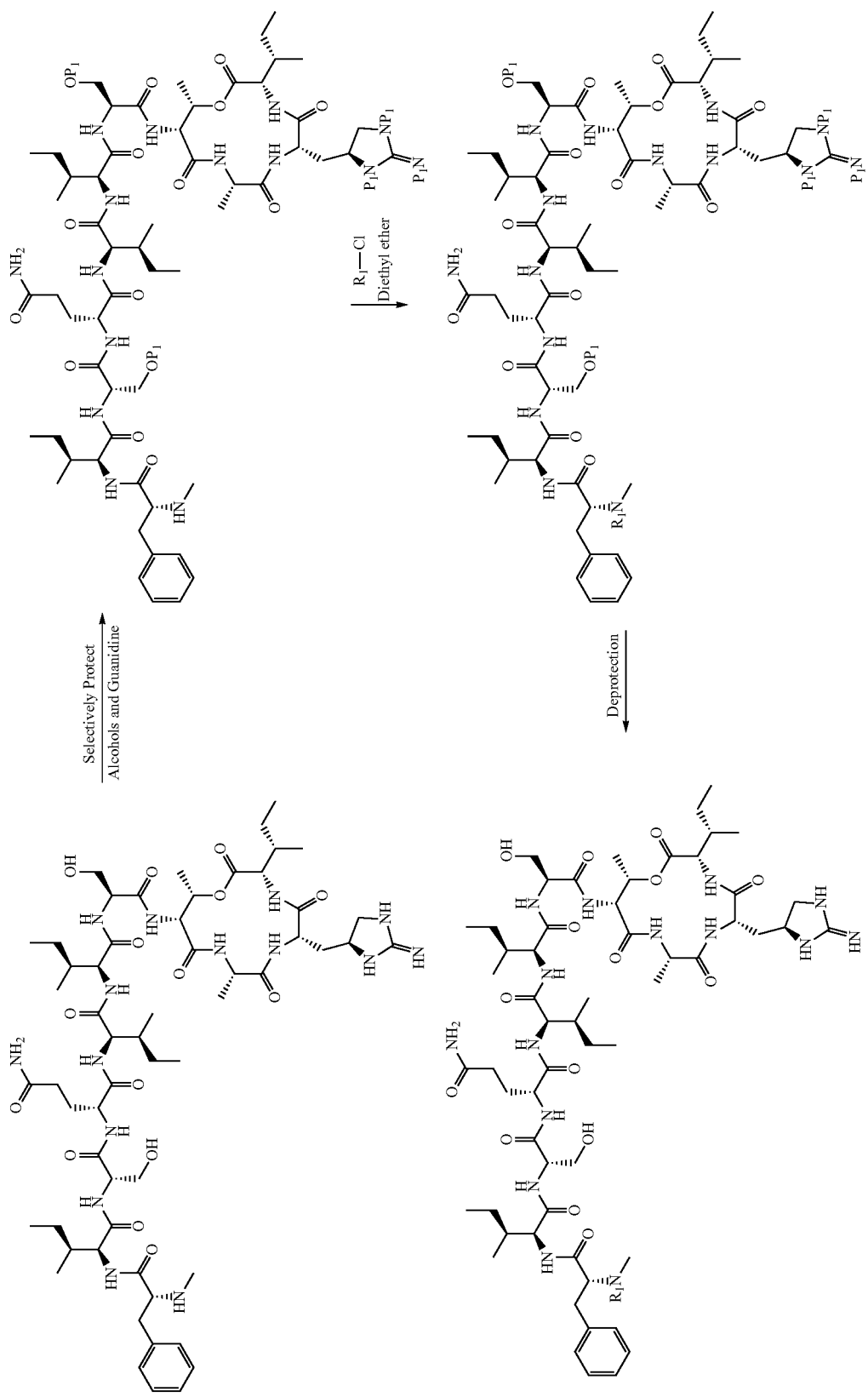

Scheme 3 provides a nonlimiting method of synthesizing alcohol substituted compounds of formula (III):

Scheme 3.
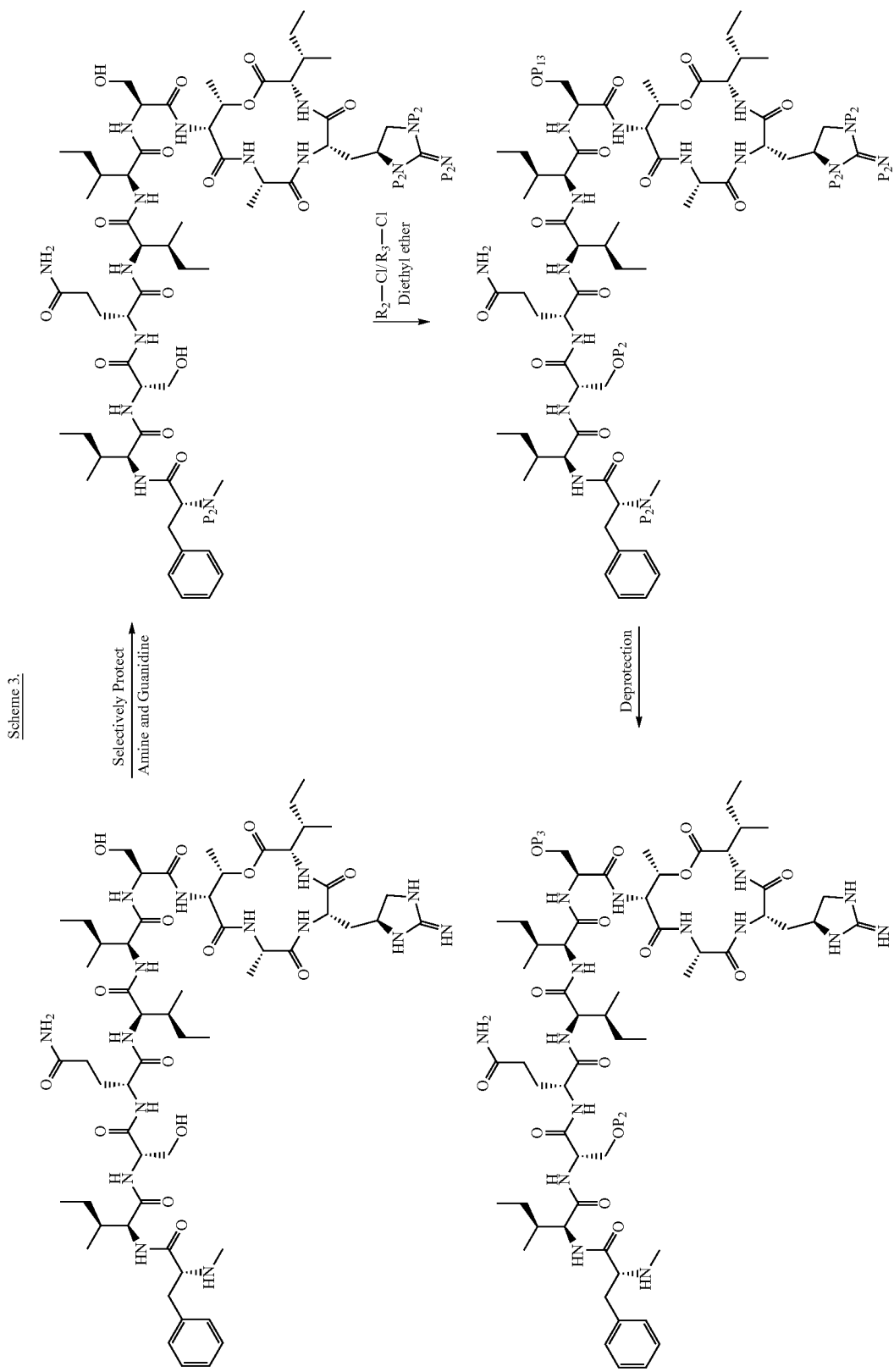

Scheme 4 is a representative method of synthesizing compounds of formula (IV):

Scheme 4.
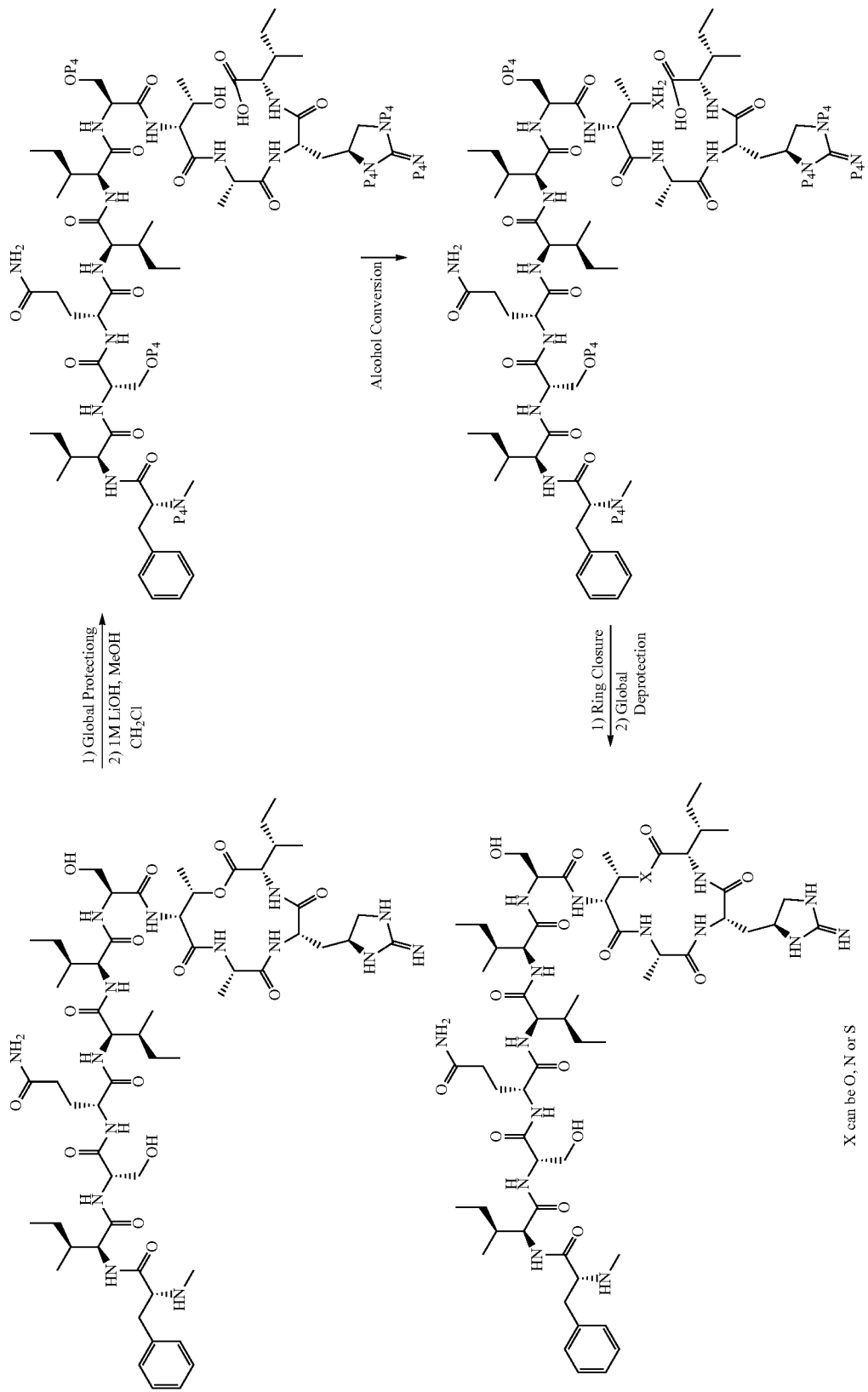
X can be O, N or S

Methods of Treatment Using the Compounds of the Invention

The present invention also provides methods of inhibiting the growth of a pathogen. The methods involve contacting the pathogen with an effective amount of one or more depsipeptide compounds of Formula (I), (II), (III) or (IV), thereby inhibiting the growth of the pathogen compared with the growth of the pathogen in the absence of treatment with the compound. In certain embodiments, the method reduces the growth of the pathogen compared with the growth of the pathogen in the absence of treatment with the compound. In other instances, the treatment results in the killing of the pathogen. Non-limiting examples of a pathogen include, but are not limited to, a bacterium, a fungus, a virus, a protozoan, a helminth, a parasite, and combinations thereof. These methods may be practiced in vivo or in vitro.

The anti-bacterial activity of the depsipeptide compounds of Formula (I), (II), (III) or (IV) with respect to a specific bacterium can be assessed by in vitro assays such as monitoring the zone of inhibition and the minimal inhibitory concentration (MIC) assays. The anti-fungal activity of the depsipeptide compounds of Formula (I), (II), (III) or (IV) can be determined, for example, by following the viability of the desired fungal pathogens (such as *Candida albicans*, and *Aspergillus* species) for example as described in Sanati et al., A new triazole, voriconazole (UK-109,496), blocks sterol biosynthesis in *Candida albicans* and *Candida krusei*, *Antimicrob. Agents Chemother.*, 1997 November; 41(11): 2492-2496. Anti-viral properties of the depsipeptide compounds of Formula (I), (II), (III) or (IV) can be determined, for example, by monitoring the inhibition of influenza neuraminidase or by assaying viral viability as described in Tisdale M., Monitoring of viral susceptibility: new challenges with the development of influenza NA inhibitors, *Rev. Med. Virol.*, 2000 January-February; 10(1):45-55. Anti-protozoan activity of the depsipeptide compounds of Formula (I), (II), (III) or (IV) can be determined by following the viability of protozoan parasites such as *Trichomonas vaginalis* and *Giardia lamblia* as described in Katiyar et al., Antiprotozoal activities of benzimidazoles and correlations with beta-tubulin sequence, *Antimicrob. Agents Chemother.*, 1994 September; 38(9): 2086-2090. Anthelminthic activity of the depsipeptide compounds of Formula (I), (II), (III) or (IV) can be determined, for example, by following the effect of the compounds on the viability of nematodes such as *Schistosoma mansoni*, *Schistosoma cercariae* and *Caenorhabditis elegans* as described in Mølgaard P. et al., Traditional herbal remedies used for the treatment of urinary schistosomiasis in Zimbabwe, *J. Ethnopharmacol.*, 1994 April; 42(2):125-32.

In other embodiments, the present invention is directed to methods of treating a disorder, e.g., a pathogen infection, in a subject in need thereof, by administering to the subject an effective amount of one or more depsipeptide compounds described herein. In certain embodiments, the disorder is caused by a pathogen such as, but not limited to, a bacterium, a fungus, a virus, a protozoan, a helminth, a parasite, or a combination thereof.

In some embodiments, the disorder is caused by a bacterium. The depsipeptide compounds described herein can be useful against both Gram-positive and Gram-negative bacteria. In particular, the disorder is caused by a Gram-positive bacterium. Alternatively, the disorder is caused by a Gram-negative bacterium. Non-limiting examples of Gram-positive bacteria include *Streptococcus*, *Staphylococcus*, *Enterococcus*, *Corynebacteria*, *Listeria*, *Bacillus*, *Erysipelothrix*, and *Actinomycetes*. In some embodiments, the compounds of Formula (I), (II), (III) or (IV) are used to treat an infection by one or more of: *Helicobacter pylori*, *Legionella pneumophilia*, *Mycobacterium tuberculosis*, *Mycobacterium avium*, *Mycobacterium intracellulare*, *Mycobacterium kansaii*, *Mycobacterium gordonae*, *Mycobacteria* sporozoites, *Staphylococcus aureus*, *Staphylococcus epidermidis*, *Neisseria gonorrhoeae*, *Neisseria meningitidis*, *Listeria monocytogenes*, *Streptococcus* pyogenes (Group A *Streptococcus*), *Streptococcus agalactiae* pyogenes (Group B *Streptococcus*), *Streptococcus dysgalactia*, *Streptococcus faecalis*, *Streptococcus bovis*, *Streptococcus pneumoniae*, pathogenic *Campylobacter* sporozoites, *Enterococcus* sporozoites, *Haemophilus influenzae*, *Pseudomonas aeruginosa*, *Bacillus anthracis*, *Bacillus subtilis*, *Escherichia coli*, *Corynebacterium diphtherias*, *Corynebacterium jeikeium*, *Corynebacterium* sporozoites, *Erysipelothrix rhusiopathiae*, *Clostridium perfringens*, *Clostridium tetani*, *Clostridium difficile*, *Enterobacter aerogenes*, *Klebsiella pneumoniae*, *Pasturella multocida*, *Bacteroides thetaiotamicron*, *Bacteroides uniformis*, *Bacteroides vulgatus*, *Fusobacterium nucleatum*, *Streptobacillus moniliformis*, *Leptospira*, and *Actinomyces israelii*. In specific embodiments, the compounds described herein are useful in treating an infection by Methicillin Resistant *Staphylococcus aureus* (MRSA) or by Vancomycin Resistant Entercocci (VRE). MRSA contributes to approximately 19,000 deaths annually in the United States. Although most of these deaths are due to hospital-acquired MRSA (HA-MRSA), community-acquired MRSA (CA-MRSA) is actually more virulent, and known to be potentially fatal to previously healthy individuals. The virulence of CA-MRSA is in part due to the expression of phenol soluble modulins or PSM peptides. Accordingly, in treating CA-MRSA, one can use a compound of Formula (I), (II), (III) or (IV) in combination with an agent that modulates the expression and/or activity of virulence factors, such as, but not limited to, PSM peptides. In certain embodiments, the depsipeptide compounds of Formula (I), (II), (III) or (IV) may be used to treat spirochetes such as *Borelia burgdorferi*, *Treponema pallidium*, and *Treponema pertenue*.

In a particular embodiment, the Gram-positive bacteria are selected from *Staphylococcus* (including for example, *S. aureus* spp., *S. epidermidis* spp., *S. warneri* spp. and *S. haemolyticus* spp.); *Streptococcus* (including, for example, *S. viridans* spp., *S. pneumoniae* spp., *S. agalactiae* spp., and *S. pyogenes* spp.); *Bacillus* (including, for example, *B. anthracis* spp. and *B. subtilis*, spp.); *Clostridium* (including, for example, *C. difficile* spp.); *Propionibacterium* (including, for example, *P. acnes* spp.); *Enterococcus* (including, for example, *E. faecium* spp., *E. faecalis* spp., Vancomycin-resistant *E. faecium* spp., and Vancomycin-resistant *E. faecalis* spp.); and *Mycobacterium* (including, for example, *M. smegmatis* spp. and *M. tuberculosis* spp.). The compounds described herein are useful for treating disorders caused by these bacteria. Examples of such disorders include acute bacterial skin and skin structure infections, *C. difficile* associated diarrhea, anthrax, sepsis, botulism, urinary tract infections, bacteremia, bacterial endocarditis, diverticulitis, meningitis, pneumonia, and tuberculosis.

In a particular embodiment, the Gram-negative bacteria are selected from *Haemophilus* (including for example, *H. influenzae* spp.); *Klebsiella* (including, for example, *K. pneumoniae* spp.); *Pseudomonas* (including, for example, *P. aeruginosa* spp.); *Escherichia* (including, for example, *E. coli* spp.); *Yersinia* (including, for example, *Y. pestis* spp.); *Neisseria* (including, for example, *N. gonorrhoeae* spp.); *Bacteriodes* (including, for example, *B. fragilis* spp.); *Pro-* teus (including, for example, *P. mirabilis* spp. and *P. vulgaris* spp.); *Enterobacter* (including, for example, *E. cloacae* spp. and *E. aerogenes* spp.; *Serratia* (including, for example, *S. marcescens* spp.); *Acinetobacter* (including, for example, *A. baumannii* spp.); and *Moraxella* (including, for example, *M. catarrhalis* spp.). In a specific embodiment, the Gram-negative bacteria is *Haemophilus*, and in particular, *H. influenzae*; or *Moraxella*, and in particular, *M. catarrhalis* spp. The compounds described herein are useful for treating disorders caused by these bacteria. Examples of such disorders include influenza, bacteremia, pneumonia, acute bacterial meningitis, gonorrhea, urinary tract infections, respiratory tract infections, catheter-associated bacteremia, wound infections, otitis media, bronchitis, sinusitis, and laryngitis. In other embodiments, the depsipeptide compounds described herein may be useful in treating viral disorders. Non-limiting examples of infectious viruses that may be treated by the compounds of Formula (I), (II), (III) or (IV) include: Retroviridae (e.g., human immunodeficiency viruses, such as HIV-1 (also referred to as HTLV-III, LAV or HTLV-III/LAV), or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses, severe acute respiratory syndrome (SARS) virus); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arenaviridae (hemorrhagic fever viruses); Reoviridae (e.g., reoviruses, orbiviurses and rotaviruses); Birnaviridae; Hepadnaviridae (e.g, Hepatitis B virus); Parvoviridae (parvoviruses); Papovaviridae (papilloma viruses, polyoma viruses); Adenoviridae (most adenoviruses); Herpesviridae (e.g., herpes simplex virus (HSV) 1 and 2, varicella zoster virus, cytomegalovirus (CMV), herpes viruses); Poxviridae (e.g., variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parentally transmitted, i.e., Hepatitis C); Norwalk and related viruses, and astroviruses). In specific embodiments, the compounds of Formula (I), (II), (III) or (IV) are used to treat an influenza virus, human immunodeficiency virus, and herpes simplex virus.

In some embodiments, the depsipeptide compounds of Formula (I), (II), (III) or (IV) may be useful to treat disorders caused by fungi. Non-limiting examples of fungi that may be inhibited by the compounds of Formula (I), (II), (III) or (IV) include, but are not limited to, *Cryptococcus neoformans, Histoplasma capsulatum, Coccidioides immitis, Blastomyces dermatitidis, Chlamydia trachomatis, Candida albicans, Candida tropicalis, Candida glabrata, Candida krusei, Candida parapsilosis, Candida dubliniensis, Candida lusitaniae, Epidermophyton floccosum, Microsporum audouinii, Microsporum canis, Microsporum canis* var. *distortum Microsporum cookei, Microsporum equinum, Microsporum ferrugineum, Microsporum fulvum, Microsporum gallinae, Microsporum gypseum, Microsporum nanum, Microsporum persicolor, Trichophyton ajelloi, Trichophyton concentricum, Trichophyton equinum, Trichophyton flavescens, Trichophyton gloriae, Trichophyton megnini, Trichophyton mentagrophytes* var. *erinacei, Trichophyton mentagrophytes* var. *interdigitale, Trichophyton phaseoliforme, Trichophyton rubrum, Trichophyton rubrum* downy strain, *Trichophyton rubrum* granular strain, *Trichophyton schoenleinii, Trichophyton simii, Trichophyton soudanense, Trichophyton terrestre, Trichophyton tonsurans, Trichophyton vanbreuseghemii, Trichophyton verrucosum, Trichophyton violaceum, Trichophyton yaoundei, Aspergillus fumigatus, Aspergillus flavus*, and *Aspergillus clavatus*.

In yet other embodiments, the depsipeptide compounds described herein are useful in treating disorders caused by protozoans. Non-limiting examples of protozoa that can be inhibited by the compounds of Formula (I), (II), (III) or (IV) include, but are not limited to, *Trichomonas vaginalis, Giardia lamblia, Entamoeba histolytica, Balantidium coli, Cryptosporidium parvum* and *Isospora belli, Trypansoma cruzi, Trypanosoma gambiense, Leishmania donovani*, and *Naegleria fowleri*.

In certain embodiments, the depsipeptide compounds described herein are useful in treating disorders caused by helminths. Non-limiting examples of helminths that can be inhibited by the compounds of Formula (I), (II), (III) or (IV) include, but are not limited to: *Schistosoma mansoni, Schistosoma cercariae, Schistosoma japonicum, Schistosoma mekongi, Schistosoma hematobium, Ascaris lumbricoides, Strongyloides stercoralis, Echinococcus granulosus, Echinococcus multilocularis, Angiostrongylus cantonensis, Angiostrongylus constaricensis, Fasciolopis buski, Capillaria philippinensis, Paragonimus westermani, Ancylostoma dudodenale, Necator americanus, Trichinella spiralis, Wuchereria bancrofti, Brugia malayi*, and *Brugia timori, Toxocara canis, Toxocara cati, Toxocara vitulorum, Caenorhabiditis elegans*, and *Anisakis* species.

In some embodiments, the depsipeptide compounds described herein are useful in treating disorders caused by parasites. Non-limiting examples of parasites that can be inhibited by the compounds of Formula (I), (II), (III) or (IV) include, but are not limited to, *Plasmodium falciparum, Plasmodium yoelli, Hymenolepis nana, Clonorchis sinensis, Loa boa, Paragonimus westermani, Fasciola hepatica*, and *Toxoplasma gondii*. In specific embodiments, the parasite is a malarial parasite.

In other embodiments, the depsipeptide compounds are used to inhibit the growth of an infective agent compared with the growth of the infective agent in the absence of being treated by the compound. Non-limiting examples of infective agents include, but are not limited to, bacteria, fungi, viruses, protozoa, helminthes, parasites, and combinations thereof. The depsipeptide compounds may be used to inhibit the agent in vivo or in vitro.

Pharmaceutical Compositions Containing the Compounds of the Invention

The present invention also provides pharmaceutical compositions comprising at least one of the depsipeptide compounds of Formula (I), (II), (III) or (IV), and a pharmaceutically-acceptable carrier. These depsipeptide compositions are suitable for administration to a subject (e.g., a mammal such as a human). The pharmaceutical composition can be used for treating a disorder. Non-limiting examples of such disorders are provided above and include an infection by a pathogen, e.g., a bacterium.

In one embodiment, the depsipeptide compounds are administered in a pharmaceutically-acceptable carrier. Any suitable carrier known in the art may be used. Carriers that efficiently solubilize the compounds of the invention are preferred. Carriers include, but are not limited to, a solid, liquid, or a mixture of a solid and a liquid. The carriers may take the form of capsules, tablets, pills, powders, lozenges, suspensions, emulsions, or syrups. The carriers may include substances that act as flavoring agents, lubricants, solubilizers, suspending agents, binders, stabilizers, tablet disintegrating agents, and encapsulating materials. The phrase "pharmaceutically-acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Non-limiting examples of materials which can serve as pharmaceutically-acceptable carriers include: (1) sugars, such as lactose, glucose, and sucrose; (2) starches, such as corn starch and potato starch; (3) cellulose and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline, (18) Ringer's solution, (19) ethyl alcohol; (20) phosphate buffer solutions; and (21) other non-toxic compatible substances employed in pharmaceutical formulations.

The formulations may conveniently be presented in unit dosage form and may be prepared by any methods well known in the art of pharmacy. The amount of active ingredient which can be combined with a carrier material to produce a single-dosage form will vary depending upon the subject being treated, the particular mode of administration, and the particular condition being treated, among others. The amount of active ingredient that can be combined with a carrier material to produce a single-dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of Formula (I), (II), (III) or (IV) with the carrier and, optionally, one or more accessory ingredients. In general, the formulations are prepared by uniformly and intimately bringing into association a depsipeptide compound of Formula (I), (II), (III) or (IV) with liquid carriers, or timely divided solid carriers, or both, and then, if necessary, shaping the product.

In solid dosage forms for oral administration (e.g., capsules, tablets, pills, dragees, powders, granules, and the like), the active ingredient is mixed with one or more additional ingredients, such as sodium citrate or dicalcium phosphate, and/or any of the following: fillers or extenders, such as, but not limited to, starches, lactose, sucrose, glucose, mannitol, and/or silicic acid; binders, such as, but not limited to, carboxymethylcellulose, alginates, gelatin, polyvinyl pyrrolidone, sucrose, and/or acacia; humectants, such as, but not limited to, glycerol; disintegrating agents, such as, but not limited to, agar, calcium carbonate, potato or tapioca starch, alginic acid, certain silicates, and sodium carbonate; solution retarding agents, such as, but not limited to, paraffin; absorption accelerators, such as, but not limited to, quaternary ammonium compounds; wetting agents, such as, but not limited to, cetyl alcohol and glycerol monostearate; absorbents, such as, but not limited to, kaolin and bentonite clay; lubricants, such as, but not limited to, talc, calcium stearate, magnesium stearate, solid polyethylene glycols, sodium lauryl sulfate, and mixtures thereof; and coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

In powders, the carrier is a finely-divided solid, which is mixed with an effective amount of a finely-divided agent. Powders and sprays can contain, in addition to a compound of Formula (I), (II), (III) or (IV), excipients, such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Tablets for systemic oral administration may include one or more excipients as known in the art, such as, for example, calcium carbonate, sodium carbonate, sugars (e.g., lactose, sucrose, mannitol, sorbitol), celluloses (e.g., methyl cellulose, sodium carboxymethyl cellulose), gums (e.g., arabic, tragacanth), together with one or more disintegrating agents (e.g., maize, starch, or alginic acid, binding agents, such as, for example, gelatin, collagen, or acacia), lubricating agents (e.g., magnesium stearate, stearic acid, or talc), inert diluents, preservatives, disintegrants (e.g., sodium starch glycolate), surface-active and/or dispersing agent. A tablet may be made by compression or molding, optionally with one or more accessory ingredients.

In solutions, suspensions, emulsions or syrups, an effective amount of the depsipeptide compound is dissolved or suspended in a carrier, such as sterile water or an organic solvent, such as aqueous propylene glycol. Other compositions can be made by dispersing the compound in an aqueous starch or sodium carboxymethyl cellulose solution or a suitable oil known to the art. The liquid dosage forms may contain inert diluents commonly used in the art, such as, for example, water or other solvents, solubilizing agents and emulsifiers, such as, but not limited to, ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols, and fatty acid esters of sorbitan, and mixtures thereof.

Besides inert diluents, the oral compositions can also include adjuvants, such as wetting agents, emulsifying and suspending agents, sweetening, flavoring, coloring, perfuming, and preservative agents.

Suspensions, in addition to the active compound, may contain suspending agents as, for example, ethoxylated isostearyl alcohols, polyoxyethylene sorbitol and sorbitan esters, microcrystalline cellulose, aluminum metahydroxide, bentonite, agar and tragacanth, and mixtures thereof.

Formulations of the pharmaceutical compositions for rectal or vaginal administration may be presented as a suppository, which may be prepared by mixing one or more compounds of Formula (I), (II), (III) or (IV) with one or more suitable non-irritating excipients or carriers comprising, for example, cocoa butter, polyethylene glycol, a suppository wax or a salicylate, and which is solid at room temperature but liquid at body temperature and, thus, will melt in the rectum or vaginal cavity and release the agents. Formulations suitable for vaginal administration also include pessaries, tampons, creams, gels, pastes, foams, or spray formulations containing such carriers as are known in the art to be appropriate.

Dosage forms for the topical or transdermal administration of a compound of Formula (I), (II), (III) or (IV) include powders, sprays, ointments, pastes, creams, lotions, gels, solutions, drops, patches, and inhalants. The active depsipeptide compound may be mixed under sterile conditions with a pharmaceutically-acceptable carrier, and with any preservatives, buffers, or propellants that may be required.

Ointments, pastes, creams, and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Transdermal patches have the added advantage of providing controlled delivery of a compound of Formula (I), (II), (III) or (IV) to the body. Such dosage forms can be made by dissolving or dispersing the agents in the proper medium. Absorption enhancers can also be used to increase the flux of the agents across the skin. The rate of such flux can be controlled by either providing a rate controlling membrane or dispersing the depsipeptide compound in a polymer matrix or gel.

The depsipeptide compounds are administered in an effective amount to a subject in need of such treatment. The phrase "effective amount" as used herein means the amount of a compound of Formula (I), (II), (III) or (IV), or composition comprising the compound of Formula (I), (II), (III) or (IV), that is effective for producing some desired effect in an animal. It is recognized that when an agent is being used to achieve a therapeutic effect, the actual dose which comprises the "effective amount" will vary depending on a number of conditions including, but not limited to, the particular condition being treated, the severity of the disease, the size and health of the patient, the route of administration. A skilled medical practitioner can readily determine the appropriate dose using methods well known in the medical arts. In some embodiments, an effective amount is an amount effective in treating a disorder in a subject in need thereof. Furthermore, a skilled practitioner will appreciate that the effective amount of the depsipeptide compound may be lowered or increased by fine-tuning and/or by administering more than one depsipeptide compound, or by administering a depsipeptide compound together with a second agent (e.g., antibiotics, antifungals, antivirals, NSAIDS, DMARDS, steroids, etc.). An effective amount may be determined, for example, empirically by starting at relatively low amounts and by step-wise increments with concurrent evaluation of beneficial effect (e.g., reduction in symptoms). The actual effective amount will be established by dose/response assays using methods standard in the art (Johnson et al., *Diabetes.* 42:1179, (1993)). As is known to those in the art, the effective amount will depend on bioavailability, bioactivity, and biodegradability of the depsipeptide compound.

In some embodiments, an effective amount is an amount that is capable of reducing the symptoms of the disorder in a subject. Accordingly, the amount can vary with the subject being treated. For example, the effective amount of the depsipeptide compound may comprise from about 1 µg/kg body weight to about 100 mg/kg body weight. In one embodiment, the effective amount of the compound comprises from about 1 µg/kg body weight to about 50 mg/kg body weight. In a further embodiment, the effective amount of the compound comprises from about 10 µg/kg body weight to about 10 mg/kg body weight. When one or more depsipeptide compounds or agents are combined with a carrier, they may be present in an amount of about 1 weight percent to about 99 weight percent, the remainder being composed of the pharmaceutically-acceptable carrier. In some embodiments, an effective amount is between about 1 mg and about 10 g per dose, e.g., between about 10 mg and about 1 g per dose. Values and ranges intermediate to the above-recited ranges are intended to be encompassed by the present teachings.

Administration of the depsipeptide compound may be hourly, daily, weekly, monthly, yearly, or a single event. In addition, administration can have a duration of from one day to one year or more. In some embodiments, administration refers to daily administration for a period of time, e.g., for about a week, two weeks, three weeks, one month, three months, six months or a year. In some embodiments, administration refers to weekly administration for a period of time, e.g., for about a month, three months, six months, one year or more.

The present invention also provides for kits that comprise at least one depsipeptide compound of Formula (I), (II), (III) or (IV). The kits may contain at least one container and may also include instructions directing the use of these materials. In another embodiment, a kit may include an agent used to treat the disorder in question with or without such above-mentioned materials that may be present to determine if a subject has an inflammatory disease.

Administration of the Pharmaceutical Compositions of the Invention

Methods of administration of the formulations of the present invention comprising the depsipeptide compounds of Formula (I), (II), (III) or (IV) described herein can be by any of a number of methods well known in the art. These methods include local or systemic administration. Exemplary routes of administration include oral, parenteral, transdermal, intradermal, intramuscular, intraperitoneal, intravenous, subcutaneous, intranasal (e.g., nebulizer, inhaler, aerosol dispenser), intraocular (e.g., for the treatment of conjunctivitis), intraaural (e.g., for the treatment of ear infections), colorectal, rectal, intravaginal, and any combinations thereof. In addition, it may be desirable to introduce the pharmaceutical compositions of the present invention into the central nervous system by any suitable route, including intraventricular and intrathecal injection. Intraventricular injection may be facilitated by an intraventricular catheter, for example, attached to a reservoir, such as an Ommaya reservoir. Methods of introduction may also be provided by rechargeable or biodegradable devices, e.g., depots. Furthermore, it is contemplated that administration may occur by coating a device, implant, stent, or prosthetic. The compounds of Formula (I), (II), (III) or (IV) can also be used to coat catheters in any situation where catheters are inserted in the body.

In another embodiment, the subject depsipeptide compounds can be administered as part of a combination therapy with other agents. Combination therapy refers to any form of administration combining two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either simultaneously or sequentially. Thus, an individual who receives such treatment can have a combined effect of different therapeutic compounds.

For example, depsipeptide compounds may be used in combination with other known antibiotics. The depsipeptide compounds of Formula (I), (II), (III) or (IV) may either be administered sequentially or substantially at the same time. Varying the antibiotic can be helpful in reducing the ability of the pathogen to develop resistance to the drug. Non-limiting examples of antibiotics include penicillins (e.g., natural penicillins, penicillinase-resistant penicillins, antipseudomonal penicillins, aminopenicillins), tetracyclines, macrolides (e.g., erythromycin), lincosamides (e.g., clindamycin), streptogramins (e.g., Synercid), aminoglycosides, and sulfonamides. In some embodiments, the depsipeptide compounds of Formula (I), (II), (III) or (IV) are used in combination with compounds that target virulence factors such as, but not limited to, phenol-soluble modulins. In some embodiments, the depsipeptide compounds of Formula (I), (II), (III) or (IV) are used in combination with compounds that target the efflux pumps of the pathogens.

Kits and Articles of Manufacture Comprising Pharmaceutical Compositions of Compounds of the Invention Also within the scope of the present invention are kits comprising the compounds of Formula (I), (II), (III) or (IV), or a pharmaceutically acceptable salt thereof, and instructions for use. The term "kit" as used herein refers to a packaged product comprising components with which to administer a pharmaceutical composition comprising the compounds of Formula (I), (II), (III) or (IV), or a pharmaceutically acceptable salt thereof, of the invention for treatment of a disorder caused by a pathogen. The kit preferably comprises a box or container that holds the components of the kit. The box or container is affixed with a label or a Food and Drug Administration approved protocol. The box or container holds components of the invention which are preferably contained within plastic, polyethylene, polypropylene, ethylene, or propylene vessels. The vessels can be capped-tubes or bottles or bottles containing a dropper suitable for the dropwise administration of a solution containing the compounds of the invention, e.g., into the ear or eye of a subject. The kit can also include instructions for administering a pharmaceutical composition comprising compounds of Formula (I), (II), (III) or (IV), or a pharmaceutically acceptable salt thereof. In a particular embodiment, the kit may comprise (a) a pharmaceutical composition comprising a compound of Formula (I), (II) or (III) or a pharmaceutically acceptable salt thereof, wherein the pharmaceutical composition is in a container; and (b) instructions describing a method of using the pharmaceutical composition.

The kit can further contain one more additional reagent, such as an antibiotic, an antifungal agent, an antiviral agent, an anti-protozoan agent, an anthelminthic agent, an anti-neoplastic agent, an immunoregulating agent, an anti-hypercholesterolemia agent and combinations thereof. Kits typically include a label indicating the intended use of the contents of the kit. The term label includes any writing, or recorded material supplied on or with the kit, or which otherwise accompanies the kit.

The invention also provides a pharmaceutical pack or kit comprising one or more containers filled with a liquid formulation of a pharmaceutical composition comprising a compound of Formula (I), (II), (III) or (IV), or a pharmaceutically acceptable salt thereof. In one embodiment, a container filled with a liquid formulation of the invention is a pre-filled syringe. In a specific embodiment, the formulations of the invention are formulated in single dose vials as a sterile liquid. For example, the formulations may be supplied in 3 cc USP Type I borosilicate amber vials (West Pharmaceutical Services—Part No. 6800-0675) with a target volume of 1.2 mL. Optionally associated with such container(s) can be a notice in the form prescribed by a governmental agency regulating the manufacture, use or sale of pharmaceuticals or biological products, which notice reflects approval by the agency of manufacture, use or sale for human administration.

Any pre-filled syringe known to one of skill in the art may be used in combination with a liquid formulation of the invention. Pre-filled syringes that may be used are described in, for example, but not limited to, PCT Publications WO05032627, WO08094984, WO9945985, WO03077976, U.S. Pat. Nos. 6,792,743, 5,607,400, 5,893,842, 7,081,107, 7,041,087, 5,989,227, 6,807,797, 6,142,976, 5,899,889, US Patent Publications US20070161961A1, US20050075611A1, US20070092487A1, US20040267194A1, US20060129108A1. Pre-filled syringes may be made of various materials. In one embodiment a pre-filled syringe is a glass syringe. In another embodiment a pre-filled syringe is a plastic syringe. One of skill in the art understands that the nature and/or quality of the materials used for manufacturing the syringe may influence the stability of a compound formulation stored in the syringe. For example, it is understood that silicon based lubricants deposited on the inside surface of the syringe chamber may affect particle formation in the compound formulation. In one embodiment, a pre-filled syringe comprises a silicone based lubricant. In one embodiment, a pre-filled syringe comprises baked on silicone. In another embodiment, a pre-filled syringe is free from silicone based lubricants. One of skill in the art also understands that small amounts of contaminating elements leaching into the formulation from the syringe barrel, syringe tip cap, plunger or stopper may also influence stability of the formulation. For example, it is understood that tungsten introduced during the manufacturing process may adversely affect formulation stability. In one embodiment, a pre-filled syringe may comprise tungsten at a level above 500 ppb. In another embodiment, a pre-filled syringe is a low tungsten syringe. In another embodiment, a pre-filled syringe may comprise tungsten at a level between about 500 ppb and about 10 ppb, between about 400 ppb and about 10 ppb, between about 300 ppb and about 10 ppb, between about 200 ppb and about 10 ppb, between about 100 ppb and about 10 ppb, between about 50 ppb and about 10 ppb, between about 25 ppb and about 10 ppb.

The present invention also encompasses a finished packaged and labeled pharmaceutical product. This article of manufacture includes the appropriate unit dosage form in an appropriate vessel or container such as a glass vial, pre-filled syringe or other container that is hermetically sealed. In one embodiment, the unit dosage form is provided as a sterile particulate free solution comprising pharmaceutical composition comprising a compound of Formula (I), (II), (III) or (IV), or a pharmaceutically acceptable salt thereof, that is suitable for parenteral administration. In another embodiment, the unit dosage form is provided as a sterile lyophilized powder comprising a pharmaceutical composition comprising a compound of Formula (I), (II), (III) or (IV), or a pharmaceutically acceptable salt thereof, that is suitable for reconstitution.

In one embodiment, the unit dosage form is suitable for intravenous, intramuscular, intranasal, oral, topical or subcutaneous delivery. Thus, the invention encompasses sterile solutions suitable for each delivery route. The invention further encompasses sterile lyophilized powders that are suitable for reconstitution.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question, as well as how and how frequently to administer the pharmaceutical. In other words, the article of manufacture includes instruction means indicating or suggesting a dosing regimen including, but not limited to, actual doses, monitoring procedures, and other monitoring information.

Specifically, the invention provides an article of manufacture comprising packaging material, such as a box, bottle, tube, vial, container, pre-filled syringe, sprayer, insufflator, intravenous (i.v.) bag, envelope and the like; and at least one unit dosage form of a compound of the invention contained within the packaging material, wherein the compound comprises a liquid formulation containing an antibiotic. The packaging material includes instruction means which indicate how that the compound can be used to prevent, treat and/or manage one or more symptoms associated with a disease or disorder.

The present invention is further illustrated by the following examples which should not be construed as limiting in any way. Throughout this application, various patents, patent applications, and publications are referenced. The disclosures of these patents, patent applications, and publications in their entireties are hereby incorporated by reference into this application. The instant disclosure will govern in the instance that there is any inconsistency between the patents, patent applications, and publications and this disclosure.

EXEMPLIFICATION

Example 1: Preparation of a Compound of Formula (II)

Bacterial isolate (ISO18629) was grown on 2% bacto agar with 0.125 g/L casein digest, 0.1 g/L potato starch, 1 g/L Casamino acids, and supplemented with 10% R4 (100% R4 being 10 g/liter glucose, 1 g/liter yeast extract, 0.1 g/liter casamino acids, 3 g/liter L-proline, 10 g/liter $MgCl_2·6H_2$, 4 g/liter $CaCl_2$ $2H_2O$, 0.2 g/liter $K_2SO_4$, 5.6 g/liter TES 0.56%, 1 mL Trace Elements all brought to a total of 1 liter of tap water and adjusted to pH 7.0 with 1.0 M NaOH) and one colony was homogenized and used to inoculate 40 ml of BP seed broth (15 g/liter glucose, 10 g/liter malt extract, 10 g/liter soluble starch, 5 g/liter yeast extract, 10 g/liter casamino acid, 0.05 g/liter calcium carbonate brought to a total of 1 liter with tap water) in a 250 mL flask. After 4 days of fermentation at 28° C. (250 rpm) 12.5 mL of seed culture was used to inoculate 0.5 L of R4 production broth at 2.5% inoculum (v/v). The fermentation was conducted for 7 days at 28° C. (180 rpm) prior to harvest.

The fermentation broth was centrifuged at 10,000 rpm for 20 minutes. The supernatant was adsorbed onto a reversed-phase polymeric resin (HP-20, Mitsubishi). After washing the column with water and 80% aqueous acetone, the compound was eluted with acetone. This acetone extract was then dried under reduced pressure, leaving a thick, orange oil. Hexanes were then added to this oil and the mixture was then sonicated and centrifuged. The supernatant was then decanted and the remaining residue dried under reduced pressure. This reside was dissolved in DMSO and purified by RP-HPLC on a preparatory C-18 column ($H_2O$/AcN with 0.1% TFA, 10-100% can over 35 minutes). The fractions containing the compound of Formula (I) or (II) were lyophilized to leave a white powder.

The 2D structure of the compound of Formula (II) was determined by $^1H$, $^{13}C$, COSY, DEPT-135, HSQC and HMBC NMR experimentation, which can be seen in in FIGS. 1-6, respectively. The $^{13}C$ assignment for the structure is as follows:

TABLE 1

$^{13}C$ NMR data of the compound of Formula (II) in DMSO-$d_6$ (125 MHz, δ in ppm)

| Position | δ ($^{13}C$) |
|---|---|
| 1 | 31.9 |
| 2 | 61.9 |
| 3 | 36.4 |
| 4 | 135.0 |
| 5, 5' | 129.7 |
| 6, 6' | 128.9 |
| 7 | 127.5 |
| 8 | 167.1 |
| 9 | 57.9 |
| 10 | 36.5 |
| 11 | 15.5 |
| 12 | 24.4 |
| 13 | 11.3 |
| 14 | 170.6 |
| 15 | 55.6 |
| 16 | 62.4 |
| 17 | 170.2 |
| 18 | 52.7 |
| 19 | 31.9 |
| 20 | 28.4 |
| 21 | 174.4 |
| 22 | 170.9 or 171.4 or 171.6 or 171.7 or 171.8 |
| 23 | 56.8 |
| 24 | 37.4 |
| 25 | 14.7 or 15.4 or 16.0 |
| 26 | 26.2 |
| 27 | 10.6 or 11.2 or 11.8 |
| 28 | 170.9 or 171.4 or 171.6 or 171.7 or 171.8 |
| 29 | 57.3 |
| 30 | 36.9 |
| 31 | 14.7 or 15.4 or 16.0 |
| 32 | 25.3 |
| 33 | 10.6 or 11.2 or 11.8 |
| 34 | 170.9 or 171.4 or 171.6 or 171.7 or 171.8 |
| 35 | 56.5 |
| 36 | 62.7 |
| 37 | 170.9 or 171.4 or 171.6 or 171.7 or 171.8 |
| 38 | 56.2 |
| 39 | 71.2 |
| 40 | 15.9 |
| 41 | 168.9 |
| 42 | 52.2 |
| 43 | 17.1 |
| 44 | 173.1 |
| 45 | 52.2 |
| 46 | 37.2 |
| 47 | 53.5 |
| 48 | 48.3 |
| 49 | 160.0 |
| 50 | 170.9 or 171.4 or 171.6 or 171.7 or 171.8 |
| 51 | 57.8 |
| 52 | 36.3 |
| 53 | 14.7 or 15.4 or 16.0 |

TABLE 1-continued $^{13}$C NMR data of the compound of Formula (II) in DMSO-$d_6$ (125 MHz, δ in ppm)

| Position | δ ($^{13}$C) |
|---|---|
| 54 | 24.5 |
| 55 | 10.6 or 11.2 or 11.8 |
| 56 | 169.3 |

Additionally, this structure was confirmed by MS/MS:

TABLE 2

MS/MS Fragments and corresponding formulas

| Fragment Formula | Fragment Mass |
|---|---|
| $C_6H_{11}N_4O^+$ | 155.1 |
| $C_{16}H_{23}N_2O_2^+$ | 275.1 |
| $C_{12}H_{24}N_5O_3^+$ | 286.2 |
| $C_{15}H_{29}N_6O_4^+$ | 357.2 |
| $C_{19}H_{28}N_3O_4^+$ | 362.2 |
| $C_{19}H_{34}N_7O_5^+$ | 440.2 |
| $C_{24}H_{36}N_5O_6^+$ | 490.2 |
| $C_{22}H_{39}N_8O_7^+$ | 527.3 |
| $C_{30}H_{47}N_6O_7^+$ | 603.3 |
| $C_{28}H_{50}N_9O_8^+$ | 640.3 |
| $C_{36}H_{58}N_7O_8^+$ | 716.4 |
| $C_{34}H_{61}N_{10}O_9^+$ | 753.4 |
| $C_{39}H_{69}N_{12}O_{11}^+$ | 881.5 |
| $C_{42}H_{74}N_{13}O_{13}^+$ | 968.5 |
| $C_{48}H_{85}N_{14}O_{14}^+$ | 1081.5 |
| $C_{52}H_{85}N_{14}O_{14}^+$ | 1129.5 |

All fragments that appear in Table 2 are consistent with the 2D structure that was proposed based upon the NMR data.

In order to determine the 3D structure of the compound, a standard Marfey's analysis was employed. Preparation of the Marfey's standards was accomplished by reaction of all the amino acids believed to be in the structure of the compound of Formula II in an array fashion with L-FDLA, using the conditions shown in Scheme 5, as derived from Bhusan, R.; Brückner, H. *Amino Acids* 2004, 27, 247, the teachings of which are incorporated herein by reference.

Scheme 5

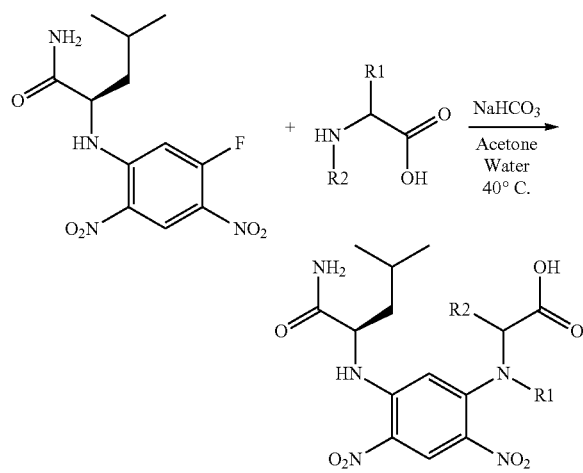

The amino acids used were: L-isoleucine, D-isoleucine, Allo-L-isoleucine, Allo-D-isoleucine, L-serine, D-serine, L-glutamic acid, D-glutamic acid, N-methyl-L-phenylalanine, N-methyl-D-phenylalanine, L-alanine, D-alanine, L-threonine, D-threonine, Allo-L-threonine, Allo-D-threonine and all four diastereomers of enduracididine. In addition, the Marfey's standards of the two separate mixtures of L- and L-Allo-enduracididine, and D- and D-Allo-enduracididine, synthesized as described below were prepared. Hydrolysis of the compound of Formula (II) followed by isolation of peptidic fragments allowed for further Marfey's analysis to determine the stereochemistry and position of the isoleucines and serines.

(2S, 4R) as the Major Diastereomer of a 6:1 Mixture with (2S, 4S) as the Minor Diastereomer)

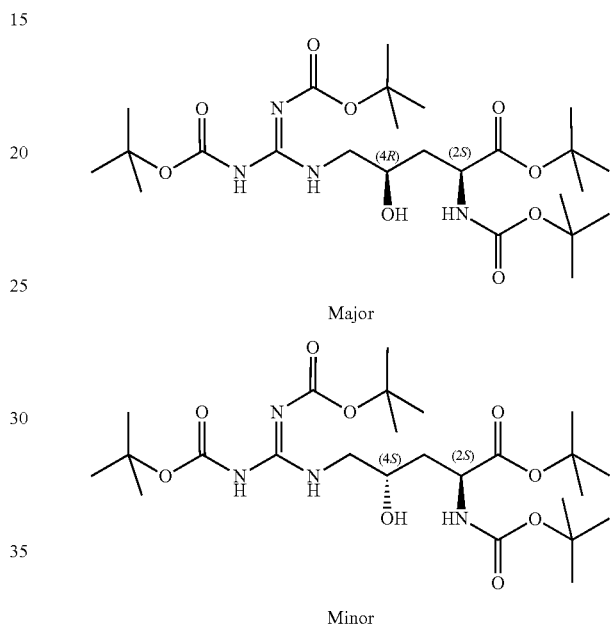

To (2S,4R)-2-tert-Butoxycarbonylamino-4-hydroxy-5-nitro-pentanoic acid tert-butyl ester (2.3 g, 6.9 mmol) in anhydrous methanol (30 mL), at room temperature and under an atmosphere of nitrogen, was added ammonium formate (4.4 g, 69 mmol) and 10% palladium on carbon (735 mg, 0.7 mmol). The reaction was heated to 40° C. for 1 hour, cooled and filtered through celite. The filtrate was concentrated in vacuo to afford an oily residue that was dissolved in ethyl acetate. The organic layer was washed with a saturated aqueous solution of sodium bicarbonate, which was back extracted with ethyl acetate. The combined ethyl acetate layers were combined, dried through a hydrophobic frit and concentrated in vacuo. The resulting oil was immediately dissolved in anhydrous acetonitrile and at room temperature and under an atmosphere of nitrogen, was added 1-H-(pyrazole)-1-N-tertbutoxycarbonyl carboxamidine (2.1 g, 10.4 mmol). The reaction was stirred for 20 hours before being concentrated in vacuo. The residue was purified by silica gel chromatography using iso-hexanes/ethyl acetate (5/1) as eluent to afford the title compound as a viscous oil (2.1 g, 56%, 3 steps from Boc-Asp-OtBu). LCMS (m/z) =547.3 [M+H], Tr=3.45 min. $^1$H NMR (300 MHz, CDCl$_3$) δ 1.39-1.55 (m, 36H), 1.81-2.01 (m, 2H), 3.37-3.49 (m, 1H), 3.56-3.66 (m, 1H), 3.88-4.01 (m, 1H), 4.19-4.30 (m, 1H), 5.19-5.30 (m, 1H), 5.38-5.52 (m, 1H), 8.67-8.78 (m, 1H), 11.45 (s, 1H).

(S)-5-((S)-2-tert-Butoxycarbonyl-2-tert-butoxycarbonylamino-ethyl)-2-[(E)-tert-butoxycarbonylimino]-imidazolidine-1-carboxylic acid tert-butyl ester (Major Diastereomer of a 6:1 Mixture with (2S, 4R) as the Minor Diastereomer)

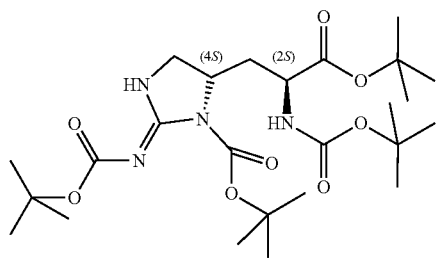

Major

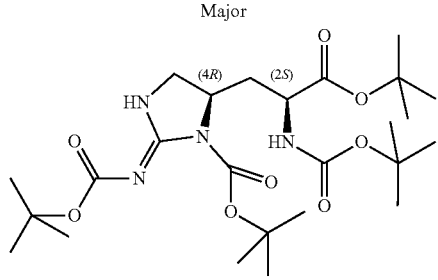

Minor

A solution of (2S,4R)-2-tert-Butoxycarbonylamino-4-hydroxy-5-nitro-pentanoic acid tert-butyl ester (900 mg, 1.7 mmol) in anhydrous dichloromethane (63 mL) was cooled to −78° C. and under an atmosphere of nitrogen was added N—N'-diisopropylethylamine (1.5 mL, 8.2 mmol). This was followed by the dropwise addition of trifluoromethane sulfonic anhydride (0.3 mL, 1.8 mmol), maintaining the temperature below −76° C. Following the addition the reaction was stirred at −78° C. for 4 hours and then warmed to 0° C. and quenched with a saturated aqueous solution of sodium bicarbonate. The organic layer was separated, washed with 1M HCl (1×), dried through a hydrophobic fit and concentrated in vacuo. The residue was purified by silica gel chromatography using iso-hexanes/ethyl acetate (1/2 then 0/1) as eluent to afford the title compound as a viscous oil (740 mg, 85%). LCMS (m/z)=529.5 [M+H], Tr=2.38 min. $^1$H NMR (300 MHz, CDCl$_3$) δ 1.38-1.66 (m, 36H), 1.87-2.02 (m, 1H), 2.14-2.34 (m, 1H), 3.60-3.84 (m, 1H), 3.91-4.09 (m, 1H), 4.21-4.35 (m, 1H), 4.38-4.60 (m, 1H), 5.09-5.29 (m, 1H).

(2S, 4S)-Enduracididine Trifluoroacetic Acid Salt (Major Diastereomer of a 6:1 Mixture with (2S, 4R) as the Minor Diastereomer).

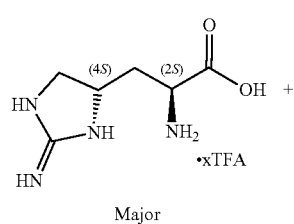

Major

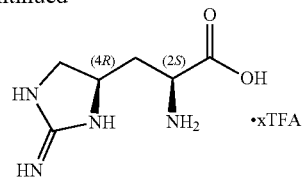

Minor

A solution of (S)-5-((S)-2-tert-Butoxycarbonyl-2-tert-butoxycarbonylamino-ethyl)-2-[(E)-tert-butoxycarbonylimino]-imidazolidine-1-carboxylic acid tert-butyl ester (740 mg, 1.4 mmol) in trifluoroacetic acid (20 mL) and water (7 mL) was stirred at room temperature for 20 hours. The reaction was concentrated in vacuo and the resultant residue co-evaporated from toluene (3×). The viscous oil was dried on a vacuum for 24 hours and the resulting solid triturated in diethyl ether. The solid was filtered and dried to afford the title compound as an off-white solid (600 mg, 83%). LCMS (m/z)=173.3 [M+H], Tr=0.22 min. $^1$H NMR (300 MHz, D$_2$O) δ 1.99-2.13 (m, 1H), 2.20-2.33 (m, 1H), 3.34-3.43 (m, 1H), 3.83 (t, J=9.8 Hz, 1H), 3.96 (t, J=6.9 Hz, 1H), 4.17-4.31 (m, 1H).

(2R, 4R)-Enduracididine Trifluoroacetic Acid Salt (Major Diastereomer of a 6:1 Mixture with (2R, 4S) as the Minor Diastereomer).

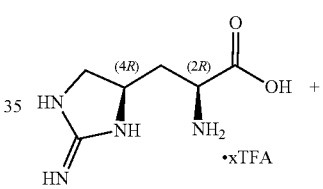

Major

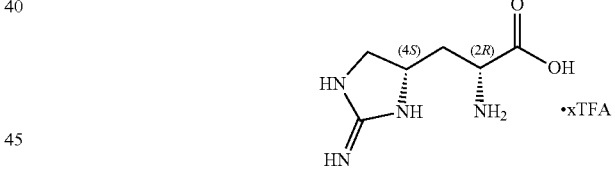

Minor (2R, 4R)-Enduracididine trifluoroacetic acid salt was prepared, as the major diastereomer of a 6:1 mix with the minor (2R, 4S) diastereomer, in like fashion to (2S, 4S)-Enduracididine trifluoroacetic acid salt Example 2: Antibacterial Spectrum A compound of Formula (II), prepared in accordance with Example 1, was subjected to a panel of bacterial species. The antibacterial spectrum of the compound is shown in Table 3. Addition of 10% serum had no effect on the minimum inhibitory concentration (MIC). As indicated by the data presented in Table 3, the compound has excellent activity against Gram-positive pathogens, including resistant strains. The compound also has low potency against most Gram-negative bacteria, and good activity against *H. influenzae*, opening a possibility for treating respiratory tract infections.

TABLE 3

Antibacterial activity of a compound of Formula (II)

| Strain | MIC (µg/mL) |
|---|---|
| *Staphylococcus aureus* | |
| ATCC 29213 (MSSA) | 0.16-0.63 |
| NCTC 8325 (MSSA) | 0.08-0.31 |
| ATCC 33591 (MRSA) | 0.16-0.31 |
| NRS54 (MRSA) | 0.078-0.16 |
| NRS108 (MRSA, also synercid[R]) | 0.16 |
| NRS269 (MRSA, also tigecycline[R]) | 0.16-0.31 |
| ATCC 700699 (GISA) | 0.31 |
| *S. epidermidis* | |
| ATCC 35984 = NRS101 (mecA positive) | 0.078-0.16 |
| NRS8 (mecA positive) | 0.16-0.31 |
| NRS34 (mecA positive) | 0.16 |
| *S. haemolyticus* | |
| NRS9 (mecA positive) | 0.08 |
| NRS69 (mecA positive) | 0.16 |
| Other Gram-positive | |
| *Streptococcus pneumoniae* ATCC BAA 255 | 0.05 |
| *Streptococcus pneumoniae* VL-172 | 0.15 |
| *Streptococcus pneumoniae* VL-190 | 0.15 |
| SPN GSK 1629 (ATCC 10813) | 0.08 |
| SPN 6303 | 0.04 |
| SPN BAA 1407 | 0.02-0.04 |
| *Streptococcus pyogenes* ATCC19615 | 0.31 |
| *S. warneri* NRS138 | 0.02 |
| *Bacillus anthracis* Sterne | 0.02 |
| *Bacillus subtilis* 1A1 | 0.02 |
| *Clostridium difficile* | 0.005 |
| *Propionibacterium acnes* | 0.078 |
| Vancomycin-resistant *Enterococcus* | |
| VRE *faecium* BM4147 (aac (6')-le-aph(2")) | 0.31 |
| VSE *faecium* E4sol | 0.31 |
| VRE *faecalis* ATCC 51575 | 0.31-0.63 |
| *E. faecalis* M192 (vancomycin sensitive) | 0.63 |
| *Mycobacterium* | |
| *Mycobacterium smegmatis* mc$^2$155 | 0.31 |
| *M. tuberculosis* mc$^2$6020 (ΔlysA, ΔpanCD) | 1.25 |
| *M. tuberculosis* H37Rv | 0.125 |
| *M. tuberculosis* (clinical isolate 70) | 0.125 |
| *M. tuberculosis* (clinical isolate 76) | 0.125-0.25 |
| *M. tuberculosis* (clinical isolate 82) | 0.125-0.25 |
| *M. tuberculosis* (clinical isolate 102) | 0.25 |
| Gram-negative | |
| *Haemophilus influenzae* SJ7 | 2.5 |
| *Klebsiella pneumoniae* ATCC 700603 | 20 |
| *Pseudomonas aeruginosa* PA-01 | >100 |
| *E. coli* K12 | 12.5 |
| *E. coli* W0153 (AB1157; asmB1 ΔtolC::kan) | 2.5 |
| *E. coli* W0159 (AB1157; asmB1 ΔrfaC::kan) | 2.5 |
| *E. coli* ATCC 25922 | 12.5 |
| *E. coli* mutS | 12.5 |
| *Klebsiella pneumoniae* ATCC 43816 | >40 |
| *Yersinia pestis* KIM 100 deletion pDC1 | 50-100 |
| *Neisseria gonorrhoeae* | 25 |
| *Bacteriodes fragilis* | 200 |

In addition, to date no mutants of *S. aureus* that are resistant to compounds of Formula (II) have been identified. Data indicates that the resistance frequency is <10$^{-10}$ (tested at 4×MIC). No detectable resistance after 17 days of serial passaging was observed.

The compound of Formula (II) was then tested (at Micromyx, Kalamazoo, Michigan) against 255 contemporary clinical isolates including linezolid, vancomycin, and daptomycin resistant/less-sensitive strains. The results of these experiments are summarized in Tables 4-6 below:

TABLE 4

Comparision of antibacterial activity of a compound of Formula (II) against Evaluated Gram-Positive Pathogens (MIC µg/mL)

| Organism | Drug | MIC Range | MIC$_{50}$ | MIC$_{90}$ | % S[1] |
|---|---|---|---|---|---|
| *Staphylococcus aureus* MSSA (n = 20) | Formula (II) | 0.06-0.25 | 0.25 | 0.25 | — |
| | Linezolid | 2-4 | 2 | 4 | 100.0 |
| | Vancomycin | 0.5-1 | 0.5 | 1 | 100.0 |
| | Daptomycin | 0.12-0.25 | 0.25 | 0.25 | 100.0 |
| *Staphylococcus aureus* MRSA (n = 20) | Formula (II) | 0.06-0.5 | 0.12 | 0.25 | — |
| | Linezolid | 2-4 | 2 | 4 | 100.0 |
| | Vancomycin | 0.5-2 | 0.5 | 1 | 100.0 |
| | Daptomycin | 0.12-0.25 | 0.25 | 0.25 | 100.0 |
| *Staphylococcus aureus* VISA (n = 10) | Formula (II) | 0.12-1 | 0.25 | 0.5 | — |
| | Linezolid | 1-4 | 2 | 2 | 100.0 |
| | Vancomycin | 1-8 | 4 | 8 | 10.0 |
| | Daptomycin | 0.25-1 | 0.5 | 1 | 100.0 |
| *Staphylococcus aureus* Daptomycin$^{NS}$ (n = 5) | Formula (II) | 0.12-0.5 | — | — | — |
| | Linezolid | 1-32 | — | — | 80.0 |
| | Vancomycin | 0.5-8 | — | — | 40.0 |
| | Daptomycin | 2-8 | — | — | 0.0 |
| *Staphylococcus aureus* Linezolid$^R$ (n = 5) | Formula (II) | 0.12-0.5 | — | — | — |
| | Linezolid | 16->32 | — | — | 0.0 |
| | Vancomycin | 1 | — | — | 100.0 |
| | Daptomycin | 0.25-0.5 | — | — | 100.0 |
| *Staphylococcus epidermidis* (n = 20) | Formula (II) | ≤0.03-0.25 | 0.12 | 0.12 | — |
| | Linezolid | 1-4 | 2 | 2 | 100.0 |
| | Vancomycin | 1-2 | 2 | 2 | 100.0 |
| | Daptomycin | 0.06-0.25 | 0.12 | 0.25 | 100.0 |
| *Enterococcus faecalis* (n = 10) 50% VRE | Formula (II) | 0.5-1 | 0.5 | 0.5 | — |
| | Linezolid | 1-2 | 2 | 2 | 100.0 |
| | Vancomycin | 0.5->32 | 1 | >32 | 50.0 |
| | Daptomycin | 0.12-8 | 0.25 | 0.5 | 90.0 |
| *Enterococcus faecium* (n = 10) 50% VRE | Formula (II) | 0.25-1 | 0.5 | 1 | — |
| | Linezolid | 1-2 | 2 | 2 | 100.0 |
| | Vancomycin | 0.5->32 | 0.5 | >32 | 50.0 |
| | Daptomycin | 0.5-1 | 0.5 | 1 | 100.0 |
| *Streptococcus pneumoniae* (n = 20) 28.6% PSSP 33.3% PISP 38.1% PRSP | Formula (II) | ≤0.03-0.06 | ≤0.03 | ≤0.03 | — |
| | Linezolid | 0.25-1 | 1 | 1 | 100.0 |
| | Vancomycin | 0.12-0.5 | 0.25 | 0.25 | 100.0 |
| | Daptomycin | ≤0.03-0.06 | ≤0.03 | ≤0.03 | — |
| *Streptococcus pyogenes* (n = 10) | Formula (II) | ≤0.03-0.06 | ≤0.03 | 0.06 | — |
| | Linezolid | 0.5-1 | 1 | 1 | 100.0 |
| | Vancomycin | 0.25 | 0.25 | 0.25 | 100.0 |
| | Daptomycin | ≤0.03-0.06 | ≤0.03 | 0.06 | 100.0 |
| *Streptococcus agalactiae* (n = 10) | Formula (II) | 0.06-0.12 | 0.12 | 0.12 | — |
| | Linezolid | 0.5-2 | 1 | 1 | 100.0 |
| | Vancomycin | 0.25-0.5 | 0.5 | 0.5 | 100.0 |
| | Daptomycin | 0.06-0.25 | 0.12 | 0.12 | 100.0 |
| Viridans Group Streptococci[2] (n = 5) | Formula (II) | ≤0.03-0.12 | — | — | — |
| | Linezolid | 0.5-1 | — | — | 100.0 |
| | Vancomycin | 0.25-0.5 | — | — | 100.0 |
| | Daptomycin | 0.06-0.25 | — | — | 100.0 |

[1]CLSI criteria applied for interpretation of % susceptible
[2]one isolate each of *S. sanguis*, *S. mitis*, *S. anginosus*, *S. intermedius*, and *S. salivarius*
PISP: penicillin-intermediate *S. pneumoniae*,
PRSP: penicillin-resistant *S. pneumoniae*

TABLE 5

Comparision of antibacterial activity of a compound of Formula (II) against Ciprofloxacin MICs (µg/mL) Against Evaluated Enterobacteriaceae

| Organism | Drug | MIC Range | MIC$_{50}$ | MIC$_{90}$ | % S[1] |
|---|---|---|---|---|---|
| *Escherichia coli* (n = 10) 40% ESBL | Formula (II) | 32->32 | >32 | >32 | — |
| | Ciprofloxacin | 0.008->32 | 32 | >32 | 20.0 |
| *Klebsiella pneumoniae* (n = 10) 30% KPC | Formula (II) | >32 | >32 | >32 | — |
| | Ciprofloxacin | 0.03->32 | 0.25 | >32 | 50.0 |

TABLE 5-continued

Comparision of antibacterial activity of a compound
of Formula (II) against Ciprofloxacin MICs (µg/mL)
Against Evaluated Enterobacteriaceae

| Organism | Drug | MIC Range | MIC$_{50}$ | MIC$_{90}$ | % S[1] |
|---|---|---|---|---|---|
| Proteus spp.[3] | Formula (II) | >32 | >32 | >32 | — |
| (n = 10) | Ciprofloxacin | 0.015-1 | 0.015 | 0.06 | 100.0 |
| Enterobacter | Formula (II) | >32 | >32 | >32 | — |
| spp.[2] | Ciprofloxacin | 0.015-0.12 | 0.015 | 0.06 | 100.0 |
| (n = 10) | | | | | |
| Serratia | Formula (II) | >32 | >32 | >32 | — |
| marcescens | Ciprofloxacin | 0.03-1 | 0.06 | 1 | 100.0 |
| (n = 10) | | | | | |

[1]CLSI criteria applied for interpretation of % susceptible
[2]E. cloacae (n = 5), E. aerogenes (n = 5)
[3]P. mirabilis (n = 5), P. vulgaris (n = 5)
ESBL: extended-spectrum beta-lactamase positive

TABLE 6

Comparision of antibacterial activity of a compound
of Formula (II) against Ciprofloxacin MICs (µg/mL)
Against Evaluated non-Enteric Gram-Negative Pathogens

| Organism | Drug | MIC Range | MIC$_{50}$ | MIC$_{90}$ | % S[1] |
|---|---|---|---|---|---|
| Pseudomonas | Formula (II) | >32 | >32 | >32 | — |
| aeruginosa | Ciprofloxacin | 0.06->32 | 1 | 32 | 50.0 |
| (n = 10) | | | | | |
| 30% MDR | | | | | |
| Acinetobacter | Formula (II) | 32->32 | 32 | >32 | — |
| baumannii | Ciprofloxacin | 0.12->32 | >32 | >32 | 20.0 |
| (n = 10) | | | | | |
| 80% MDR | | | | | |
| Haemophilus | Formula (II) | 4-32 | 8 | 16 | — |
| influenzae | Ciprofloxacin | 0.004-0.25 | 0.008 | 0.008 | 100.0 |
| (n = 20) | | | | | |
| 25% Ampicillin$^R$ | | | | | |
| Moraxella | Formula (II) | 1-2 | 1 | 2 | — |
| catarrhalis | Ciprofloxacin | 0.015-0.06 | 0.03 | 0.06 | 100.0 |
| (n = 20) | | | | | |

[1]CLSI criteria applied for interpretation of % susceptible
MDR: multi-drug resistant, AmpicillinR: ampicillin-resistant The compound of Formula (II) was tested against ten B. anthracis isolates in the BL-3 facility at Southern Research Institute. Screening was accomplished by use of a microdilution (96-well) broth based minimal inhibitory concentration (MIC) assay and included the following isolates of *Bacillus anthracis*: NR-36, NR-38, NR-41, NR-46, NR-411, NR-412, NR-413, NR-414, NR-415, and NR-3838. First, Mueller-Hinton Broth containing 0.05% Tween-80 was added to each well. Test compounds, diluted In Mueller-Hinton Broth containing 0.05% Tween-80 were subsequently added (0.1 mL/well) to appropriate wells at twice the intended starting concentration and serially diluted two-fold across the plate for a total of 12 concentrations (128-0.06 μg/mL). The plates were then inoculated (0.1 ml/well) with a targeted concentration of $1.0\times10^6$ CFU/mL pathogen diluted in Mueller-Hinton Broth containing 0.05% Tween-80 and incubated overnight (16-20 hours). Following incubation, the plates were read visually and individual wells scored for turbidity, partial clearing or complete clearing. Testing was conducted in duplicate and the following controls were included in each test plate: i) medium only (sterility control); ii) organism in medium (negative control); and iii) doxycycline (positive control). The MIC is reported as the lowest concentration (μg/mL) of drug that visually inhibited growth of the organism (Table 3). The compound was highly active, with broth $MIC_{90}$s=0.125-≤0.06 μg/mL, and performed better than the comparator drug doxycycline (see Table 7).

TABLE 7

| Organism | MIC (ug/mL) Formula (II) | Doxycycline |
|---|---|---|
| *B. anthracis* NR-36 | ≤0.06 | 0.06 |
| *B. anthracis* NR-38 | ≤0.06 | 0.125 |
| *B. anthracis* NR-41 | ≤0.06 | 0.06 |
| *B. anthracis* NR-46 | ≤0.06 | 0.125 |
| *B. anthracis* NR-411 | ≤0.06 | 0.125 |
| *B. anthracis* NR-412 | 0.125-0.06[a] | 0.03 |
| *B. anthracis* NR-413 | 0.125 | 0.06 |
| *B. anthracis* NR-414 | ≤0.06 | 0.125 |
| *B. anthracis* NR-415 | ≤0.06 | 0.06 |
| *B. anthracis* NR-3838 | ≤0.06 | 0.06 |

[a]The MIC lies somewhere between the two values given due to partial clearing in wells at 0.125 μg/mL and full clearing in wells at 0.06 μg/mL

Example 3: Cytotoxicity Activity, Hemolytic Activity, DNA Binding, hERG Inhibition, Cytochrome P450 Inhibitory Activity, Genotoxicity, Plasma Stability, Protein Binding

Cytotoxicity Activity

Cultures of NIH3T3 mouse embryonic fibroblast (ATCC CRL-1658, in Dulbecco's Modified Eagle's medium supplemented with 10% bovine calf serum) and Hep-G2 (ATCC HB-8065TM, in Dulbecco's Modified Eagle's medium supplemented with 10% fetal calf serum) were grown for 3 days at 5% CO2 in air, 37° C., humidified. The cultures were trypsinized, counted and seeded into the wells of sterile 96-well flat bottom plate (1500 cells/well/100 μL for NIH3T3, and 4000 cells/well/100 μL for Hep-G2). After 24 hours, the media in each well were replaced with 100 μL of fresh media (containing a two-fold serial dilution of a compound of Formula (II) prepared in accordance with Example 1 from 0.8 μg/mL to 100 μg/mL, and a no compound control) that had been incubated for 2 hours at 5% CO2 in air, 37° C., humidified. After another 48 hours of incubation at 5% CO2 in air, 37° C., humidified, a 20 μL of reporter (Promega CellTiter 96® AQueous One Solution Cell Proliferation Assay) was added to the cells. After 2 hours of incubation, the plates were read at 490 nm using the Spectramax Plus Spectrophotometer. Viable cells will be able to reduce the reporter while dead cells cannot. The results showed that there was no loss of viability in NIH3T3 and Hep-G2 days after two days of incubation with a compound of Formula (II) tested up to a concentration of 100 μg/mL.

Hemolytic Activity

Fresh human red blood cells were washed with phosphate buffered saline (PBS) until the upper phase after centrifugation was clear (no detectable red color by eye). The pellet was resuspended to a final OD600 of 24 in PBS, and added to the wells of sterile 96-well U-bottom plate (99 μL per well). A compound of Formula (II) was two-fold serially diluted in water supplemented with 0.05% Tween and a 1 μL from each concentration added to the wells resulting in a final concentration tested ranging from 0.003 to 200 μg/mL of a compound of Formula (II). After 1 hour at 37° C., the cells are centrifuged at 1000×g for 5 minutes at 4° C. A 10 μL of the supernatant is removed and added to 90 μL/well of PBS (in a 96 well plate). The contents in the well are mixed and the plate at 450 nm using the Spectramax Plus Spectrophotometer. The results showed that there was no detectable hemolysis after 1 hour of incubation with a compound of Formula (II) tested up to a concentration of 200 μg/mL.

DNA Binding

A compound of Formula (II) was two-fold serially diluted in water supplemented with 0.05% Tween (from concentration of 2.5 mg/mL to 4.9 µg/mL). A 3 µl volume of the serial concentration of a compound of Formula (II) was added to (a) 6 µl of sheared salmon sperm DNA (10 mg/mL, sheared by syringing 20 times through a 20 Gauge needle) or (b) 6 µL of water. Control compounds were similarly treated. Actinomycin D was used as a positive control compound as it is known to be bound to DNA while vancomycin was used as a negative compound as it is known not to bind to DNA. After mixing well, a 7.5 µL volume was spotted onto a lawn of growing *Staphylococcus aureus* NCTC 8325 cells. The zones of growth inhibition around the spots are measured after 16 hours of growth at 37° C. A decrease in the inhibition zone size indicates loss of antibacterial activity due to binding to the DNA. For example, the activity of 1 µg of Actinomycin D was eliminated by the presence of 50 µg of DNA while there was no effect of DNA on the activity of vancomycin. The results showed that there was no loss of growth inhibition for the compound of Formula (II) due to the presence of DNA (6.6 µg/µL), indicating that the compound of Formula (II) does not bind DNA.

hERG Inhibition

The compound of Formula (II) also exhibited negligible inhibition against hERG in an in vitro patch-clamp assay [$IC_{50}$>100 µg/mL (~1,000×MIC)].

Briefly, the experiments were performed on an IonWorks™ HT instrument (Molecular Devices Corporation), which automatically performs electrophysiology measurements in 48 single cells simultaneously in a specialized 384-well plate (PatchPlate™). The cells used were Chinese hamster ovary (CHO) cells stably transfected with hERG. A single-cell suspension is prepared in extracellular solution (Dulbecco's phosphate buffered saline with calcium and magnesium pH 7-7.2) and aliquots added automatically to each well of a PatchPlate™. The cells were then positioned over a small hole at the bottom of each well by applying a vacuum beneath the plate to form an electrical seal. The vacuum was applied through a single compartment common to all wells which is filled with intracellular solution (buffered to pH 7.2 with HEPES). The resistance of each seal was measured via a common ground-electrode in the intracellular compartment and individual electrodes placed into each of the upper wells. Electrical access to the cell was achieved by circulating a perforating agent, amphotericin, underneath the PatchPlate™ and then measuring the pre-compound hERG current. An electrode was positioned in the extracellular compartment and a holding potential of −80 mV applied for 15 sec. The hERG channels were then activated by applying a depolarizing step to +40 mV for 5 sec and then clamped at −50 mV for 4 sec to elicit the hERG tail current, before returning to −80 mV for 0.3 s.

The test compound was then added at various concentrations (0.008, 0.04, 0.2, 1, 5 and 25 µM) to the upper wells of the PatchPlate™. The test compound was left in contact with the cells for 300 sec before recording currents using the same voltage-step protocol as in the pre-compound scan. Quinidine, an established hERG inhibitor, was included as a positive control.

Post-compound currents were expressed as a percentage of pre-compound currents and plotted against concentration for each compound. Where concentration-dependent inhibition was observed, the data are fitted to the following equation and the $IC_{50}$ value calculated:

$$y = \frac{y_{max} - y_{min}}{1 + (x/x_{50})^s} + y_{min}$$

Where y=(post-compound current/pre-compound current)× 100, x=concentration, $x_{50}$=concentration required to inhibit current by 50% ($IC_{50}$) and s=slope of the graph.

TABLE 8 hERG Inhibition Results

| Compound | IC50 (µM) | n | Comments |
|---|---|---|---|
| Formula (II) | >100 | 13 | 41.8% inhibition at 100 µM |
| Quinidine | 1.44 | 8 | Positive control |

Cytochrome P450 Inhibitory Activity

The compound of Formula (II) was then tested for cytochrome P450 inhibitory activity, Briefly, liver microsomes were incubated with the compound at 37° C. at 10 and 30 µM in triplicate. Control incubations containing vehicle or reference inhibitors were run alongside the test agents. The final assay contained test agent, probe substrates at the indicated concentration, 2 mM NADPH, 3 mM $MgCl_2$ in 50 mM potassium phosphate buffer, pH 7.4. The final microsomal concentration was 0.5 mg/mL. The maximum solvent concentration in the final assay was ≤0.5% to minimize the inhibition of cytochromes by solvent. NADPH was added last to start the assay. At the end of ten minutes incubation, the assay was stopped by the addition of acetonitrile containing internal standard, the samples were centrifuged, and the amount of probe metabolite in the supernatant was determined by LC/MS/MS. The following probe substrate, probe metabolite and control inhibitors were used to perform and validate the assays. (Table 9).

TABLE 9

Cyp assay substrates and control inhibitors

| Cyp | Probe substrate | Probe substrate concentration (µM) | Probe metabolite | Control inhibitor |
|---|---|---|---|---|
| Cyp1A2 | phenacetin | 10 | acetaminophen | α-naphthoflavone |
| Cyp2C9 | tolbutamide | 100 | hydroxytolbutamide | sulphaphenazole |
| Cyp2C19 | S-mephenytoin | 50 | hydroxymephenytoin | ticlopidine |
| Cyp2D6 | dextromethorphan | 1 | dextrorphan | quinidine |
| Cyp3A4/5 | testosterone | 100 | 6β-hydroxytestosterone | ketoconazole |
| Cyp3A4/5 | midazolam | 2 | hydroxymidazolam | ketoconazole |

The results for testing the compound of Formula (II) are shown in Table 10:

TABLE 10

Compound of formula (II): % inhibition compared to vehicle

| Client ID | Test Conc. | CYP3A4-Midazolam | CYP3A-Testosterone | CYP2C9 | CYP2D6 | CYP2C19 | CYP1A2 |
|---|---|---|---|---|---|---|---|
| Formula | 30 µM | 17.3% | 28.4% | 7.4% | 33.5% | 3.2% | 0.0% |
|  | 10 µM | 13.7% | 16.1% | 14.8% | 32.9% | 3.9% | 3.6% |

The control compounds performed as expected (Table 11).

TABLE 11

Control compounds: % inhibition compared to vehicle

| | CYP3A4-Modazolam | CYP3A4-Testoterone | CYP2C9 | CYP2D6 | CYP2C19 | CYP1A2 |
|---|---|---|---|---|---|---|
| | | | Controls | | | |
| | Ketoconazole[a] | ketoconazole[a] | sulpha-phenazole[a] | quinindine[a] | ticlopidine[b] | α-naphtho-flavone[a] |
| Conc. 1 | 95.8% | 96.8% | 87.5% | 91.7% | 93.5% | 72.4% |
| Conc. 2 | 69.0% | 75.2% | 55.6% | 60.6% | 51.9% | 45.3% |

[a]tested at conc.1 (1 μM) and conc. 2 (0.1 μM)
[b]tested at conc.1 (10 μM) and conc. 2 (1 μM)

In summary, 10 μM (~40×MIC), the compound of Formula (II) showed less than 16% inhibition against five of the six CYP isozymes tested and 32.9% inhibition against CYP2D6

Genotoxicity

The compound of Formula (II) was then tested for genotoxicity potential in a standard in vitro micronucleus test. Briefly, the in vitro micronucleus test employs fluorescent cell imaging to assess cytotoxicity and quantification of micronuclei, a well-accepted model to test for genotoxic carcinogens. The assay was run with CHO-K1 cells in the presence or absence of Aroclor-treated rat liver S9 fraction, with compound tested over a ten point concentration range (0.004, 0.01, 0.04, 0.1, 0.4, 1.0, 4.0, 10, 40, 100 μM) in duplicate. No genotoxicity was observed for the compound of Formula (II) up to 100 μM (~400×MIC) in an in vitro micronucleus test (+/−S9).

No genotoxic potential was observed for the compound of Formula (II) when evaluated in silico against a battery of predictive models comprised of the following endpoints: Salmonella mutagenicity, E. coli mutagenicity, mouse lymphoma, in vitro chromosome aberrations, and in vivo micronucleus. This computational assessment was based on Quantitative Structure Activity Relationship predictions performed using the Leadscope® Model Applier and Leadscope® Toxicity Databases (Leadscope Inc., Columbus, Ohio). Briefly, The genetic toxicity QSAR models were constructed at the US Food and Drug Administration (FDA) Center for Drug Evaluation and Research (CDER) by the Informatics and Computational Safety Analysis Staff (IC-SAS). The models were built using the Leadscope Prediction Data Miner (PDM) software using all default settings. Most of the QSAR models were built from public information and include the training set structures and conclusions as part of the model description. The QSAR models are trained with molecular descriptors that include structural features and 8 calculated properties. The structural features include Leadscope default hierarchy features (Leadscope features) plus the predictive scaffolds generated with default settings [4,5]. The eight calculated properties are; parent molecular weight, a Log P, polar surface area, hydrogen bond acceptors, hydrogen bond donors, number of rotational bonds and Lipinski score (rule violation count).

Plasma Stability

The compound of Formula (II) was then tested for plasma stability. A sensitive bioanalytical method was first developed for detecting the compound of Formula (II) in plasma using HPLC coupled to a triple quadrupole mass spectrometer. Plasma samples were spiked with the compound of Formula (II) at various concentrations, extracted with acetonitrile, and analyzed by LC/MS/MS. The low limit of quantification in plasma was 8.5 ng/mL. The compound of Formula (II) was then incubated at 5 μM in duplicate with the different plasma samples (mouse, rat, human and dog) at 37° C. At several time points, (0, 20, 40, 80, 120 minutes) an aliquot was removed from each experimental reaction and mixed with three volumes of ice-cold Stop Solution (methanol containing propranolol, diclofenac, or other internal standard). Stopped reactions were incubated at least ten minutes on ice. The samples were then centrifuged to remove precipitated protein, and the supernatants analyzed by LC/MS/MS to quantitate the remaining parent. In summary, the compound of Formula (II) exhibited a long (≥150 minutes) plasma half-life in plasma from all species tested.

Protein Binding

The compound of Formula (II) was then tested for protein binding by equilibrium dialysis. Briefly, the compound was first incubated at 5 μM with rat plasma. This mixture was then dialyzed in a RED Device (Pierce) (8,000 MW cutoff dialysis membrane) per the manufacturers' instructions against 5% dextrose (D5W), and incubated on a shaker. At the end of the incubation, aliquots from both plasma and D5W sides were collected, an equal amount of D5W was added to the plasma sample, and an equal volume of plasma was added to the D5W sample. Methanol (three volumes) containing internal standard was added to precipitate the proteins and release the agents. After centrifugation, the supernatant was transferred to a new plate and analyzed for the compound by LC/MS/MS. In summary, the compound exhibited 82-85% plasma protein binding.

Example 4: Microsomal Stability

The metabolic stability of a compound of Formula (II) was then measured in rat liver microsomes (Invitrogen/Life Technologies, CA) by monitoring the disappearance of the compound over a period of two hours. The compound was incubated with microsomes and samples taken at 0, 0.5 hr, 1 hr, and 2 hr. Samples were tested by growth inhibition of S. aureus and by LC/MS. After two hours, there was negligible decline of the compound, while verapamil, used as a positive control, degraded to its expected metabolites. No significant decrease in antibacterial activity or exstensive metabolite production was observed with the compound over the two hour period.

Example 5: Specificity of Action

Figure 7:
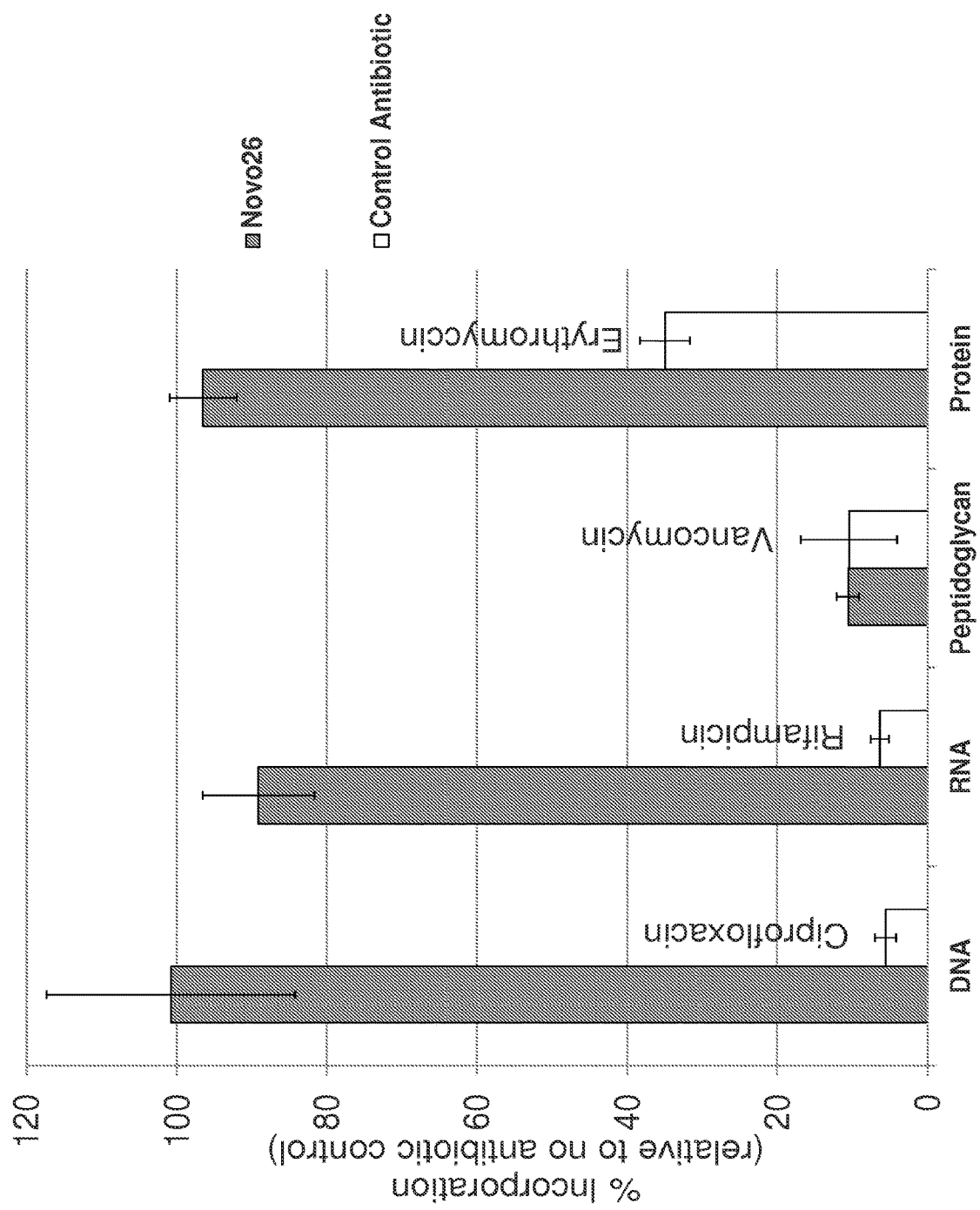
FIG. 7 is a graph depicting the effect of a compound of Formula (II) on macromolecular synthesis.

To provide insight into the mechanism and specificity of action of the compound of Formula (II), prepared in accordance with Example 1, a macromolecular synthesis study was performed with S. aureus. Incorporation of tritiated thymidine, uridine, leucine, or N-acetyl-glucosamine into DNA, RNA, protein, or peptidoglycan, respectively was measured, and the effect of the compound on the rate of biosynthesis was examined. Results indicated that the compound of Formula (II) strongly inhibited peptidoglycan synthesis, comparable to vancomycin (see FIG. 7).

Example 6: Mouse Septicemia Study

The compound of Formula (II) was tested against clinical isolate *S. aureus* MRSA ATCC 33591 in a mouse septicemia protection assay (see Frimodt-Moller, N., Knudsen, J. D. and Espersen, F. (1999) The mouse peritonitis/sepsis model. In: Zak, O., Sande, M. A. eds. *Handbook of animal model infection* San Diego: Academic Press, 127-136, the entire teachings of which are incorporated herein by reference) to assess its in vivo bioavailability and the protective dose resulting in 50% survival ($PD_{50}$) of infected mice after 48 hrs. CD-1 female mice were infected with 0.5 mL of bacterial suspension ($3.28 \times 10^7$ CFU/mouse) via intraperitoneal injection, a concentration that achieves at least 90% mortality within 48 hours after infection. At one hour post infection, mice were treated with the compound intravenously with single doses and the results are shown in Table 12. The compound of Formula (II) showed an excellent $PD_{50}$ of 0.19 mg/kg, comparing very favorably to that of vancomycin.

TABLE 12

$PD_{50}$ results

| Drug | Route | Dosing frequency | PD50 (mg/kg) | Confidence Interval |
|---|---|---|---|---|
| Cpd. of Formula (II) | IV | QD | 0.19 | 0.07-0.31 |
| Vancomycin | IV | QD | ~2.75 | — |

In summary, the compound showed an excellent 50% protective dose of 0.19 mg/kg compared to vancomycin (~2.75 mg/kg) in the mouse septicemia protection model. The compound gave complete protection at a dose of 0.5 mg/kg.

Example 7: In Vivo Efficacy: Mouse Thigh Infection Model

A compound of Formula (II), as prepared in Example 1, was then tested against MRSA in the neutropenic mouse thigh infection model. This model is an excellent system for measuring the effect of drug on the pathogen with most of the host immune system eliminated. The model is widely used to determine PK/PD parameters to estimate dosing. It is also a good model for acute bacterial skin and skin structure infections (ABSSSI), a potential clinical indication for the compound based on its antibacterial spectrum.

Female CD-1 mice were pre-treated with cyclophosphamide to render them neutropenic with two consecutive doses of 150 and 100 mg/kg delivered on 4 and 1 days prior to infection. Bacteria were re-suspended in sterile saline and adjusted to an OD of 0.1 at 625 nm (infection inoculum: $2.8 \times 10^5$ CFU/mouse). Mice were injected with the inoculum in the right thighs in a volume of 0.1 mL. At 2 hours post infection mice received treatment with the compound of Formula (II) at 1, 2.5, 5, 10, or 20 mg/kg administered in a single dose, intravenous injection. Four mice were treated per dose concentration. One group of infected mice were euthanized and thighs processed for CFUs to serve as the time of treatment controls (T=Rx). At 26 hours post infection mice were euthanized by $CO_2$ inhalation. The right thighs were aseptically removed, weighed, homogenized, serially diluted, and plated on trypticase soy agar. The plates were incubated overnight at 37° C. in 5% $CO_2$, and CFU per gram of thigh was determined (see Table 13).

TABLE 13

Antimicrobial action of a compound of Formula (II) in *S. aureus* thigh infection.

| Compound | Dose (mg/kg/day) | n | Log CFU/g of thigh | SD | Log change from control | Log change from T = Rx |
|---|---|---|---|---|---|---|
| T = Rx | — | 4 | 6.02 | 0.13 | — | — |
| None | — | 5 | 8.30 | 0.31 | — | — |
| Formula (II) | 20 | 4 | 4.44 | 0.16 | -3.86 | -1.58 |
| Formula (II) | 10 | 4 | 4.45 | 0.52 | -3.85 | -1.57 |
| Formula (II) | 5 | 4 | 4.49 | 0.12 | -3.81 | -1.53 |
| Formula (II) | 2.5 | 4 | 4.51 | 0.37 | -3.79 | -1.51 |
| Formula (II) | 1 | 4 | 6.20 | 1.78 | -2.1 | 0.18 |

The compound of Formula (II) significantly reduced pathogen load when dosed with a single IV injection at 2.5 mg/kg or higher.

The compound of Formula (II) was also tested in a thigh infection efficacy model (neutropenic mice) with MRSA as the infection agent. A higher than log CFU reduction from the starting infectious load was observed when dosed at 20, 10, 5, or 2.5 mg/kg (single dose iv in water). Infection was static at 1 mg/kg.

The foregoing data demonstrate safety and attractive mode of action with low resistance development—features that make the compound of Formula (II) an attractive lead for developing a therapeutic.

Example 8: In Vivo Efficacy: Mouse Pneumonia Model

The compound of Formula (II) was then evaluated against *Streptococcus pneumoniae* in an immunocompetent mouse pneumonia model to determine the compound's potential to treat acute respiratory infections. Briefly, CD-1 mice were infected intranasally with *Streptococcus pneumoniae* ATCC 6301(UNT012-2)($1.5 \times 10^6$ CFU/mouse). The compound was delivered intravenously at 24 and 36 hours post-infection, and at doses ranging from 0.5 to 10 mg/kg/dose. At 48 hours post infection, treated mice were euthanized, lungs aseptically removed and processed for CFU titers As seen in Table 14, the compound of Formula (II) was highly efficacious in this model, with a nearly 6-log CFU reduction at 48 hrs with 10 mg/kg/dose. A dose response relationship for the compound of Formula (II) was observed over the range of concentrations evaluated. The amount of the compound of Formula (II) required to achieve 1, 2, and 3 $\log_{10}$ CFU reductions was calculated to be 0.27, 0.48, and 0.75 mg/kg/dose, respectively [using Graph Pad Prizm (ver. 5.0f)]. A static dose of <0.5 mg/kg/dose was estimated for the compound of Formula (II).

TABLE 14

Antimicrobial action of Formula (II) in lung infection model

| Compound | Dose (mg/kg) | No. mice | Mean Log$_{10}$ CFU | SD | Log$_{10}$ change from 24 hrs | Log$_{10}$ change from 48 hrs |
|---|---|---|---|---|---|---|
| Formula (II) | 10 | 5 | 2.78 | 0.74 | −3.97 | −5.83 |
| Formula (II) | 5 | 5 | 3.11 | 1.08 | −3.64 | −5.5 |
| Formula (II) | 2.5 | 5 | 4.5 | 0.17 | −2.25 | −4.1 |
| Formula (II) | 1 | 5 | 4.69 | 1.45 | −2.07 | −3.92 |
| Formula (II) | 0.5 | 5 | 6.37 | 0.56 | −0.38 | −2.24 |
| Amoxicillin | 10 | 5 | 2.78 | 0.77 | −3.98 | −5.83 |
| Infection control-24 hr post infection | NA | 5 | 6.75 | 0.31 | NA | −1.86 |
| Infection control-48 hr post infection | NA | 5 | 8.61 | 0.46 | 1.86 | NA |

In a follow-up study, a dose response relationship for the compound of Formula (II) was observed over the range of concentrations evaluated (10, 5.0, 2.5, 1.0 and 0.5 mg/kg BID). The doses of the compound of Formula (II) required to achieve 1, 2, and 3 log$_{10}$ CFU reductions were determined to be 0.27, 0.48, and 0.75 mg/kg/dose, respectively. A static dose of <0.5 mg/kg/dose was estimated for the compound of Formula (II).

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

We claim:

1. A method of treating a bacterial infection in a subject in need thereof, the method comprising administering to the subject a pharmaceutical composition comprising a compound of Formula (II), or a tautomer or a pharmaceutically-acceptable salt thereof, and a pharmaceutically acceptable carrier; wherein the compound of Formula (II) is:

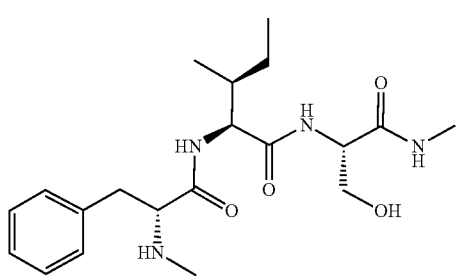

(II)

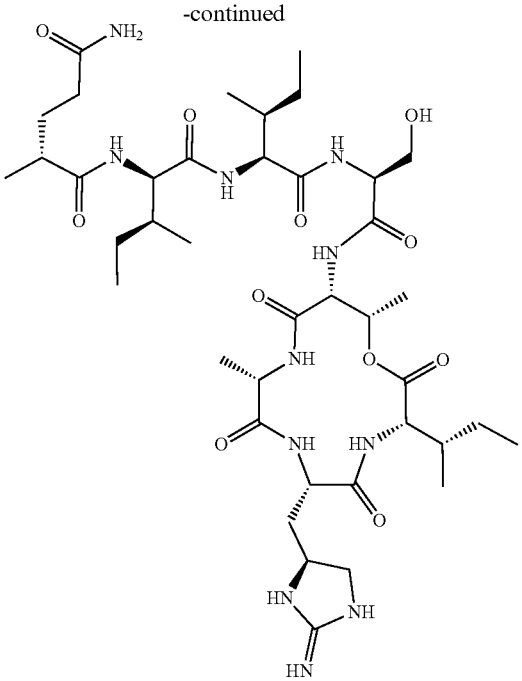

2. The method of claim 1, wherein the pharmaceutically acceptable carrier is selected from the group consisting of a sugar, a starch, a cellulose, an oil, a glycol, an alcohol, an ester, and a fatty acid ester of sorbitan.

3. The method of claim 1, wherein the pharmaceutically acceptable carrier is a sugar.

4. The method of claim 3, wherein the sugar is selected from the group consisting of lactose, glucose, and sucrose.

5. The method of claim 1, wherein the bacterial infection is caused by a Gram-positive bacterium.

6. The method of claim 5, wherein the Gram-positive bacterium is selected from the group consisting of *Streptococcus*, *Staphylococcus*, *Enterococcus*, *Corynebacteria*, *Listeria*, *Bacillus*, *Erysipelothrix*, *Mycobacterium*, *Clostridium*, and *Actinomycetales*.

7. The method of claim 5, wherein the Gram-positive bacterium is selected from the group consisting of methicillin-susceptible and methicillin-resistant staphylococci (including *Staphylococcus aureus*, *Staphylococcus epidermidis*, *Staphylococcus haemolyticus*, *Staphylococcus hominis*, *Staphylococcus saprophyticus*, and coagulase-negative staphylococci), glycopeptide intermediate-susceptible *Staphylococcus aureus* (GISA), penicillin-susceptible and penicillin-resistant streptococci (including *Streptococcus pneumoniae*, *Streptococcus pyogenes*, *Streptococcus agalactiae*, *Streptococcus dysgalactiae*, *Streptococcus avium*, *Streptococcus bovis*, *Streptococcus lactis*, *Streptococcus sangius*, *Streptococcus anginosus*, *Streptococcus intermedius*, *Streptococcus constellatus* and Streptococci Group C, Streptococci Group G and *Viridans streptococci*), enterococci (including vancomycin-susceptible and vancomycin-resistant strains such as *Enterococcus faecalis* and *Enterococcus faecium*), *Clostridium difficile*, *Clostridium clostridiiforme*, *Clostridium innocuum*, *Clostridium perfringens*, *Clostridium tetani*, *Mycobacterium tuberculosis*, *Mycobacterium avium*, *Mycobacterium intracellulare*, *Mycobacterium kansaii*, *Mycobacterium gordonae*, *Mycobacteria sporozoites*, *Listeria monocytogenes*, *Bacillus subtilis*, *Bacillus anthracis*, *Corynebacterium diphtherias*,

*Corynebacterium jeikeium, Corynebacterium sporozoites, Erysipelothrix rhusiopathiae*, and *Actinomyces israelli*.

8. The method of claim 7, wherein the bacterial infection is caused by *Bacillus anthracis*.

9. The method of claim 1, wherein the bacterial infection is caused by a Gram-negative bacterium.

10. The method of claim 9, wherein the Gram-negative bacterium is selected from the group consisting of *Helicobacter pylori, Legionella pneumophilia, Neisseria gonorrhoeae, Neisseria meningitidis*, pathogenic *Campylobacter sporozoites, Haemophilus influenzae, Pseudomonas aeruginosa, Enterobacter aerogenes, Enterobacter cloacae, Klebsiella pneumoniae, Klebsiella oxytoca, Pasteurella multocida, Bacteroides sporozoites, Bacteroides fragilis, Bacteroides thetaiotaomicron, Bacteroides uniformis, Bacteroides vulgatus Fusobacterium nucleatum, Streptobacillus moniliformis, Leptospira, Escherichia coli, Salmonella enterica, Salmonella salamae, Salmonella arizonae, Salmonella diarizonae, Salmonella houtenae, Salmonella bongori, Salmonella indica, Salmonella Enteritidis, Salmonella typhi*, and *Citrobacter freundii*.

11. A method of treating a bacterial infection in a subject in need thereof, the method comprising administering to the subject a pharmaceutical composition comprising a compound of Formula (III), or a tautomer or pharmaceutically-acceptable salt thereof, wherein the compound of Formula (III) is:

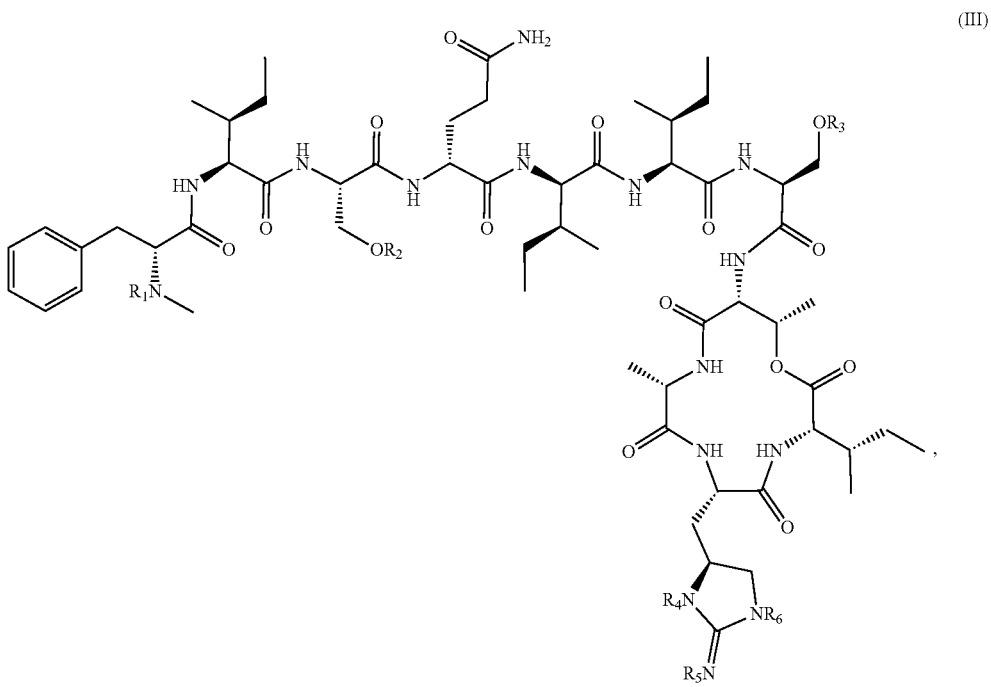

wherein each $R_1$-$R_6$ is independently selected from hydrogen, alkyl, alkenyl, alkynyl, cycloalkyl, cycloalkenyl, aryl, C(=O)$R_a$ and S(=O)$_2$$R_b$; each $R_a$ is independently hydrogen, alkyl, alkenyl, alkynyl, cycloalkyl, cycloalkenyl, or aryl; and each $R_b$ is independently alkyl, alkenyl, alkynyl, cycloalkyl, cycloalkenyl, or aryl.

12. The method of claim 11, wherein the pharmaceutically acceptable carrier is selected from the group consisting of a sugar, a starch, a cellulose, an oil, a glycol, an alcohol, an ester, and a fatty acid ester of sorbitan.

13. The method of claim 11, wherein the pharmaceutically acceptable carrier is a sugar.

14. The method of claim 13, wherein the sugar is selected from the group consisting of lactose, glucose, and sucrose.

15. The method of claim 11, wherein the bacterial infection is caused by a Gram-positive bacterium.

16. The method of claim 15, wherein the Gram-positive bacterium is selected from the group consisting of *Streptococcus, Staphylococcus, Enterococcus, Corynebacteria, Listeria, Bacillus, Erysipelothrix, Mycobacterium, Clostridium*, and *Actinomycetales*.

17. The method of claim 15, wherein the Gram-positive bacterium is selected from the group consisting of methicillin-susceptible and methicillin-resistant staphylococci (including *Staphylococcus aureus, Staphylococcus epidermidis, Staphylococcus haemolyticus, Staphylococcus hominis, Staphylococcus saprophyticus*, and coagulase-negative staphylococci), glycopeptide intermediate-susceptible *Staphylococcus aureus* (GISA), penicillin-susceptible and penicillin-resistant streptococci (including *Streptococcus pneumoniae, Streptococcus pyogenes, Streptococcus agalactiae, Streptococcus dysgalactiae, Streptococcus avium, Streptococcus bovis, Streptococcus lactis, Streptococcus sangius, Streptococcus anginosus, Streptococcus intermedius, Streptococcus constellatus* and Streptococci Group C, Streptococci Group G and *Viridans streptococci*), enterococci (including vancomycin-susceptible and vancomycin-resistant strains such as *Enterococcus faecalis* and *Enterococcus faecium*), *Clostridium difficile, Clostridium clostridiiforme, Clostridium innocuum, Clostridium perfringens, Clostridium tetani, Mycobacterium tuberculosis, Mycobacterium avium, Mycobacterium intracellulare, Mycobacterium kansaii, Mycobacterium gordonae, Mycobacteria sporozoites, Listeria monocytogenes, Bacillus subtilis, Bacillus anthracis, Corynebacterium diphtherias, Corynebacterium jeikeium, Corynebacterium sporozoites, Erysipelothrix rhusiopathiae*, and *Actinomyces israelli*.

18. The method of claim 17, wherein the bacterial infection is caused by *Bacillus anthracis*.

19. The method of claim 11, wherein the bacterial infection is caused by a Gram-negative bacterium.

20. The method of claim 19, wherein the Gram-negative bacterium is selected from the group consisting of *Helicobacter pylori, Legionella pneumophilia, Neisseria gonorrhoeae, Neisseria meningitidis*, pathogenic *Campylobacter sporozoites, Haemophilus influenzae, Pseudomonas aeruginosa, Enterobacter aerogenes, Enterobacter cloacae, Klebsiella pneumoniae, Klebsiella oxytoca, Pasteurella multocida, Bacteroides sporozoites, Bacteroides fragilis, Bacteroides thetaiotaomicron, Bacteroides uniformis, Bacteroides vulgatus Fusobacterium nucleatum, Streptobacillus moniliformis, Leptospira, Escherichia coli, Salmonella enterica, Salmonella salamae, Salmonella arizonae, Salmonella diarizonae, Salmonella houtenae, Salmonella bongori, Salmonella indica, Salmonella Enteritidis, Salmonella typhi*, and *Citrobacter freundii*.

\* \* \* \* \*